United States Patent
Wiedenmayer et al.

(10) Patent No.: US 9,096,548 B2
(45) Date of Patent: Aug. 4, 2015

(54) PYRAZINE AMIDE COMPOUNDS

(71) Applicants: Dieter Wiedenmayer, Biberach an der Riss (DE); Armin Heckel, Biberach an der Riss (DE); Dieter Hamprecht, Pozzolengo (IT)

(72) Inventors: Dieter Wiedenmayer, Biberach an der Riss (DE); Armin Heckel, Biberach an der Riss (DE); Dieter Hamprecht, Pozzolengo (IT)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/453,642

(22) Filed: Aug. 7, 2014

(65) Prior Publication Data
US 2015/0045326 A1    Feb. 12, 2015

(30) Foreign Application Priority Data
Aug. 8, 2013   (EP) ..................................... 13179737

(51) Int. Cl.
| | |
|---|---|
| *C07D 401/12* | (2006.01) |
| *C07D 403/08* | (2006.01) |
| *C07D 403/12* | (2006.01) |
| *C07D 241/26* | (2006.01) |
| *A61K 31/19* | (2006.01) |
| *A61K 31/4965* | (2006.01) |
| *A61K 31/497* | (2006.01) |
| *A61K 31/4985* | (2006.01) |
| *A61K 31/5377* | (2006.01) |
| *A61K 31/541* | (2006.01) |
| *A61K 31/55* | (2006.01) |
| *A61K 31/662* | (2006.01) |
| *A61K 45/06* | (2006.01) |
| *C07C 53/18* | (2006.01) |
| *C07D 401/14* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 487/04* | (2006.01) |
| *C07F 9/54* | (2006.01) |
| *C07D 241/20* | (2006.01) |

(52) U.S. Cl.
CPC .............. *C07D 241/26* (2013.01); *A61K 31/19* (2013.01); *A61K 31/497* (2013.01); *A61K 31/4965* (2013.01); *A61K 31/4985* (2013.01); *A61K 31/5377* (2013.01); *A61K 31/541* (2013.01); *A61K 31/55* (2013.01); *A61K 31/662* (2013.01); *A61K 45/06* (2013.01); *C07C 53/18* (2013.01); *C07D 241/20* (2013.01); *C07D 401/12* (2013.01); *C07D 401/14* (2013.01); *C07D 403/12* (2013.01); *C07D 405/14* (2013.01); *C07D 409/14* (2013.01); *C07D 413/14* (2013.01); *C07D 417/14* (2013.01); *C07D 487/04* (2013.01); *C07F 9/5456* (2013.01)

(58) Field of Classification Search
CPC ... C07D 401/12; C07D 403/08; C07D 403/12
USPC ....................................... 544/407; 514/255.06
See application file for complete search history.

(56) References Cited

U.S. PATENT DOCUMENTS

| | | | |
|---|---|---|---|
| 8,236,808 B2 * | 8/2012 | Collingwood et al. | 514/255.06 |
| 2012/0208815 A1 * | 8/2012 | Burger et al. | 514/235.5 |

FOREIGN PATENT DOCUMENTS

| | | |
|---|---|---|
| WO | 2009150137 | 12/2009 |
| WO | 2011028740 A1 | 3/2011 |
| WO | 2011079087 A1 | 6/2011 |

OTHER PUBLICATIONS

Hunt, et al., "Discovery of a novel chemotype of potent human ENaC blockers using a bioisostere approach Part 1: Quaternary amines", Bioorganic and Medicinal Chemistry Letters, vol. 22, No. 2, 2011, p. 929-932, (retrieved on Dec. 8, 2011), ISSN:0960-894X,DOI:10.1016/J.BMCL.2011.12.016.

Hunt, et al., "Discovery of a novel chemotype of potent human ENaC blockers using a bioisotere approach. Part 2: [alpha]-Branched quartenary amines", Bioorganic and Medicinal Chemistry Letters, vol. 22, No. 8, 2012, p. 2877-2879, XP055084884, ISSN:0960-894X, DOI:10.1016/j.bmv1.2012.02.067.

* cited by examiner

*Primary Examiner* — Bruck Kifle
(74) *Attorney, Agent, or Firm* — Michael P. Morris; Edward S. Lazer

(57) ABSTRACT

The present invention relates to compounds of formula 1 or pharmaceutically acceptable salt thereof,

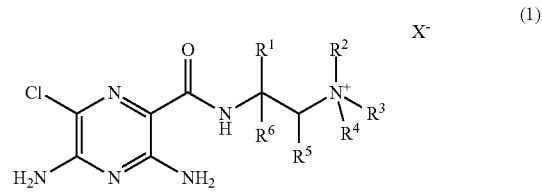

wherein $R^1$, $R^2$, $R^3$, $R^5$, $R^4$, $R^5$, $R^6$ and $X^-$ have the meanings as indicated in the specification, to their use as a medicament, to their use in the treatment of a disease selected from among respiratory diseases or complaints and allergic diseases of the airways, to pharmaceutical composition comprising at least one of said compound or a pharmaceutically acceptable salt thereof, as well as to medicament combinations containing one or more of said compounds or a pharmaceutically acceptable salt thereof.

19 Claims, No Drawing

PYRAZINE AMIDE COMPOUNDS

FIELD OF THE INVENTION

The present invention relates to compounds of formula 1 or pharmaceutically acceptable salt thereof,

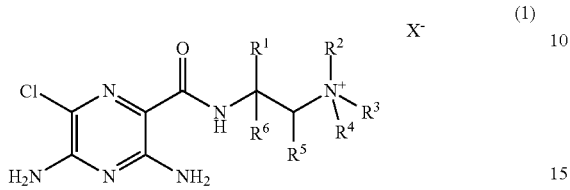

(1)

wherein $R^1$, $R^2$, $R^3$, $R^5$, $R^6$, and $X^-$ have one of the meanings as indicated in the specification, to their use as a medicament, to their use in the treatment of a disease selected from among respiratory diseases or complaints and allergic diseases of the airways, to pharmaceutical composition comprising at least one of said compound or a pharmaceutically acceptable salt thereof, as well as to medicament combinations containing one or more of said compounds or a pharmaceutically acceptable salt thereof.

BACKGROUND TO THE INVENTION

WO2011079087 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways. The new compounds of the present invention exhibit a longer lasting activity in topical lung treatment. The new compounds of the present invention further exhibit a reduced permeability being beneficial for topical lung treatment.

DETAILED DESCRIPTION OF THE INVENTION

The present invention relates to a compound of formula 1,

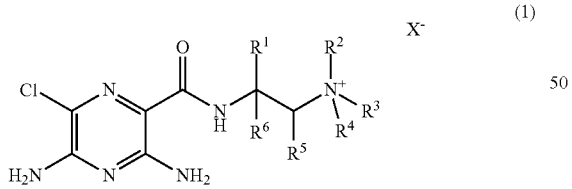

(1)

wherein
$R^1$ is selected from methyl, HO(O)C—$CH_2$—, $C_{1-4}$-alkyl-O(O)C—$CH_2$—, Cl($C_{1-4}$-alkyl)$_3$N—$CH_2$—$CH_2$—HN(O)C—$CH_2$— or aryl;
$R^6$ is selected from H or $C_{1-4}$-alkyl;
$R^2$ is selected from $C_{1-4}$-alkyl;
$R^3$ is selected from $C_{1-4}$-alkyl, optionally substituted with one or two groups selected from $C_{5-6}$-cycloalkyl, indolyl, HO(O)C—, $C_{1-4}$-alkyl-O(O)C—, $C_{5-6}$-cycloalkyl-O(O)C—, aryl-O— optionally substituted with $C_{1-4}$-alkyl-O—, aryl-$C_{1-4}$-alkyl optionally substituted with $C_{1-4}$-alkyl-O—, or
aryl optionally substituted with one or two $R^{3.1}$—, $R^{3.1}$—O—, $R^{3.1}$—$CH_2$—, $R^{3.1}$—$CH_2$—O—, halogen or NC—, wherein
$R^{3.1}$ is selected independently from H, $C_{1-4}$-alkyl, benzyl, HO(O)C—, $C_{1-4}$-alkyl-O(O)C—, HO—$CH_2$—, $C_{1-4}$-alkyl-O—$CH_2$—, ($C_{1-4}$-alkyl)$_2$N—$CH_2$—, $C_{1-4}$-alkyl-(O)$_2$S, H—[O—$CH_2$—$CH_2$]$_n$—, $R^{3.1.1}$HN(O)C—, ($R^{3.1.1}$)$_2$N(O)C—, $R^{3.1.2}$HN(O)C— or ($R^{3.1.2}$)$_2$N(O)C—, wherein
n is 3, 4 or 5,
$R^{3.1.1}$ is selected independently from H, H—[O—$CH_2$—$CH_2$]$_2$—, H—[O—$CH_2$—$CH_2$]$_3$— or a five-, six- or nine-membered heterocyclyl, wherein one, two or three elements are replaced by an element independently selected from N, O or S; each five-, six- or nine-membered heterocyclyl optionally substituted with one or two substituents independently selected from $C_{1-4}$-alkyl-, HO—, HO—$C_{1-4}$-alkyl- or O= or
two substituents $R^{3.1.1}$ together with the nitrogen atom they are bound to form a five-, six- or nine-membered heterocyclyl, wherein one or two further elements are replaced by an element independently selected from N, O or S; each five-, six- or nine-membered heterocyclyl optionally substituted with one or two substituents independently selected from $C_{1-4}$-alkyl, $C_{1-4}$-alkyl-O— or O=, and
$R^{3.1.2}$ is independently branched or unbranched $C_{1-4}$-alkyl, optionally substituted with one or two substituents selected independently from O=, NC—, HO—, $C_{1-4}$-alkyl-O—, ($C_{1-4}$-alkyl)$_2$N—, Cl($C_{1-4}$-alkyl)$_3$N—, HO(O)C—, $C_{1-4}$-alkyl-O(O)C—, HO(O)$_2$S—, $C_{1-4}$-alkyl-(O)$_2$S—, $C_{1-4}$-alkyl-(O)$_2$S—, ($C_{1-4}$-alkyl)$_2$OP— or a five- or six-membered heterocyclyl or heteroaryl, wherein one or two elements are replaced by an element independently selected from N or O; each five- or six-membered heterocyclyl or heteroaryl being optionally substituted with one or two substituents independently selected from $C_{1-4}$-alkyl or O=;
$R^4$ is independently selected from $C_{1-4}$-alkyl, optionally substituted with one or two groups selected from $C_{5-6}$-cycloalkyl, indolyl, HO(O)C—, $C_{1-4}$-alkyl-O(O)C—, $C_{5-6}$-cycloalkyl-O(O)C—, aryl-O— optionally substituted with $C_{1-4}$-alkyl-O—, aryl-$C_{1-4}$-alkyl optionally substituted with $C_{1-4}$-alkyl-O—, or aryl optionally substituted with one or two $R^{4.1}$—, $R^{4.1}$—O—, $R^{4.1}$—$CH_2$—, $R^{4.1}$—$CH_2$—O—, halogen or NC—, wherein $R^{4.1}$ is selected independently from H, $C_{1-4}$-alkyl, benzyl, HO(O)C—, $C_{1-4}$-alkyl-O(O)C—, HO—$CH_2$—, $C_{1-4}$-alkyl-O—$CH_2$—, ($C_{1-4}$-alkyl)$_2$N—$CH_2$—, $C_{1-4}$-alkyl-(O)$_2$S, H—[O—$CH_2$—$CH_2$]$_n$—, $R^{4.1.1}$HN(O)C—, ($R^{4.1.1}$)$_2$N(O)C—, $R^{4.1.2}$HN(O)C— or ($R^{4.1.2}$)$_2$N(O)C—, wherein
n is 3, 4 or 5,
$R^{4.1.1}$ is selected independently from H, H—[O—$CH_2$—$CH_2$]$_2$—, H—[O—$CH_2$—$CH_2$]$_3$— or a five-, six- or nine-membered heterocyclyl, wherein one, two or three elements are replaced by an element independently selected from N, O or S; each five-, six- or nine-membered heterocyclyl being optionally substituted with one or two substituents independently selected from $C_{1-4}$-alkyl-, HO—, HO—$C_{1-4}$-alkyl-, O= or
two substituents $R^{4.1.1}$ together with the nitrogen atom they are bound to form a five-, six- or nine-membered heterocyclyl, wherein one or two further elements are replaced by an element independently selected from N, O or S; each five-, six- or nine-membered heterocyclyl being optionally substituted with one or two substituents independently selected from $C_{1-4}$-alkyl-, HO—, HO—$C_{1-4}$-alkyl-, O=, and $R^{4.1.2}$ is branched or unbranched $C_{1-4}$-alkyl, optionally substituted with one or two substituents selected independently from O=, NC—, HO—, $C_{1-4}$-alkyl-O—, $(C_{1-4}$-alkyl$)_2$N—, Cl$(C_{1-4}$-alkyl$)_3$N—, HO(O)C—, $C_{1-4}$-alkyl-O(O)C—, HO(O)$_2$S—, $C_{1-4}$-alkyl-(O)$_2$S—, $C_{1-4}$-alkyl-(O)$_2$S—, $(C_{1-4}$-alkyl$)_2$OP— or a five- or six-membered heterocyclyl or heteroaryl, wherein one or two elements are replaced by an element independently selected from N or O; each five- or six-membered heterocyclyl or heteroaryl being optionally substituted with one or two substituents independently selected from $C_{1-4}$-alkyl or O=;

$R^5$ is H;

or $R^1$ and $R^2$ are together $R^{12}$, wherein $R^{12}$ is selected from $C_{2-4}$-alkylene each optionally partially or fully substituted with $R^{12.1}$, wherein $R^{12.1}$ is selected independently from phenyl, optionally substituted with $C_{1-4}$-alkyl;

or $R^1$, $R^2$ and $R^4$ together with the atoms connecting them form an aza-bicyclo[2.2.2]octane;

or $R^1$ and $R^5$ are together —CH$_2$—; and $X^-$ is selected independently from chloride, bromide, iodide, hydroxide, hydrogensulfate, nitrate, formiate, acetate, trifluoroacetate, methanesulfonate or p-toluenesulfonate;

or a pharmaceutically acceptable salt thereof.

The compounds of formula (1) or the pharmaceutically acceptable salts thereof as defined herein are particularly suitable for the treatment of pathophysiological processes treatable by the blockade of an epithelial sodium channel, particularly for the treatment of the lungs and airways.

Accordingly the present invention further relates to the compound of formula (1) as defined herein or a pharmaceutically acceptable salt thereof for use as a medicament.

The present invention further relates to the compound of formula (1) as defined herein or a pharmaceutically acceptable salt thereof for use in the treatment of a disease selected from among respiratory diseases or complaints and allergic diseases of the airways.

The present invention particularly relates to compounds of formula (1) or pharmaceutically acceptable salts thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins, more particularly for use in the treatment of a disease selected from chronic bronchitis, acute bronchitis, bronchitis, chronic obstructive bronchitis (COPD), asthma (intrinsic or allergic), cystic fibrosis and pediatric asthma, preferably chronic bronchitis, COPD and cystic fibrosis.

The present invention further relates to pharmaceutical compositions comprising at least one compound of formula (1) or a pharmaceutically acceptable salt thereof as defined herein and a pharmaceutically acceptable carrier.

The present invention further relates to medicament combinations which contain, besides one or more compounds of formula (1) or a pharmaceutically acceptable salts thereof as defined herein, as further active substances, one or more compounds selected from among the categories of further ENaC inhibitors, betamimetics, anticho-linergics, corticosteroids, PDE4-inhibitors, LTD4-antagonists, EGFR-inhibitors, dopamine ago-nists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, H$_2$N, OS, O$_2$S, NC (cyano), HOOC, F$_3$C or the like, the skilled artisan can see the radical attachment point(s) to the molecule from the free valences of the group itself. For combined groups comprising two or more subgroups, the terminal bond indicates the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

If a compound of the present invention is depicted in the form of a chemical name and as a formula in case of any discrepancy the formula shall prevail.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups;

Aromatic or non-aromatic ring systems consisting of carbon atoms and optionally heteroatoms, which may in turn be substituted by functional groups; or A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl) pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethane-sulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

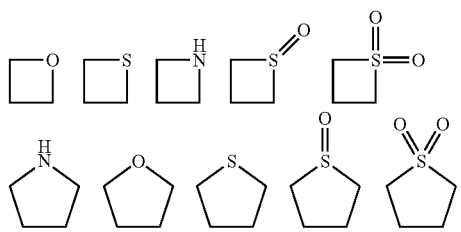

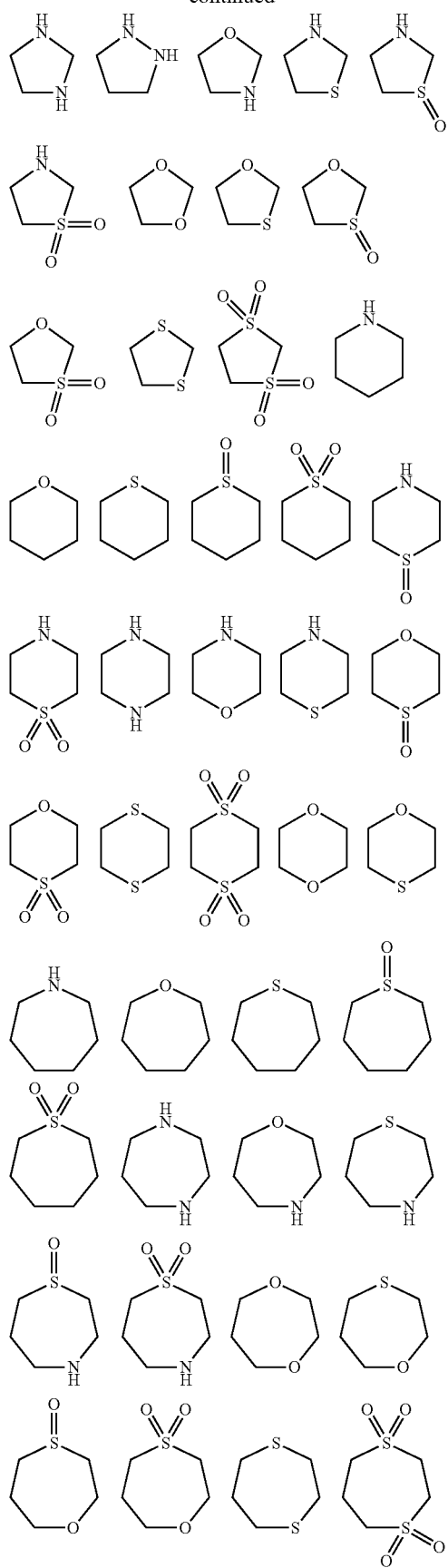
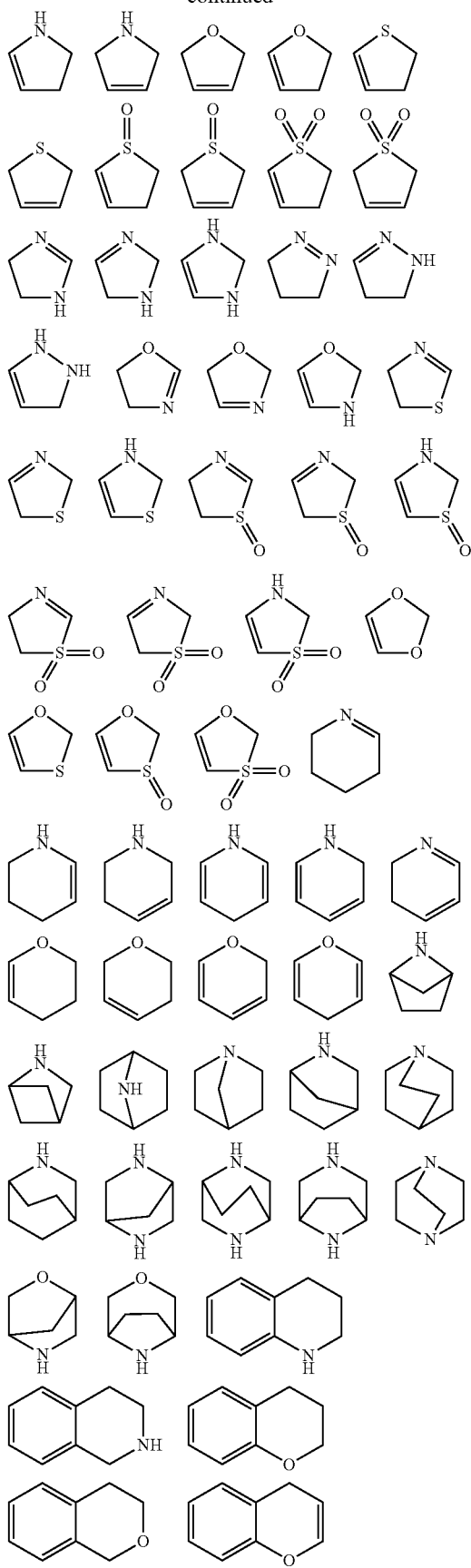

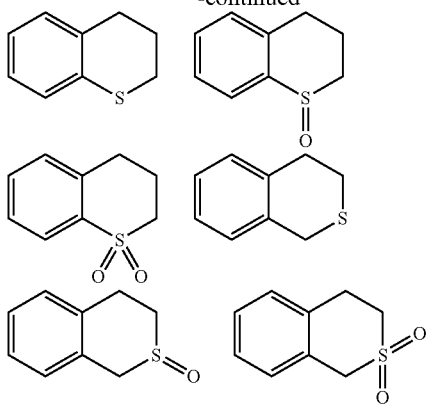
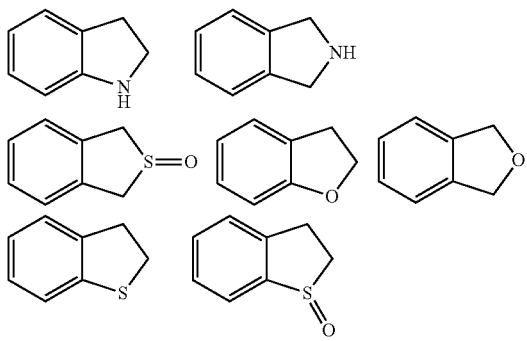
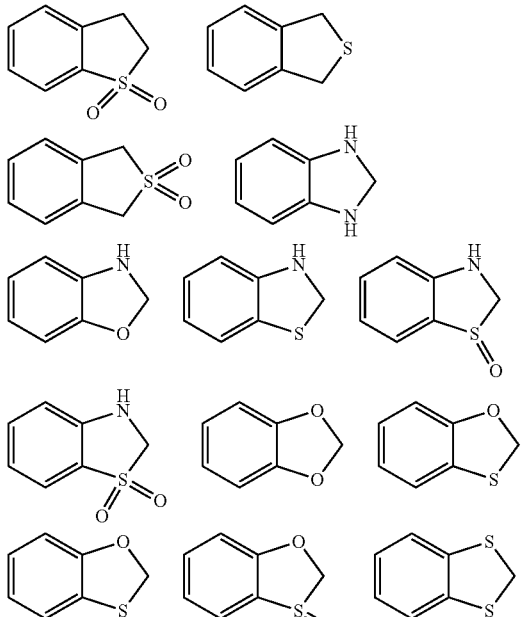

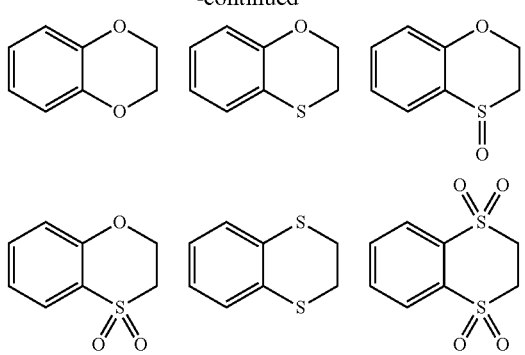

The term heteroaromatic means heteroaryl, monocyclic $C_{5-14}$-heteroaryl, or polycyclic $C_{5-14}$-heteroaryl. The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

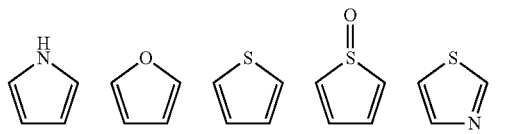
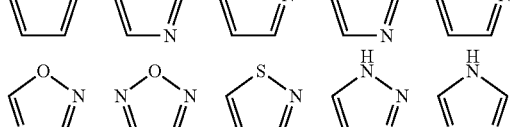
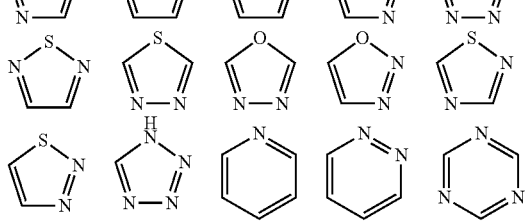
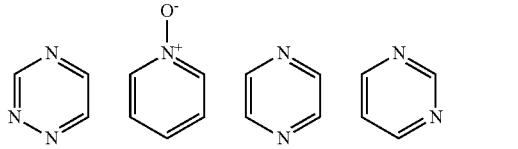
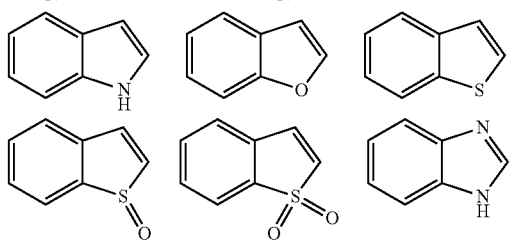

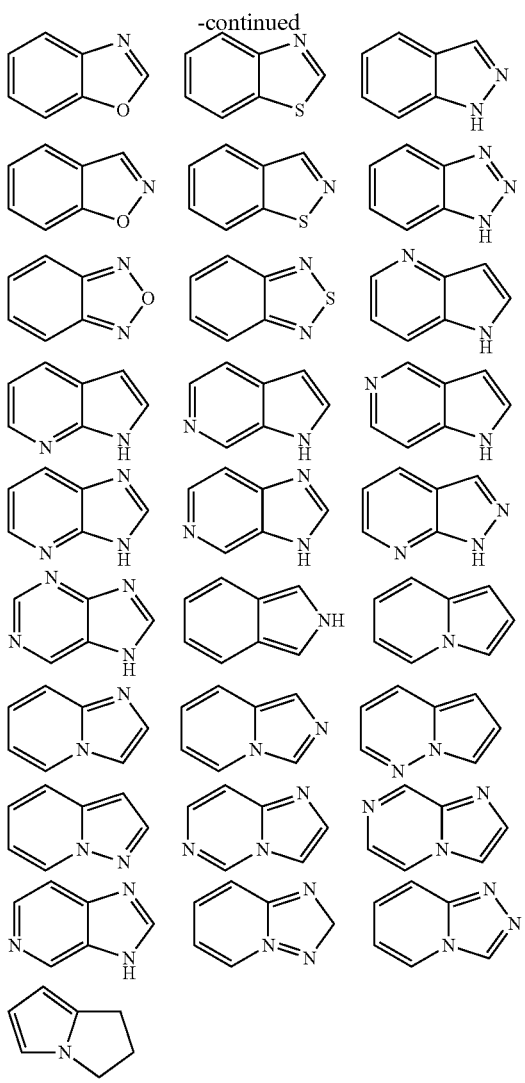

The term "halogen" as used herein means a halogen substituent selected from fluoro, chloro, bromo or iodo.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes $—CH_2—$, $—CH_2—CH_2—$, $—CH(CH_3)—$, $—CH_2—CH_2—CH_2—$, $—C(CH_3)_2—$, $—CH(CH_2CH_3)—$, $—CH(CH_3)—CH_2—$, $—CH_2—CH(CH_3)—$, $—CH_2—CH_2—CH_2—CH_2—$, $—CH_2—CH_2—CH(CH_3)—$, $—CH(CH_3)—CH_2—CH_2—$, $—CH_2—CH(CH_3)—CH_2—$, $—CH_2—C(CH_3)_2—$, $—C(CH_3)_2—CH_2—$, $—CH(CH_3)—CH(CH_3)—$, $—CH_2—CH(CH_2CH_3)—$, $—CH(CH_2CH_3)—CH_2—$, $—CH(CH_2CH_2CH_3)—$, $—CH(CH(CH_3))_2—$ and $—C(CH_3)(CH_2CH_3)—$.

By the term "$C_{1-6}$-alkoxy" (including those which are part of other groups) are meant branched and unbranched alkoxy groups with 1 to 6 carbon atoms and by the term "$C_{1-4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

In all cases of contradictions between structure and their naming, structure shall prevail.

Preferred Embodiments

A particular embodiment of the present invention relates to compounds of formula (1) or a pharmaceutically acceptable salt thereof, as defined herein, wherein $R^1$ is selected from methyl, $HO(O)C—CH_2—$, $C_{1-4}$-alkyl-$O(O)C—CH_2—$, $Cl(C_{1-4}$-alkyl$)_3N—CH_2—CH_2—HN(O)C—CH_2—$ and aryl. Preferably $R^1$ is selected independently from methyl, $HO(O)C—CH_2—$, $CH_3O(O)C—CH_2—$, $Cl(CH_3)_3N—CH_2—CH_2—HN(O)C—CH_2—$ phenyl.

Another particular embodiment of the present invention relates to compounds of formula (1) or a pharmaceutically acceptable salt thereof, as defined herein, wherein $R^1$ and $R^2$ are together $R^{12}$ and $R^{12}$ is selected from $C_{2-4}$-alkylene each optionally partially or fully substituted with $R^{12.1}$, wherein $R^{12.1}$ is selected independently from phenyl, optionally substituted with $C_{1-4}$-alkyl. Preferably $R^{12}$ is selected from $—CH_2—CH_2—$, $—CH_2—CH_2—CH_2—$, $—CH_2—CH_2—CH_2—CH_2—$ each optionally partially or fully substituted with $R^{12.1}$, wherein $R^{12.1}$ is selected independently from phenyl, optionally substituted with $CH_3—$. In this particular embodiment of the invention $R^1$ and $R^5$ cannot together be $—CH_2—$ and $R^1$, $R^2$ and $R^4$ cannot together with the atoms connecting them form an aza-bicyclo[2.2.2]octane.

Another particular embodiment of the present invention relates to compounds of formula (1) or a pharmaceutically acceptable salt thereof, as defined herein, wherein $R^1$, $R^2$ and $R^4$ together with the atoms connecting them form an aza-bicyclo[2.2.2]octane, wherein said compound is selected from compounds of formula (2)

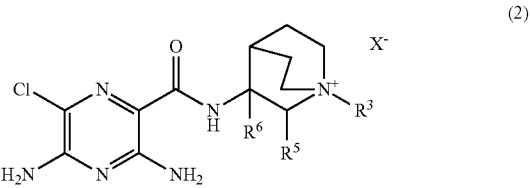

(2)

wherein $R^3$, $R^5$, $R^6$ and $X^-$ are as defined herein. In this particular embodiment of the invention $R^1$ and $R^2$ cannot together be $R^{12}$ and $R^1$ and $R^5$ cannot together be $CH_2$—.

Another particular embodiment of the present invention relates to compounds of formula (1) or a pharmaceutically acceptable salt thereof, as defined herein, wherein $R^1$ and $R^5$ are together —$CH_2$—. In this particular embodiment of the invention $R^1$ and $R^2$ cannot together be $R^{12}$ and $R^1$, $R^2$ and $R^4$ cannot together with the atoms connecting them form an aza-bicyclo[2.2.2]octane.

Another particular embodiment of the present invention relates to compounds of formula (1) or a pharmaceutically acceptable salt thereof, as defined herein, wherein $R^6$ is selected from H or $CH_3$. Preferably $R^6$ is H.

Another particular embodiment of the present invention relates to compounds of formula (1) or a pharmaceutically acceptable salt thereof, as defined herein, wherein $R^2$ is selected from $C_{1-4}$-alkyl. Preferably $R^2$ is $CH_3$.

Another particular embodiment of the present invention relates to compounds of formula (1) or a pharmaceutically acceptable salt thereof, as defined herein, wherein $R^3$ is selected from $C_{1-4}$-alkyl optionally substituted with one or two groups selected from $C_{5-6}$-cycloalkyl, indolyl, HO(O)C—$CH_2$—, $C_{1-4}$-alkyl-O(O)C—$CH_2$—, $C_{5-6}$-cycloalkyl-O(O)C—$CH_2$—, phenyl-O— optionally substituted with $C_{1-4}$-alkyl-O—, phenyl substituted with two halogen, phenyl optionally substituted with one $R^{3.1}$—, $R^{3.1}$—O—, $R^{3.1}$—$CH_2$—, $R^{3.1}$—$CH_2$—O—, halogen or NC—, wherein $R^{3.1}$ is independently selected from H, $C_{1-4}$-alkyl, benzyl, HO(O)C—, $C_{1-4}$-alkyl-O(O)C—, HO—$CH_2$—, $C_{1-4}$-alkyl-O—$CH_2$—, $(C_{1-4}$-alkyl$)_2$N—$CH_2$—, H—[O—$CH_2$—$CH_2]_n$—, $R^{3.1.1}$HN(O)C—, $(R^{3.1.1})_2$N(O)C—, $R^{3.1.2}$HN(O)C— or $(R^{3.1.2})_2$N(O)C—, n is 3, 4 or 5, $R^3$ is independently selected from H, H—[O—$CH_2$—$CH_2]_2$— or H—[O—$CH_2$—$CH_2]_3$— or a five or six-membered heterocyclyl independently selected from piperidinyl optionally substituted with $C_{1-4}$-alkyl, pyrrolidinyl optionally substituted with one or two substituents selected independently from $C_{1-4}$-alkyl or O═, tetrahydrofuranyl optionally substituted with $C_{1-4}$-alkyl-O—, or tetrahydrothiophenyl optionally substituted with two O═, or two substituents $R^{3.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine, each five, six- or nine-membered heterocyclyl being optionally substituted with one or two substituents selected independently from $C_{1-4}$-alkyl-, HO—, HO—$C_{1-4}$-alkyl- or O═, and $R^{3.1.2}$ is branched or unbranched $C_{1-4}$-alkyl, optionally substituted with one or two substituents selected independently from O═, NC—, HO—, $C_{1-4}$-alkyl-O—, $(C_{1-4}$-alkyl$)_2$N—, Cl$(C_{1-4}$-alkyl$)_3$N—, HO(O)C—, $C_{1-4}$-alkyl-O(O)C—, HO(O)$_2$S—, $C_{1-4}$-alkyl-(O)$_2$S—, $C_{1-4}$-alkyl-(O)$_2$S—, $(C_{1-4}$-alkyl$)_2$OP— or a five or six-membered heterocyclyl or heteroaryl selected from pyrrolidinyl, pyridyl, imidazolyl, piperidinyl, piperazinyl, morpholinyl, each five or six-membered heterocyclyl or heteroaryl being optionally substituted with one or two substituents selected independently from $C_{1-4}$-alkyl or O═.

Preferably $R^3$ is selected from $C_{1-4}$-alkyl optionally substituted with one or two groups selected from cyclohexyl, indolyl, HO(O)C—$CH_2$—, $CH_3$O(O)C—$CH_2$—, $C_2H_5$—O(O)C—$CH_2$—, cyclohexyl-O(O)C—$CH_2$—, phenyl-O— optionally substituted with $CH_3$O—, phenyl substituted with two F, or phenyl optionally substituted with one $R^{3.1}$—, $R^{3.1}$—O—, $R^{3.1}$—$CH_2$—, $R^{3.1}$—$CH_2$—O—, Cl or NC—, wherein $R^3$ is selected independently from H, $CH_3$, $C_2H_5$, benzyl, HO(O)C—, $CH_3$O(O)C—, HO—$CH_2$—, $CH_3$O—$CH_2$—, $(CH_3)_2$N—$CH_2$—, H—[O—$CH_2$—$CH_2]_n$—, $R^{3.1.1}$HN(O)C—, $(R^{3.1.1})_2$N(O)C—, $R^{3.1.2}$HN(O)C— or $(R^{3.1.2})_2$N(O)C—, wherein n is 3, 4 or 5, $R^{3.1.1}$ is independently selected from H, H—[O—$CH_2$—$CH_2]_2$—, H—[O—$CH_2$—$CH_2]_3$— or a five- or six-membered heterocyclyl selected from piperidinyl optionally substituted with $CH_3$, pyrrolidinyl optionally substituted with one or is two substituents selected independently from $CH_3$— or O═, tetrahydrofuranyl optionally substituted with $CH_3$O—, or tetrahydrothiophenyl optionally substituted with two O═, or two substituents $R^{3.1.1}$ together with the nitrogen atom they are bound to form a five-, six- or nine-membered heterocyclyl independently selected from piperidinyl, piperazinyl, morpholinyl, thiomorpholinyl, tetrahydro-imidazo[1,2-a]pyrazine; each five or six-membered heterocyclyl optionally substituted with one or two substituents selected independently from $CH_3$, HO—, HOCH$_2$—, HO—$CH_2$—$CH_2$—, or O═, and $R^{3.1.2}$ is branched or unbranched $C_{1-4}$-alkyl optionally substituted with one or two substituents independently selected from O═, NC—, HO—, $CH_3$O—, $(CH_3)_2$N—, Cl$(CH_3)_3$N—, HO(O)C—, $CH_3$O(O)C—, HO(O)$_2$S—, $CH_3$(O)$_2$S—, $CH_3$(O)$_2$S—, $(CH_3)_2$OP— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl is optionally substituted with one or two substituents selected independently from $CH_3$— or O═.

Another particular embodiment of the present invention relates to compounds of formula (1) or a pharmaceutically acceptable salt thereof, as defined herein, wherein $R^4$ is selected from $C_{1-4}$-alkyl optionally substituted with one or two groups selected from $C_{5-6}$-cycloalkyl, indolyl, HO(O)C—$CH_2$—, $C_{1-4}$-alkyl-O(O)C—$CH_2$—, $C_{5-6}$-cycloalkyl-O(O)C—$CH_2$—, phenyl-O— optionally substituted with $C_{1-4}$-alkyl-O—, phenyl substituted with two halogen, or phenyl optionally substituted with one $R^{4.1}$—, $R^{4.1}$—O—, $R^{4.1}$—$CH_2$—, $R^{4.1}$—$CH_2$—O—, halogen or NC—, wherein $R^{4.1}$ is independently selected from H, $C_{1-4}$-alkyl, benzyl, HO(O)C—, $C_{1-4}$-alkyl-O(O)C—, HO—$CH_2$—, $C_{1-4}$-alkyl-O—$CH_2$—, $(C_{1-4}$-alkyl$)_2$N—$CH_2$—, H—[O—$CH_2$—$CH_2]_n$—, $R^{4.1.1}$HN(O)C—, $(R^{4.1.1})_2$N(O)C—, $R^{4.1.2}$HN(O)C—, or $(R^{4.1.2})_2$N(O)C—, n is 3, 4 or 5, $R^{4.1.1}$ is independently selected from H, H—[O—$CH_2$—$CH_2]_2$—, H—[O—$CH_2$—$CH_2]_3$—, or a five or six-membered heterocyclyl independently selected from piperidinyl optionally substituted with $C_{1-4}$-alkyl, pyrrolidinyl optionally substituted with one or two substituents selected independently from $C_{1-4}$-alkyl or O═, tetrahydrofuranyl optionally substituted with $C_{1-4}$-alkyl-O—, or tetrahydrothiophenyl optionally substituted with two O═, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine, each five-, six- or nine-membered heterocyclyl being optionally substituted with one or two substituents selected independently from $C_{1-4}$-alkyl-, HO—, HO—$C_{1-4}$-alkyl-, O═, and $R^{4.1.2}$ is branched or unbranched $C_{1-4}$-alkyl optionally substituted with one or two substituents selected independently from O═, NC—, HO—, $C_{1-4}$-alkyl-O—, $(C_{1-4}$-alkyl$)_2$N—, Cl$(C_{1-4}$-alkyl$)_3$N—, HO(O)C—, $C_{1-4}$-alkyl-O(O)C—, HO(O)$_2$S—, $C_{1-4}$-alkyl-(O)$_2$S—, $C_{1-4}$-alkyl-(O)$_2$S—, $(C_{1-4}$-alkyl$)_2$OP— or five or six-membered heterocyclyl or heteroaryl selected from pyrrolidinyl, pyridyl, imidazolyl, piperidinyl, piperazinyl, morpholinyl, each five or six-membered heterocyclyl or heteroaryl being optionally substituted with one or two substituents selected independently from $C_{1-4}$-alkyl or O═.

Preferably $R^4$ is selected from $C_{1-4}$-alkyl optionally substituted with optionally substituted with one or two groups selected from cyclohexyl, indolyl, HO(O)C—$CH_2$—, $CH_3O$(O)C—$CH_2$—, $C_2H_5$—O(O)C—$CH_2$— or cyclohexyl-O(O)C—$CH_2$—, phenyl-O— optionally substituted with $CH_3O$—, phenyl substituted with two F, or phenyl optionally substituted with one $R^{4.1}$—, $R^{4.1}$—O—, $R^{4.1}$—$CH_2$—, $R^{4.1}$—$CH_2$—O—, Cl or NC—, wherein $R^{4.1}$ is selected independently from H, $CH_3$, $C_2H_5$, benzyl, HO(O)C—, $CH_3O$(O)C—, HO—$CH_2$—, $CH_3O$—$CH_2$—, $(CH_3)_2N$—$CH_2$—, H—[O—$CH_2$—$CH_2$]$_n$—, $R^{4.1.1}$HN(O)C—, $(R^{4.1.1})_2N$(O)C—, $R^{4.1.2}$HN(O)C— or $(R^{4.1.2})_2N$(O)C—, wherein n is 3, 4 or 5, $R^{4.1.1}$ is independently selected from H, H—[O—$CH_2$—$CH_2$]$_2$—, H—[O—$CH_2$—$CH_2$]$_3$—, or a five or six-membered heterocyclyl independently selected from piperidinyl optionally substituted with $CH_3$, pyrrolidinyl optionally substituted with one or two substituents selected independently from $CH_3$— or O═, tetrahydrofuranyl optionally substituted with $CH_3O$—, or tetrahydrothiophenyl optionally substituted with two O═, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, HO—$CH_2$—$CH_2$—, or O═, and $R^{4.1.2}$ is branched or unbranched $C_{1-4}$-alkyl optionally substituted with one or two substituents independently selected from O═, NC—, HO—, $CH_3O$—, $(CH_3)_2N$—, $Cl(CH_3)_3N$—, HO(O)C—, $CH_3O$(O)C—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl being optionally substituted with one or two substituents selected independently from $CH_3$— or O═.

Another particular embodiment of the present invention relates to compounds of formula (1) or a pharmaceutically acceptable salt thereof, as defined herein, wherein $R^5$ is H.

Another particular embodiment of the present invention relates to compounds of formula (1) or a pharmaceutically acceptable salt thereof, as defined herein, wherein $X^-$ is selected independently from chloride and trifluoroacetate.

In another particular embodiment of the present invention X may be absent if the compound of formula 1 itself contains an acidic substituent such as HO(O)C— or $HO(O)_2S$—, which can be deprotonated and form this way an internal salt.

A particularly preferred embodiment of the present invention relates to compounds of formula (1) or a pharmaceutically acceptable salt thereof, as defined herein, wherein $R^1$ is selected from methyl, HO(O)C—$CH_2$—, $CH_3O$(O)C—$CH_2$—, $Cl(CH_3)_3N$—$CH_2$—$CH_2$—HN(O)C—$CH_2$— or phenyl;

$R^6$ is selected from H or $CH_3$;

$R^2$ is $CH_3$;

$R^3$ is selected from $C_{1-4}$-alkyl optionally substituted with cyclohexyl, indolyl, HO(O)C—$CH_2$—, $CH_3O$(O)C—$CH_2$—, $C_2H_5$—O(O)C—$CH_2$— cyclohexyl-O(O)C—$CH_2$—, phenyl-O— optionally substituted is with $CH_3O$—, phenyl substituted with two F, or phenyl optionally substituted with one $R^{3.1}$—, $R^{3.1}$—O—, $R^{3.1}$—$CH_2$—, $R^{3.1}$—$CH_2$—O—, Cl or NC—, wherein $R^{3.1}$ is selected independently from H, $CH_3$—, $C_2H_5$—, benzyl, HO(O)C—, $CH_3O$(O)C—, HO—$CH_2$—, $CH_3O$—$CH_2$—, $(CH_3)_2N$—$CH_2$—, H—[O—$CH_2$—$CH_2$]$_n$—, $R^{3.1.1}$HN(O)C—, $(R^{3.1.1})_2N$(O)C—, $R^{3.1.2}$HN(O)C— or $(R^{3.1.2})_2N$(O)C—, wherein n is 3, 4 or 5, $R^{3.1.1}$ is selected from H, H—[O—$CH_2$—$CH_2$]$_2$—, H—[O—$CH_2$—$CH_2$]$_3$—, or a five or six-membered heterocycly selected from piperidinyl optionally substituted with $CH_3$, pyrrolidinyl optionally substituted with one or two substituents selected independently from $CH_3$— or O═, tetrahydrofuranyl optionally substituted with $CH_3O$—, or tetrahydrothiophenyl optionally substituted with two O═, or two substituents $R^{3.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, $HOCH_2$—$CH_2$—, or O═, and $R^{3.1.2}$ is branched or unbranched $C_{1-4}$-alkyl optionally substituted with one or two substituents selected independently from O═, NC—, HO—, $CH_3O$—, $(CH_3)_2N$—, $Cl(CH_3)_3N$—, HO(O)C—, $CH_3O$(O)C—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O═;

$R^4$ is selected from $C_{1-4}$-alkyl optionally substituted with one or two groups selected from cyclohexyl, indolyl, HO(O)C—$CH_2$—, $CH_3O$(O)C—$CH_2$—, $C_2H_5$—O(O)C—$CH_2$—, cyclohexyl-O(O)C—$CH_2$—, phenyl-O— optionally substituted with $CH_3O$—, phenyl substituted with two F, or phenyl optionally substituted with one $R^{4.1}$—, $R^{4.1}$—O—, $R^{4.1}$—$CH_2$—, $R^{4.1}$—$CH_2$—O—, Cl or NC—, wherein $R^{4.1}$ is selected independently from H, $CH_3$—, $C_2H_5$—, benzyl, HO(O)C—, $CH_3O$(O)C—, HO—$CH_2$—, $CH_3O$—$CH_2$—, $(CH_3)_2N$—$CH_2$—, H—[O—$CH_2$—$CH_2$]$_n$—, $R^{4.1.1}$HN(O)C—, $(R^{4.1.1})_2N$(O)C—, $R^{4.1.2}$HN(O)C— or $(R^{4.1.2})_2N$(O)C—, wherein n is 3, 4 or 5, $R^{4.1.1}$ is selected from H, H—[O—$CH_2$—$CH_2$]$_2$—, H—[O—$CH_2$—$CH_2$]$_3$—, or a five- or six-membered heterocyclyl selected from piperidinyl optionally substituted with $CH_3$, pyrrolidinyl optionally substituted with one or two substituents selected independently from $CH_3$— or O═, tetrahydrofuranyl optionally substituted with $CH_3O$—, or tetrahydrothiophenyl optionally substituted with two O═, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, HO—$CH_2$—$CH_2$—, or O═, and $R^{4.1.2}$ is branched or unbranched $C_{1-4}$-alkyl optionally substituted with one or two substituents selected independently from O═, NC—, HO—, $CH_3O$—, $(CH_3)_2N$—, $Cl(CH_3)_3N$—, HO(O)C—, $CH_3O$(O)C—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O=;

$R^5$ is H;

or $R^1$ and $R^2$ are together $R^{12}$, wherein $R^{12}$ is selected from —$CH_2$—$CH_2$—, —$CH_2$—$CH_2$—$CH_2$—, —$CH_2$—$CH_2$—$CH_2$—$CH_2$— each optionally substituted with $R^{12.1}$, wherein $R^{12.1}$ is selected independently from phenyl, optionally substituted with $CH_3$—;

or $R^1$, $R^2$ and $R^4$ together with the atoms connecting them form an aza-bicyclo[2.2.2]octane;

or $R^1$ and $R^5$ are together —$CH_2$—; and $X^-$ is selected from chloride or trifluoroacetate.

Another particularly preferred embodiment of the present invention relates to compounds of formula (1) or a pharmaceutically acceptable salt thereof, as defined herein, wherein $R^1$ and $R^2$ are together $R^{12}$, wherein $R^{12}$ is —$CH_2$—$CH_2$—$CH_2$—;

$R^6$ is H;

$R^3$ is selected from $C_{1-4}$-alkyl substituted with phenyl optionally substituted with one $R^{3.1}$—, $R^{3.1}$—O—, $R^{3.1}$—$CH_2$— or $R^{3.1}$—$CH_2$—O—, wherein $R^{3.1}$ is selected independently from H, $CH_3$—, $C_2H_5$—, benzyl, HO(O)C—, $CH_3$O(O)C—, HO—$CH_2$—, $CH_3$O—$CH_2$—, $(CH_3)_2$N—$CH_2$—, H—[O—$CH_2$—$CH_2]_n$—, $R^{3.1.1}$HN(O)C—, $(R^{3.1.1})_2$N(O)C—, $R^{3.1.2}$HN(O)C— or $(R^{3.1.2})_2$N(O)C—, wherein n is 3, 4 or 5, $R^{3.1.1}$ is selected from H, H—[OCH$_2$—CH$_2]_2$—, H—[OCH$_2$—CH$_2]_3$—, or a five or six-membered heterocycly selected from piperidinyl optionally substituted with $CH_3$, pyrrolidinyl optionally substituted with one or two substituents selected independently from $CH_3$— or O=, tetrahydrofuranyl optionally substituted with $CH_3$O—, or tetrahydrothiophenyl optionally substituted with two O=, or two substituents $R^{3.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, $HOCH_2$—$CH_2$—, or O=, and $R^{3.1.2}$ is branched or unbranched $C_{1-4}$-alkyl optionally substituted with one or two substituents selected independently from O=, NC—, HO—, $CH_3$O—, $(CH_3)_2$N—, $Cl(CH_3)_3$N—, HO(O)C—, $CH_3$O(O)C—, HO(O)$_2$S—, $CH_3$(O)$_2$S—, $CH_3$(O)$_2$S—, $(CH_3)_2$OP— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O=; and $R^4$ is selected from $C_{1-4}$-alkyl substituted with phenyl optionally substituted with one $R^{4.1}$—, $R^{4.1}$—O—$R^{4.1}$—$CH_2$— or $R^{4.1}$—$CH_2$—O—, wherein $R^{3.1}$ is selected independently from H, $CH_3$—, $C_2H_5$—, benzyl, HO(O)C—, $CH_3$O(O)C—, HO—$CH_2$—, $CH_3$O—$CH_2$—, $(CH_3)_2$N—$CH_2$—, H—[O—$CH_2$—$CH_2]_n$—, $R^{4.1.1}$HN(O)C—, $(R^{4.1.1})_2$N(O)C—, $R^{4.1.2}$HN(O)C— or $(R^{4.1.2})_2$N(O)C—, wherein n is 3, 4 or 5, $R^{4.1.1}$ is selected from H, H—[OCH$_2$—CH$_2]_2$—, H—[OCH$_2$.—CH$_2]_3$—, or a five or six-membered heterocycly selected from piperidinyl optionally substituted with $CH_3$, pyrrolidinyl optionally substituted with one or two substituents selected independently from $CH_3$— or O=, tetrahydrofuranyl optionally substituted with $CH_3$O—, or tetrahydrothiophenyl optionally substituted with two O=, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, $HOCH_2$—$CH_2$—, or O=, and $R^{4.1.2}$ is branched or unbranched $C_{1-4}$-alkyl optionally substituted with one or two substituents selected independently from O=, NC—, HO—, $CH_3$O—, $(CH_3)_2$N—, $Cl(CH_3)_3$N—, HO(O)C—, $CH_3$O(O)C—, HO(O)$_2$S—, $CH_3$(O)$_2$S—, $CH_3$(O)$_2$S—, $(CH_3)_2$OP— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O=.

Any and each other of the substituents defined above may be combined with each other. Particularly preferred are compounds of formula (1) or the pharmaceutically acceptable salts thereof wherein at 2, 3, 4, 5, 6 or 7 of the substituents defined herein have one of the particular or preferred meaning as defined herein.

Preparation

The compounds according to the invention may be obtained using methods of synthesis known in the art. Preferably the compounds are obtained by the following methods according to the invention which are described in more detail hereinafter.

Compounds of formula 1, as defined hereinbefore, may be formed as outlined in Scheme 1 by an amide coupling reaction between carboxylic acid I and an amine II. Many reagents and conditions to affect such reactions are known to those skilled in the art and well documented in the literature, e.g. in Han, S.-Y.; Kim, Y.-A. Tetrahedron 2004, 60, 2447. Examples of suitable conditions are exemplified herein. The amine and acid coupling partners may be employed as suitable salt forms, in which case it may be necessary to adjust the quantity of the base which may be added to the reaction. It is noted to those skilled in the art that the presence of certain functional groups in the reaction partners may interfere with the amide coupling. Where this applies suitable protecting groups as described e.g. in "Protective Groups in Organic Synthesis", 2$^{nd}$ edition, Greene T. W., Wuts P. G. M.; Wiley-Interscience: New York, 1991 or in "Protective Groups", Kocienski P. J.; Thieme: New York, 1994 can be used.

Scheme 1:

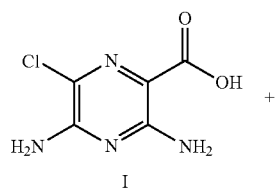

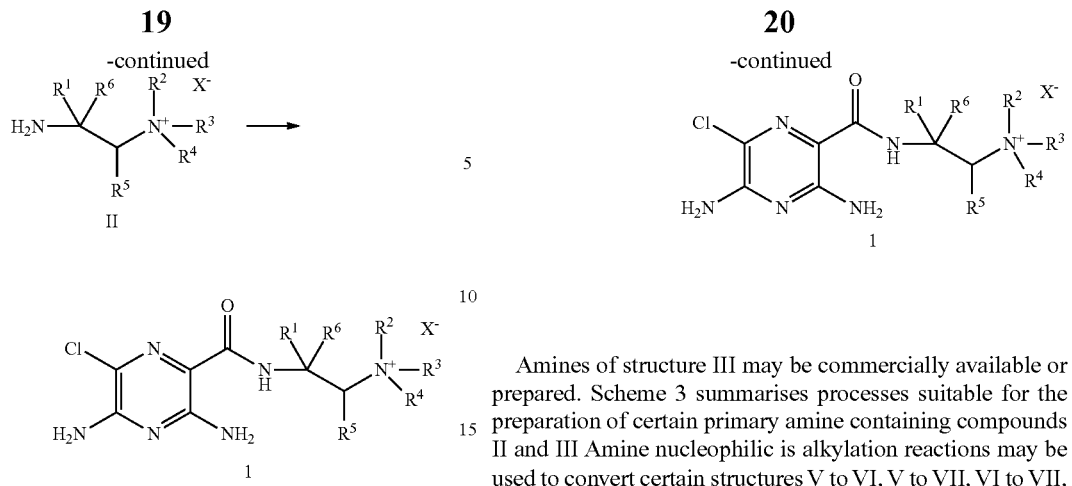

A further method to form compounds of formula 1, as defined hereinbefore, is outlined in Scheme 2. It comprises the reaction between a tertiary amine IV and an alkylating agent $R^3$—X, where X is a leaving group such as Cl, Br, I or a sulfonate ester, for example $OS(O)_2Me$. This method is particularly effective where amine IV is a good nucleophile, such as in those containing a quinuclidine substructure. Suitable reaction conditions are known to those skilled in the art, in particular those appropriate for alkylations following nucleophilic substitution mechanisms. A suitable example is provided herein. Compounds IV may be prepared as outlined for Scheme 1, but using an amine III instead of an amine II.

Scheme 2:

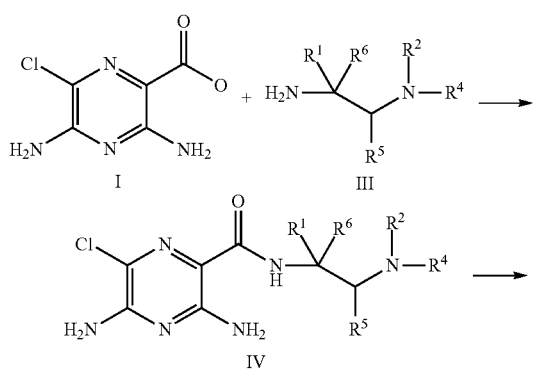

Amines of structure III may be commercially available or prepared. Scheme 3 summarises processes suitable for the preparation of certain primary amine containing compounds II and III Amine nucleophilic is alkylation reactions may be used to convert certain structures V to VI, V to VII, VI to VII, V to VIII, VI to IX, VII to IX and VIII to IX. The respective alkylating agents $R^2$—X, $R^4$—X and $R^3$—X typically contain a leaving group X such as Cl, Br, I or a sulfonate ester, for example $OS(O)_2Me$. Suitable reaction conditions are known to those skilled in the art to be those appropriate for alkylations following nucleophilic substitution mechanisms. Suitable examples are provided herein. Alternatively, conversions of certain structures V to VI, V to VII, VI to VII and V to VIII may be effected under conditions of reductive amination, using carbonyl derivatives which on reduction reveal the respective groups $R^2$, $R^4$ and $R^3$. Suitable reaction conditions for reductive amination reactions are known to those skilled in the art and may involve for example sodium triacetoxyborohydride, sodium cyanoborohydride or hydrogen in the presence of a suitable catalyst such as palladium on charcoal. It will be appreciated by those skilled in the art that during the alkylation reactions the primary amine fuction of compounds II and III may need to be protected. Suitable protecting groups PG as well as methods for their removal (VII to III, IX to II) are described e.g. in "*Protective Groups in Organic Synthesis*", $2^{nd}$ edition, Greene T. W., Wuts P. G. M.; Wiley Interscience: New York, 1991 or in "Protective Groups", Kocienski P. J.; Thieme: New York, 1994. Suitable examples of protecting groups for the primary amine may be tert-butyloxycarbonyl and benzyloxycarbonyl groups. Suitable amines, alkylating agents or carbonyl derivatives used in the processes described above may be commercially available or derived from commercially available precursors by functional group interconversions known to the skilled person and listed e.g. in "Comprehensive Organic Transformations, A Guide to Functional Group Preparations", $2^{nd}$ edition, Larock, R. C.; Wiley-VCH: New York, 1999.

Scheme 3:

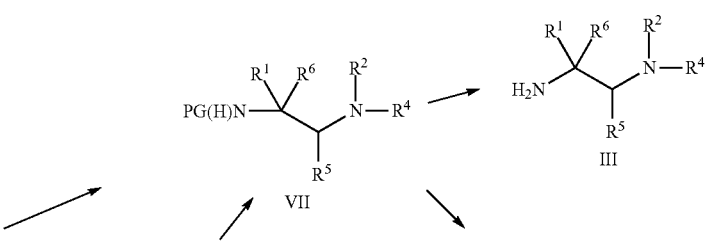

-continued

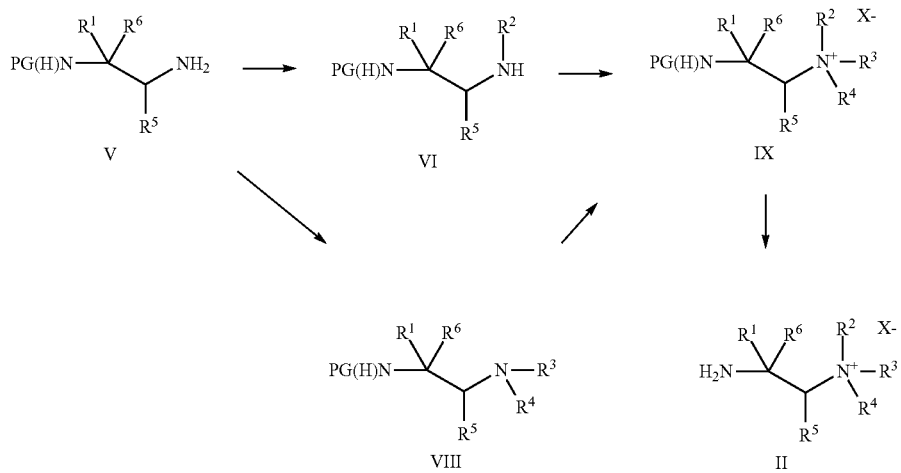

Residues R1a, R6, R3 or R4 may be interconverted from one form according to the invention into another form according to the invention, using functional group interconversions known to the skilled person and listed e.g. in "Comprehensive Organic Transformations, A Guide to Functional Group Preparations", $2^{nd}$ edition, Larock R. C.; Wiley-VCH: New York, 1999.

Compounds of formula 1, as defined hereinbefore, are salts containing an anion $X^-$. These anions $X^-$ may be derived from synthesis or purification or changed from one anionic species to another suitable anionic species by methods known to those skilled in the art. Examples of such methods are ion exchange using for example ion exchange resins or displacement of an acid counterion from its salt using another, usually stronger, acid. For example, treatment of a compound of formula 1, as defined hereinbefore, where $X^-$ is $CF_3COO^-$, with HCl in a suitable solvent, such as water or diethyl ether, may produce a compound of formula 1, as defined hereinbefore, where $X^-$ is $Cl^-$.

Certain compounds of formula 1, as defined hereinbefore, may contain groups that may be further converted into the salts thereof, for pharmaceutical use particularly into pharmaceutically acceptable salts with inorganic or organic acids and bases. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known to the skilled person.

Moreover, where one or more stereoisomers may exist, the compounds of general formula 1 or intermediates in the synthesis of compounds of general formula 1 may be obtained as mixtures and then resolved into their stereoisomers, e.g. enantiomers and/or diastereomers. Thus, for example, cis/trans mixtures may be resolved into their cis and trans isomers, and racemic compounds may be separated into their enantiomers.

Thus, for example, the cis/trans mixtures may be resolved by chromatography into the cis and trans isomers thereof. The compounds of general formula 1 or intermediates in the synthesis of compounds of general formula 1, which occur as racemates may be separated by methods known per se (cf. Allinger N. L. and Eliel E. L. in "Topics in Stereochemistry", Vol. 6, Wiley Interscience, 1971) into their optical antipodes and compounds of general formula 1 or intermediates in the synthesis of compounds of general formula 1 with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

EXAMPLES

The following examples illustrate the present invention without restricting its scope:

Example 1

Intermediate 1.1: 3-Amino-1,1-bis-[3-(4-methoxy-phenyl)-propyl]-piperidinium chloride hydrochloride

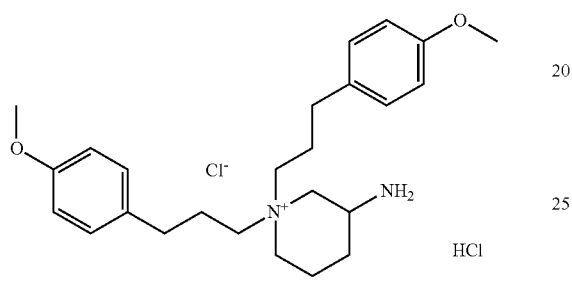

Piperidin-3-yl-carbamic acid tert-butyl ester (500 mg, 2.5 mmol), 1-(3-bromo-propyl)-4-methoxy-benzene (700 µl, 4 mmol), potassium carbonate (1.05 g, 7.6 mmol) and sodium iodide (100 mg, 0.67 mmol) are dissolved in acetonitril and stirred at reflux overnight. The solvent is removed under reduced pressure. The reaction mixture is acidified with saturated $KHSO_4$ solution and extracted with dichloromethane. Then the organic layer is concentrated in vacuum and the product is purified by preparative HPLC-MS (MeOH/$H_2O$+ 0.1% TFA). 1 M HCl is added and the solvent removed under reduced pressure at 60° C. to remove the BOC group and form the chloride salt. LC (method F): $t_R$=1.51 min; Mass spectrum ($ESI^+$): m/z=397 $[M]^+$.

Table of analoges:

| Intermediate | MOLECULAR STRUCTURE and NAME | ESI+ (M+)+ | Rt | HPLC method |
|---|---|---|---|---|
| 1.1.1 | 3-Amino-1,1-bis-[3-(4-methoxy-phenyl)-propyl]-pyrrolidinium chloride hydrochloride | 383 | 1.50 | F |

-continued

Table of analoges:

| Inter-mediate | MOLECULAR STRUCTURE and NAME | ESI+ (M+)+ | Rt | HPLC method |
|---|---|---|---|---|
| 1.1.2 | 3-Amino-1,1-bis-[3-(4-methoxy-phenyl)-propyl]-4-p-tolyl-pyrrolidinium chloride hydrochloride | 473 | 1.64 | F |
| 1.1.3 | 3-Amino-1,1-bis-[3-(4-methoxy-phenyl)-propyl]-azepanium chloride hydrochloride | 411 | 1.53 | F |
| 1.1.4 | S-3-Amino-1,1-bis-[3-(4-methoxy-phenyl)-propyl]-piperidinium chloride hydrochloride | 397 | 1.51 | F |
| 1.1.5 | R-3-Amino-1,1-bis-[3-(4-methoxy-phenyl)-propyl]-piperidinium chloride hydrochloride | 397 | 1.51 | F |

Example 1

3-[(3,5-Diamino-6-chloro-pyrazine-2-carbonyl)-amino]-1,1-bis-[3-(4-methoxy-phenyl)propyl]-piperidinium chloride

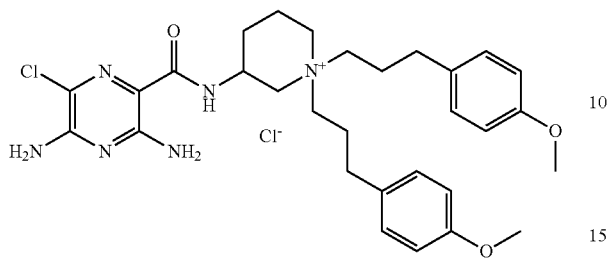

3-Amino-1,1-bis-[3-(4-methoxy-phenyl)-propyl]-piperidinium chloride hydrochloride (274 mg, 0.584 mmol)), 3,5-Diamino-6-chloro-pyrazine-2-carboxylic acid (117 mg, 0.612 mmol) and N,N-Diisopropylethylamine (300 µl, 1.7 mmol) are dissolved in N,N-dimethylformamide (6 ml), 2-(1H-Benzotriazol-1-yl)-1,1,3,3-tetramethyluronium tetrafluoroborate (192 mg, 0.6 mmol) is added. The reaction is stirred at room temperature overnight and purified by preparative HPLC-MS (MeOH/H2O+0.1% TFA). 0.3 mL 1 M HCl is added to form the chloride salt and the solvent is removed under reduced pressure. LC (method F): $t_R$=1.72 min; Mass spectrum (ESI$^+$): m/z=567 [M]$^+$.

Table of analoges:

| Example | MOLECULAR STRUCTURE and NAME | ESI+ (M+)+ | Rt | HPLC method | IC50 [µM] |
|---|---|---|---|---|---|
| 1.1 | 3-[(3,5-Diamino-6-chloro-pyrazine-2-carbonyl)-amino]-1,1-bis-[3-(4-methoxy-phenyl)-propyl]-pyrrolidinium chloride | 553 | 1.70 | F | 0.03 |
| 1.2 | 3-[(3,5-Diamino-6-chloro-pyrazine-2-carbonyl)-amino]-1,1-bis-[3-(4-methoxy-phenyl)-propyl]-(S)-4-p-tolyl-pyrrolidinium chloride | 643 | 1.88 | F | 0.20 |

-continued

Table of analoges:

| Example | MOLECULAR STRUCTURE and NAME | ESI+ (M+)+ | Rt | HPLC method | IC50 [µM] |
|---|---|---|---|---|---|
| 1.3 | 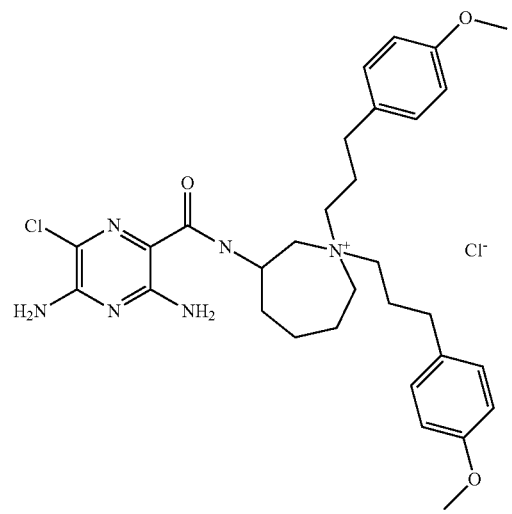<br>3-[(3,5-Diamino-6-chloro-pyrazine-2-carbonyl)-amino]-1,1-bis-[3-(4-methoxy-phenyl)-propyl]-azepanium chloride | 581 | 1.56 | G | 0.044 |
| 1.4 | 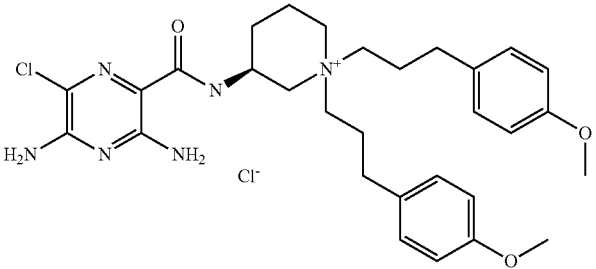<br>(S)-3-[(3,5-Diamino-6-chloro-pyrazine-2-carbonyl)-amino]-1,1-bis-[3-(4-methoxy-phenyl)-propyl]-piperidinium chloride | 567 | 1.36 | H | 0.004 |
| 1.5 | 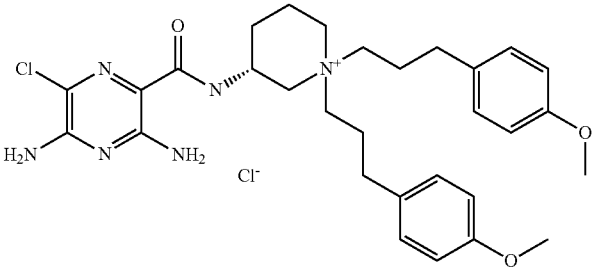 [SMILES: COc1ccc(CCC[N+]2(CCCc3ccc(OC)cc3)CCCC(NC(=O)c3nc(Cl)c(N)nc3N)C2)cc1 ; [Cl-]]<br>(R)-3-[(3,5-Diamino-6-chloro-pyrazine-2-carbonyl)-amino]-1,1-bis-[3-(4-methoxy-phenyl)-propyl]-piperidinium chloride | 567 | 1.36 | H | 0.038 |

Example 2

{2-[(3,5-Diamino-6-chloro-pyrazine-2-carbonyl)-amino]-cis-cyclopentyl}-bis-[3-(4-methoxy-phenyl)propyl]-methyl-ammonium chloride

Intermediate 2.1

(2-{Bis-[3-(4-methoxy-phenyl)-propyl]-amino}-1-phenyl-ethyl)-carbamic acid tert-butyl ester

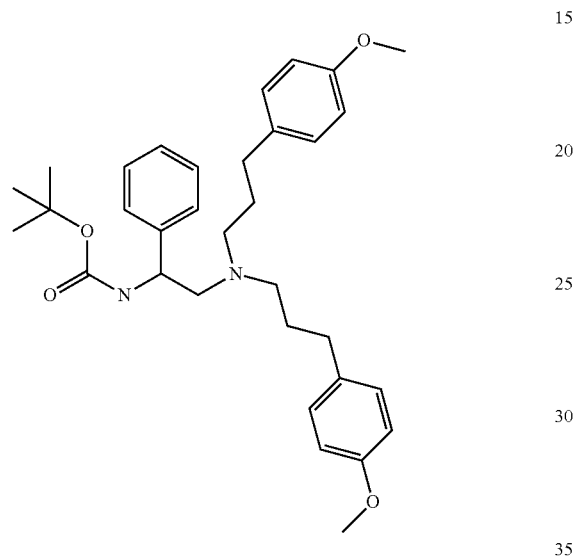

A solution of 2-amino-1-phenyl-ethyl-carbamic acid tert-butylester (47 mg, 0.2 mmol), 1-(3-Bromo-propyl)-4-methoxy-benzene (100 mg, 0.44 mmol), potassium carbonate (82 mg, 0.6 mmol) and sodium iodide (5 mg, 0.03 mmol) in acetonitrile is stirred at 80° C. for one night. The reaction mixture is acidified with acetic acid, concentrated under reduced pressure and the product is purified by preparative HPLC-MS (50° C., gradient: 45-65% MeOH/H2O+0.1% TFA). The solvent is removed under reduced pressure. Mass spectrum (ESI$^+$): m/z=533 [M+H]$^+$.

Table of analoges:

| Intermediate | MOLECULAR STRUCTURE and NAME | ESI+ (M + H)+ | Rt | HPLC method |
|---|---|---|---|---|
| 2.1.1 | (2-{Bis-[3-(4-methoxy-phenyl)-propyl]-amino}-trans-cyclopropyl)-carbamic acid tert-butyl ester | 469 | 1.89 | F |

Table of analoges:

| Intermediate | MOLECULAR STRUCTURE and NAME | ESI+ (M + H)+ | Rt | HPLC method |
|---|---|---|---|---|
| 2.1.2 | (S-2-{Bis-[3-(4-methoxy-phenyl)-propyl]-amino}-1-methyl-ethyl)-carbamic acid tert-butyl ester (Chiral) | 471 | n.d. | n.d. |
| 2.1.3 | (2-{Bis-[3-(4-methoxy-phenyl)-propyl]-amino}-1,1-dimethyl-ethyl)-carbamic acid tert-butyl ester | 485 | n.d. | G |

Intermediate 2.2

(2-Amino-2-phenyl-ethyl)-bis-[3-(4-methoxy-phenyl)-propyl]-methyl-ammonium chloride hydrochloride

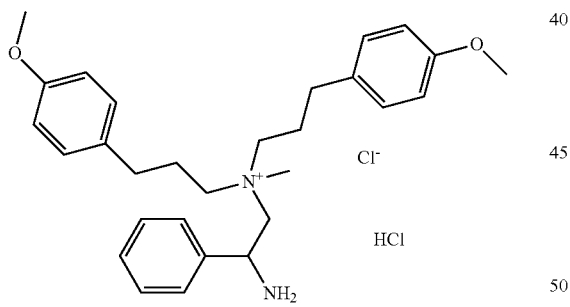

(2-{Bis-[3-(4-methoxy-phenyl)-propyl]-amino}-1-phenyl-ethyl)-carbamic acid tert-butyl ester (99 mg, 0.18 mmol) and methyliodide (40 mg, 0.27 mmol) are dissolved in 2 ml acetone and stirred for 4 days at 60° C. The solvent is removed under vacuo and the product is purified by prep. HPLC ($H_2O$ + 0.1% TFA and MeOH). The product is dissolved in 2 ml dioxan and 0.5 ml HCl in dioxan is added and stirred for one night and concentrated under vacuo to de-Boc and to form the HCl salt. LC (method M): $t_R$=1.36 min; Mass spectrum (ESI+): m/z=447 [M]+.

Table of analoges:

| Intermediate | MOLECULAR STRUCTURE and NAME | ESI+ (M+)+ | Rt | HPLC method |
|---|---|---|---|---|
| 2.2.1 | 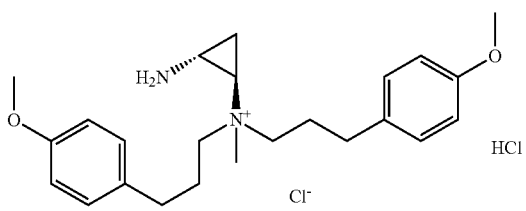<br>(2-Amino-trans-cyclopropyl)-bis-[3-(4-methoxy-phenyl)-propyl]-methyl-ammonium chloride hydrochloride | 383 | 1.48 | F |
| 2.2.2 | 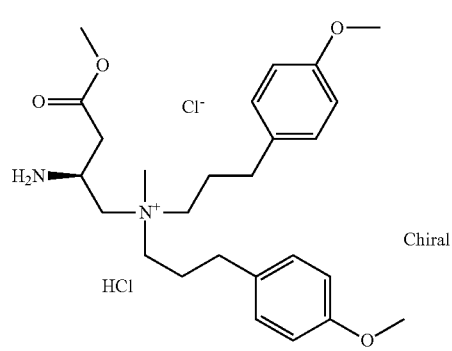<br>(S-2-Amino-3-methoxycarbonyl-propyl)-bis-[3-(4-methoxy-phenyl)-propyl]-methyl-ammonium chloride hydrochloride | 443 | 1.45 | I |
| 2.2.3 | 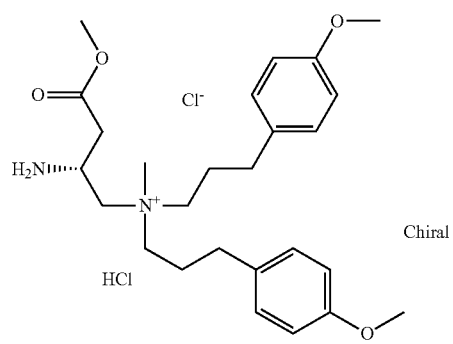<br>(R-2-Amino-3-methoxycarbonyl-propyl)-bis-[3-(4-methoxy-phenyl)-propyl]-methyl-ammonium chloride hydrochloride | 443 | 1.45 | I |
| 2.2.4 | 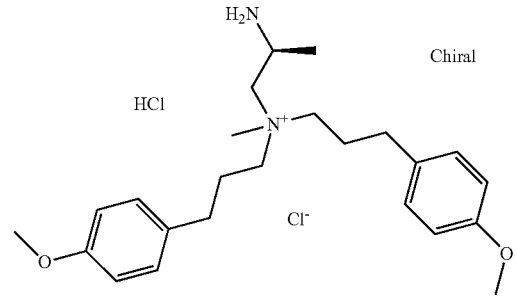<br>(2-Amino-propyl)-bis-[3-(4-methoxy-phenyl)-propyl]-methyl-ammonium chloride hydrochloride | 385 | 1.14 | H |

| Inter-mediate | MOLECULAR STRUCTURE and NAME | ESI+ (M+)+ | Rt | HPLC method |
|---|---|---|---|---|
| 2.2.5 | (S-2-Amino-3-oxo-3-pyrrolidin-1-yl-propyl)-bis-[3-(4-methoxy-phenyl)-propyl]-methyl-ammonium chloride hydrochloride | 468 | 1.19 | H |

Table of analoges:

Example 2

{2-[(3,5-Diamino-6-chloro-pyrazine-2-carbonyl)-amino]-2-phenyl-ethyl}-bis-[3-(4-methoxy-phenyl)-propyl]-methyl-ammonium chloride

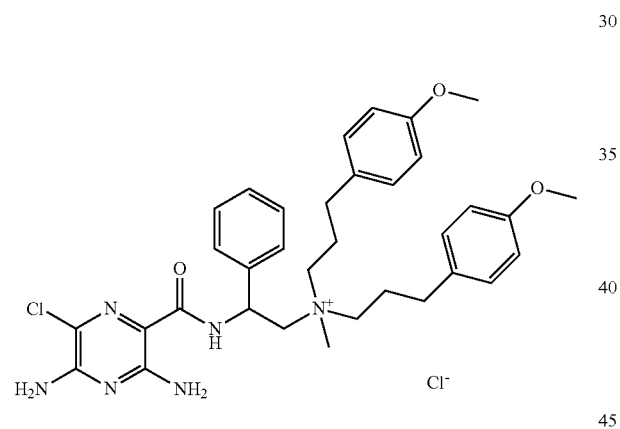

57 mg (0.11 mmol) 2-Amino-2-phenyl-ethyl)-bis-[3-(4-methoxy-phenyl)-propyl]-methyl-ammonium chloride hydrochloride, 3,5-Diamino-6-chloro-pyrazine-2-carboxylic acid (21 mg, 0.11 mmol) and N,N-Diisopropylethylamine (60 µl, 0.34 mmol) are dissolved in 2 ml N,N-dimethylformamide, 2-(1H-Benzotriazol-1-yl)-1,1,3,3-tetramethyluronium tetrafluoroborate (35 mg, 0.11 mmol) is added and stirred at room temperature overnight. The mixture is filtered and concentrated in vacuo. The product is purified by preparative HPLC-MS (MeOH/H2O+0.1% TFA). 1 mL 1 M HCl is added to form chloride salt and the solvent is removed under reduced pressure. LC (method F): $t_R$=1.43 min; Mass spectrum (ESI$^+$): m/z=617 [M]$^+$. IC50=0.03.

| | Table of analoges: | | | | |
|---|---|---|---|---|---|
| Example | Structure and name | ESI+ (M+)+ | Rt | HPLC methode | IC50 [µM] |
| 2.1 | 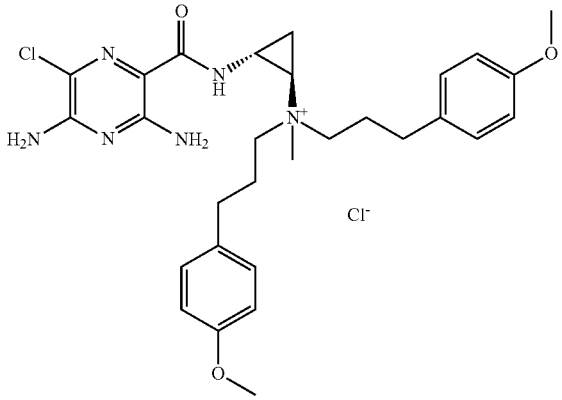{2-[(3,5-Diamino-6-chloro-pyrazine-2-carbonyl)-amino]-trans-cyclopropyl}-bis-[3-(4-methoxy-phenyl)-propyl]-methyl-ammonium chloride | 553 | 1.70 | F | 0.08 |
| 2.2 | 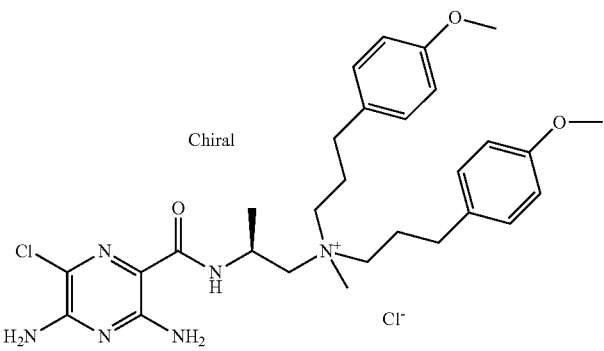{(S)-2-[(3,5-Diamino-6-chloro-pyrazine-2-carbonyl)-amino]-propyl}-bis-[3-(4-methoxy-phenyl)-propyl]-methyl-ammonium chloride | 555 | 1.28 | H | 0.13 |
| 2.3 | 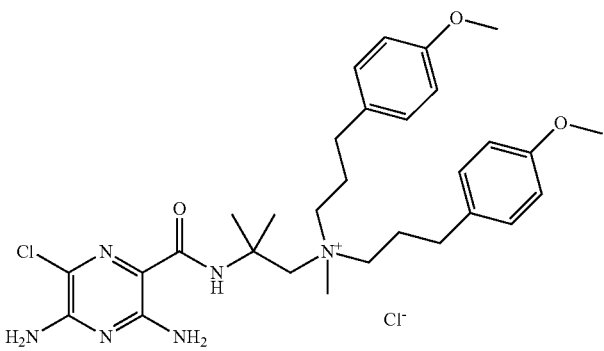{2-[(3,5-Diamino-6-chloro-pyrazine-2-carbonyl)-amino]-2-methyl-propyl}-bis-[3-(4-methoxy-phenyl)-propyl]-methyl-ammonium chloride | 569 | 1.35 | H | 0.51 |

Example 3

Intermediate 3.1: {1-[3-(4-Methoxy-phenyl)-propyl]-pyrrolidin-3-yl}-carbamic acid tert-butyl ester

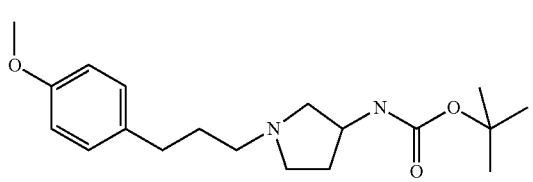 [SMILES: COc1ccc(CCCN2CCC(NC(=O)OC(C)(C)C)C2)cc1]

Pyrrolidin-3-yl-carbamic acid tert-butyl ester (250 mg, 1.35 mmol) and 1-(3-Bromo-propyl)-4-methoxy-benzene (375 µl, 2.15 mmol), potassium carbonate (550 mg, 4 mmol) and sodium iodide (50 mg, 0.33 mmol) are dissolved in acetonitril and stirred at reflux overnight. The reaction is filtered and purified by preparative HPLC-MS (MeOH/H2O+0.1% TFA). 2 M K$_2$CO$_3$ is added to relevant fractions to prevent cleavage of boc group during solvent evaporation. Methanol is removed under reduced pressure and the remaining aqueous phase is extracted with dichloromethane. The solvent is removed in vacuo. LC (method F): $t_R$=1.61 min; Mass spectrum (ESI$^+$): m/z=335 [M+H]$^+$.

Intermediate 3.2: {1-[3-(4-Methoxy-phenyl)-propyl]-piperidin-3-yl}-carbamic acid tert-butyl ester

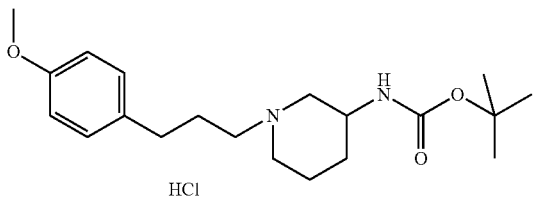 [SMILES: COc1ccc(CCCN2CCCC(NC(=O)OC(C)(C)C)C2)cc1 ; Cl]

The title compound is prepared from piperidine-3-yl-carbamic acid tert-butyl ester following a procedure analogous to that described in Intermediate 3.1. LC (method F): $t_R$=1.63 min; Mass spectrum (ESI$^+$): m/z=349 [M+H]$^+$.

Intermediate 3.3: 3-Amino-1-[3-(4-methoxy-phenyl)-propyl]-1-methyl-pyrrolidinium chloride hydrochloride

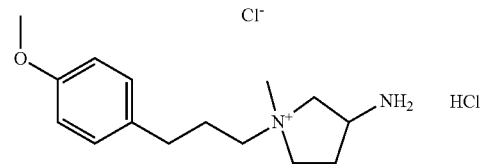 [SMILES: [Cl-] ; COc1ccc(CCC[N+]2(C)CCC(N)C2)cc1 ; Cl]

{1-[3-(4-Methoxy-phenyl)-propyl]-pyrrolidin-3-yl}-carbamic acid tert-butyl ester (264 mg, 0.789 mmol)) and methyliodide (100 µl, 1.58 mmol) are dissolved in acetone (8 ml) and stirred at 65° C. overnight. The solvent and methyliodine are removed under reduced pressure. Then 5 mL 1 M HCl is added and removed in vacuo to de-Boc and to form the HCl salt. LC (method F): $t_R$=0.98 min; Mass spectrum (ESI$^+$): m/z=249 [M]$^+$.

Intermediate 3.4: 3-Amino-1-(3-cyclohexyl-propyl)-1-[3-(4-methoxy-phenyl)-propyl]-piperidinium ditrifluoroacetate

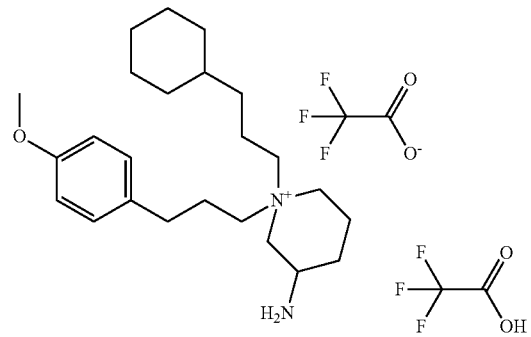 [SMILES: COc1ccc(CCC[N+]2(CCCC3CCCCC3)CCCC(N)C2)cc1 ; O=C([O-])C(F)(F)F ; O=C(O)C(F)(F)F]

{1-[3-(4-Methoxy-phenyl)-propyl]-pyrrolidin-3-yl}-carbamic acid tert-butyl ester (73 mg, 0.21 mmol)), 3-cyclohexyl-propylchloride (127 µl, 0.76 mmol), potassium carbonate (105 mg, 0.76 mmol) and sodium iodide (100 mg 0.67 mmol) in acetonitrile (2 ml) are heated under reflux for 4 days. The resulting mixture is purified by preparative HPLC-MS (MeOH/H2O+0.1% TFA). The residue is dissolved in dichloromethane (1 ml) and TFA (1 ml), stirred at room temperature overnight and concentrated in vacuo. LC (method G): $t_R$=1. min; Mass spectrum (ESP): m/z=373 [M]$^+$.

Table of analoges:

| Intermediate | Structure and name | ESI+ (M + H)+ | Rt | HPLC method |
|---|---|---|---|---|
| 3.5 | 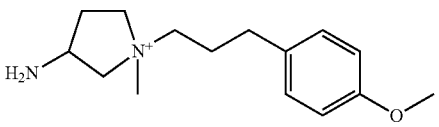<br>3-Amino-1-[3-(4-methoxy-phenyl)-propyl]-1-methyl-pyrrolidinium chloride hydrochloride | 249 | 0.98 | F |
| 3.6 | 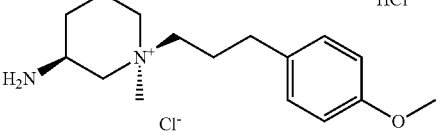<br>3-Amino-1-[3-(4-methoxy-phenyl)-propyl]-1-methyl-piperidinium chloride hydrochloride | 263 | 1.60 | F |
| 3.7 | 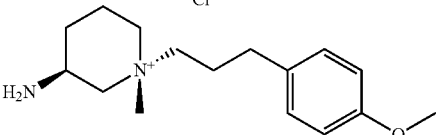<br>3-Amino-1-[3-(4-methoxy-phenyl)-propyl]-1-methyl-piperidinium chloride hydrochloride | 263 | 1.67 | F |
| 3.8 | 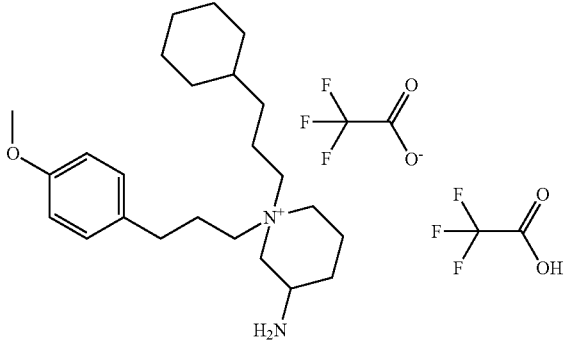<br>3-Amino-1-(3-cyclohexyl-propyl)-1-[3-(4-methoxy-phenyl)-propyl]-piperidinium ditrifluoroacetate | 373 | n.d. | G |
| 3.9 | 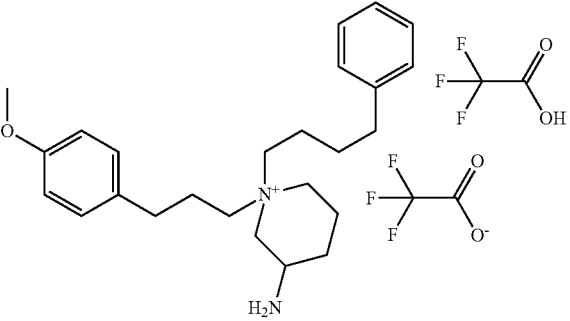<br>3-Amino-1-(4-phenyl-butyl)-1-[3-(4-methoxy-phenyl)-propyl]-piperidinium ditrifluoroacetate | 381 | n.d. | G |

-continued

Table of analoges:

| Intermediate | Structure and name | ESI+ (M + H)+ | Rt | HPLC method |
|---|---|---|---|---|
| 3.10 | 3-Amino-1-(3-phenyl-propyl)-1-[3-(4-methoxy-phenyl)-propyl]-piperidinium ditrifluoroacetate | 367 | n.d. | G |
| 3.11 | 3-Amino-1-[3-(4-methoxy-phenyl)-propyl]-1-phenethyl-piperidinium ditrifluoroacetate | 353 | 0.89 | K |
| 3.12 | 3-Amino-1-benzyl-1-[3-(4-methoxy-phenyl)-propyl]-piperidinium ditrifluoroacetate | 339 | n.d. | G |
| 3.13 | 3-Amino-1-[3-(4-methoxy-phenyl)-propyl]-1-methyl-4-p-tolyl-pyrrolidinium chloride hydrochloride | 339 | 1.39 | F |

Example 3

3-[(3,5-Diamino-6-chloro-pyrazine-2-carbonyl)-amino]-1-[3-(4-methoxy-phenyl)-propyl]-1-methyl-pyrrolidinium chloride

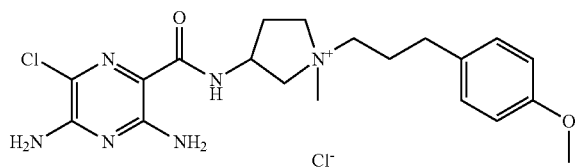 [SMILES: COc1ccc(CCC[N+]2(C)CCC(NC(=O)c3nc(Cl)c(N)nc3N)C2)cc1 ; [Cl-]]

3-Amino-1-[3-(4-methoxy-phenyl)-propyl]-1-methyl-pyrrolidinium chloride hydrochloride (65 mg, 0.2 mmol)), 3,5-Diamino-6-chloro-pyrazine-2-carboxylic acid (40 mg, 0.21 mmol) and N,N-Diisopropylethylamine (105 µl, 0.6 mmol) are dissolved in N,N-dimethylformamide (2 ml), 2-(1H-Benzotriazol-1-yl)-1,1,3,3-tetramethyluronium tetrafluoroborate (66 mg, 0.206 mmol) is added. The reaction is stirred at room temperature overnight. The resulting mixture is filtered through a pad of basic aluminum oxide. The pad is washed with N,N-dimethylformamide/methanol (9:1) and the combined filtrates are concentrated in vacuo. The product is purified by preparative HPLC-MS (MeOH/H2O+0.1% TFA). 1 mL 1 M HCl is added to form the chloride salt and the solvent is removed in vacuo. LC (method F): tR=1.39 min; Mass spectrum (ESI+): m/z=419 [M]$^+$. IC50=0.79 µM.

Table of analoges:

| Example | Structure and name | ESI+ (M+H)+ | Rt | HPLC method | IC50 [µM] |
|---|---|---|---|---|---|
| 3.1 | 3-[(3,5-Diamino-6-chloro-pyrazine-2-carbonyl)-amino]-1-[3-(4-methoxy-phenyl)-propyl]-1-methyl-piperidinium chloride | 434 | 1.71 | F | 0.75 |
| 3.2 | 3-[(3,5-Diamino-6-chloro-pyrazine-2-carbonyl)-amino]-1-[3-(4-methoxy-phenyl)-propyl]-1-methyl-piperidinium chloride | 434 | 1.50 | F | 0.07 |
| 3.3 | 1-(3-Cyclohexyl-propyl)-3-[(3,5-diamino-6-chloro-pyrazine-2-carbonyl)-amino]-1-[3-(4-methoxy-phenyl)-propyl]-piperidinium trifluoroacetate | 543 | 1.71 | G | 0.099 |

-continued

| | Table of analoges: | | | | |
|---|---|---|---|---|---|
| Example | Structure and name | ESI+ (M + H)+ | Rt | HPLC method | IC50 [μM] |
| 3.4 | 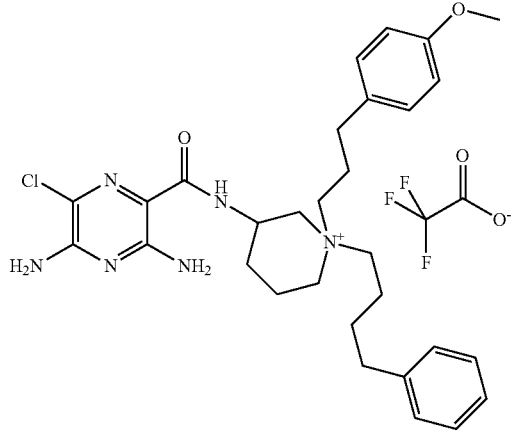<br>3-[(3,5-Diamino-6-chloro-pyrazine-2-carbonyl)-amino]-1-[3-(4-methoxy-phenyl)-propyl]-1-(4-phenyl-butyl)-piperidinium trifluoroacetate | 551 | 1.59 | G | 0.034 |
| 3.5 | 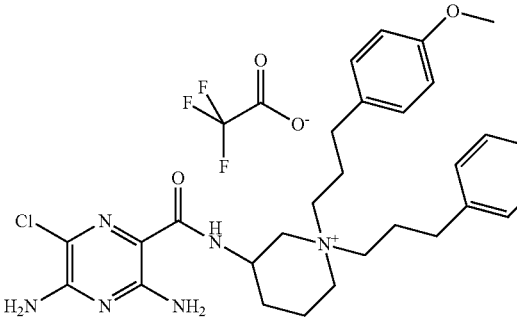<br>3-[(3,5-Diamino-6-chloro-pyrazine-2-carbonyl)-amino]-1-[3-(4-methoxy-phenyl)-propyl]-1-(3-phenyl-propyl)-piperidinium trifluoroacetate | 537 | 1.56 | G | 0.006 |
| 3.6 | 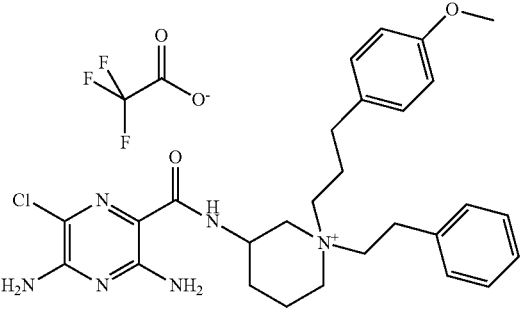<br>3-[(3,5-Diamino-6-chloro-pyrazine-2-carbonyl)-amino]-1-[3-(4-methoxy-phenyl)-propyl]-1-(2-phenyl-ethyl)-piperidinium trifluoroacetate | 523 | 1.50 | G | 0.06 |

Table of analoges:

| Example | Structure and name | ESI+ (M + H)+ | Rt | HPLC method | IC50 [μM] |
|---|---|---|---|---|---|
| 3.7 | 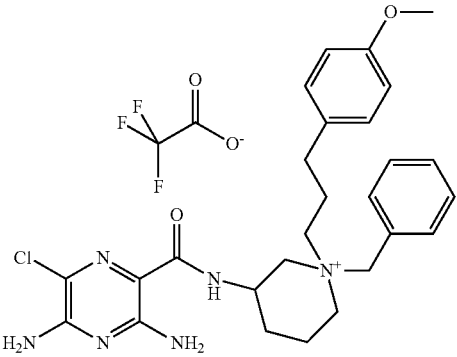 1-Benzyl-3-[(3,5-diamino-6-chloro-pyrazine-2-carbonyl)-amino]-1-[3-(4-methoxy-phenyl)-propyl]-piperidinium trifluoroacetate | 509 | 1.43 | G | 0.14 |
| 3.8 | 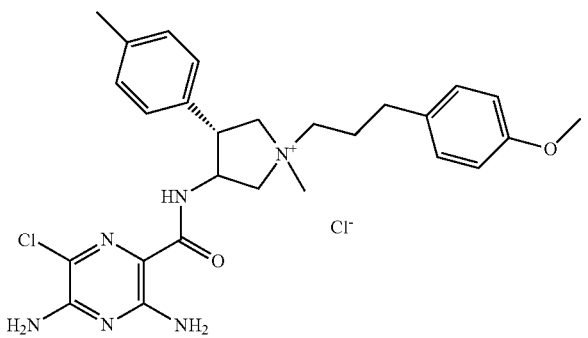 3-[(3,5-Diamino-6-chloro-pyrazine-2-carbonyl)-amino]-1-[3-(4-methoxy-phenyl)-propyl]-(R)-1-methyl-4-p-tolyl-pyrrolidinium chloride | 509 | 1.71 | F | 0.6 |

Example 4

Intermediate 4.1: 4-(3-Hydroxy-propyl)-benzoic acid methyl ester

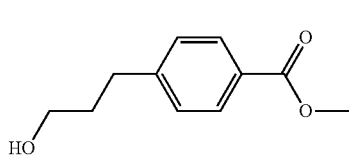

4-(2-Carboxy-ethyl)-benzoic acid methyl ester (5 g, 24 mmol) is dissolved in THF (50 ml), N,N-carbonyldiimidazole (4.25 g, 26.2 mmol) is added and stirred for 1 h at room temperature. Then sodium borohydride (1.9 g, 50 mmol) and water (10 ml) are added to the reaction mixture and stirred for additional 1 h. 1M HCl is added dropwise to the reaction mixture, extracted with ethyl acetate, the organic phase is dried and concentrated in vacuo. The residue is chromatographed on silica gel (dichloromethane/methanol) to afford the title compound. LC (method F): $t_R$=1.83 min; Mass spectrum (ESI+): m/z=195 [M+H]+.

Intermediate 4.2: 4-(3-Methanesulfonyloxy-propyl)-benzoic acid methyl ester

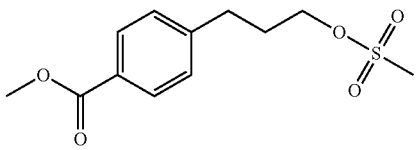

4-(3-Hydroxy-propyl)-benzoic acid methyl ester (1.27 g, 6.5 mmol) and triethylamine (1 ml, 7.1 mmol) are dissolved in dichloromethane (30 ml), cooled to −15° C., methanesulfonylchloride (510 μl, 6.5 mmol) is added and stirred at room temperature for 4 h. The reaction mixture is diluted with dichloromethane, washed with potassiumhydrogensulfoate solution and potassiumcarbonate solution, the organic phase is dried over Na$_2$SO$_4$ and concentrated in vacuo. LC (method F): $t_R$=1.88 min; Mass spectrum (ESP): m/z=295 [M+Na]+.

Intermediate 4.3: 3-tert-butoxycarbonylamino-1,1-bis-[3-(4-methoxycarbonyl-phenyl)-propyl]-piperidinium trifluoroacetate

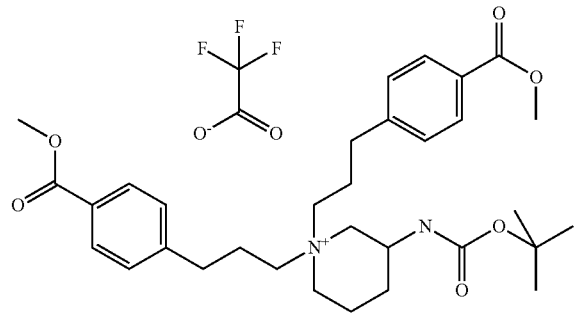 [SMILES: COC(=O)c1ccc(CCC[N+]2(CCCc3ccc(C(=O)OC)cc3)CCCC(NC(=O)OC(C)(C)C)C2)cc1 ; O=C([O-])C(F)(F)F]

4-(3-Methanesulfonyloxy-propyl)-benzoic acid methyl ester (800 mg, 2.9 mmol), piperidin-3-yl-carbamic acid tert-butyl ester (290 mg, 1.45 mmol), potassium carbonate (500 mg, 3.6 mmol) and sodium iodide (100 mg 0.67 mmol) in acetonitrile (20 ml) are heated under reflux for two days and evaporated. The is residue is taken up in dimethylsulfoxide (10 ml) and stirred at 90° C. for 5 h. The resulting mixture is purified by preparative HPLC-MS (MeOH/H2O+0.1% TFA). LC (method F): $t_R$=1.84 min; Mass spectrum (ESI$^+$): m/z=553 [M]$^+$.

Intermediate 4.4: 3-Amino-1,1-bis-[3-(4-methoxycarbonyl-phenyl)-propyl]-piperidinium chloride hydrochloride

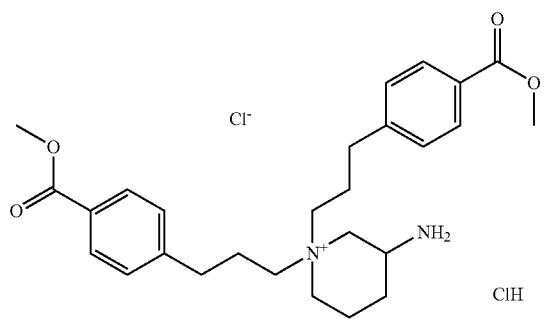 [SMILES: COC(=O)c1ccc(CCC[N+]2(CCCc3ccc(C(=O)OC)cc3)CCCC(N)C2)cc1 ; [Cl-] ; Cl]

3-tert-butoxycarbonylamino-1,1-bis-[3-(4-methoxycarbonyl-phenyl)-propyl]-piperidinium trifluoroacetate (200 mg, 0.3 mmol) is dissolved in dioxane (10 ml), a 4 M solution of HCl in dioxane (10 ml, 40 mmol) is added, stirred at room temperature overnight and concentrated in vacuo. LC (method F): $t_R$=1.49 min; Mass spectrum (ESI$^+$): m/z=453 [M]$^+$.

Example 4

3-[(3,5-Diamino-6-chloro-pyrazine-2-carbonyl)-amino]-1,1-bis-[3-(4-methoxycarbonylphenyl)-propyl]-piperidinium chloride

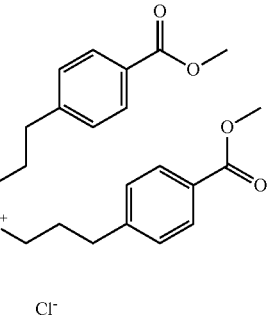

3-Amino-1,1-bis-[3-(4-methoxycarbonyl-phenyl)-propyl]-piperidinium chloride hydrochloride (158 mg, 0.3 mmol)), 3,5-Diamino-6-chloro-pyrazine-2-carboxylic acid (58 mg, 0.3 mmol) and N,N-Diisopropylethylamine (125 µl, 0.7 mmol) are dissolved in N,N-dimethylformamide (5 ml), 2-(1H-Benzotriazol-1-yl)-1,1,3,3-tetramethyluronium tetrafluoroborate (100 mg, 0.3 mmol) is added. The reaction is stirred at room temperature overnight and purified by preparative HPLC-MS (MeOH/H2O+0.1% TFA). 0.3 mL 1 M HCl is added to form chloride salt and solvent removed in vacuo. LC (method F): $t_R$=1.71 min; Mass spectrum (ESI$^+$): m/z=623 [M]$^+$. IC50=0.34 µM.

Example 4.1

1,1-Bis-[3-(4-carboxy-phenyl)-propyl]-3-[(3,5-diamino-6-chloro-pyrazine-2-carbonyl)amino]-piperidinium

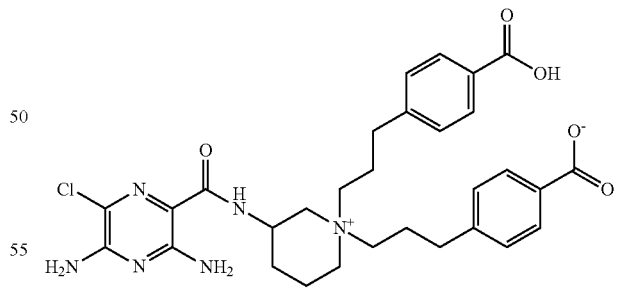

3-[(3,5-Diamino-6-chloro-pyrazine-2-carbonyl)-amino]-1,1-bis-[3-(4-methoxycarbonyl-phenyl)-propyl]-piperidinium chloride (65 mg, 0.1 mmol) is dissolved in methanol (3 ml) and 1N sodium hydroxide (2 ml, 2 mmol) and stirred at room temperature overnight and additional 2 h at 50° C. The reaction is acidified with 1M HCl and purified by preparative HPLC-MS (MeOH/H2O+0.1% NH4OH). LC (method F): $t_R$=1.48 min; Mass spectrum (ESI$^+$): m/z=595 [M]$^+$. IC50=0.35 µM

Example 4.2

3-[(3,5-Diamino-6-chloro-pyrazine-2-carbonyl)-amino]-1,1-bis-[3-(4-{2-[2-(2-hydroxyethoxy)-ethoxy)]-ethylcarbamoyl}-phenyl)-propyl]-piperidinium chloride

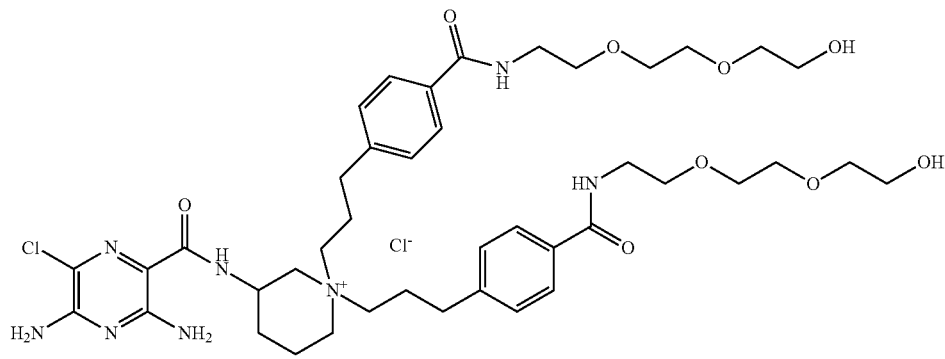 [SMILES: Nc1nc(N)c(C(=O)NC2CCC[N+](CCCc3ccc(C(=O)NCCOCCOCCO)cc3)(CCCc3ccc(C(=O)NCCOCCOCCO)cc3)C2)nc1Cl ; [Cl-]]

1,1-Bis-[3-(4-carboxy-phenyl)-propyl]-3-[(3,5-diamino-6-chloro-pyrazine-2-carbonyl)-amino]-piperidinium (24 mg, 0.04 mmol), 2-[2-(2-Amino-ethoxy)-ethoxy]-ethanol (15 mg, 0.1 mmol) and N,N-Diisopropylethylamine (35 µl, 0.2 mmol) are dissolved in N,N-dimethylformamide (2 ml), 2-(1H-Benzotriazol-1-yl)-1,1,3,3-tetramethyluronium tetrafluoroborate (30 mg, 0.09 mmol) is added. The reaction is stirred at room temperature overnight and purified by preparative HPLC-MS (MeOH/H2O+0.1% TFA). 0.1 mL 1 M HCl is added to form chloride salt and solvent removed in vacuo. LC (method F): $t_R$=1.22 min; Mass spectrum (ESI$^+$): m/z=857 [M]$^+$. IC50=0.76 µM

Example 5

Intermediate 5.1: 4-[3-(3-tert-Butoxycarbonylamino-piperidin-1-yl)-propyl]-benzoic acid methyl ester

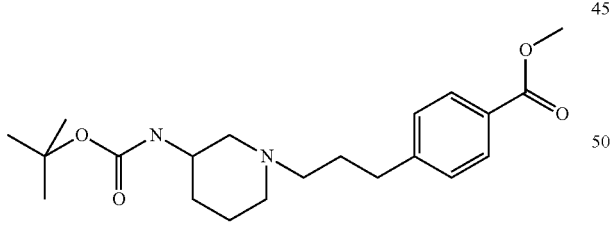

4-(3-Methanesulfonyloxy-propyl)-benzoic acid methyl ester (800 mg, 2.9 mmol), piperidin-3-yl-carbamic acid tert-butyl ester (290 mg, 1.45 mmol), potassium carbonate (500 mg, 3.6 mmol) and sodium iodide (100 mg 0.67 mmol) in acetonitrile (20 ml) are heated under reflux for two days and evaporated. The residue is taken up in dimethylsulfoxide (10 ml) and stirred at 90° C. for 5 h. The resulting mixture is purified by preparative HPLC-MS (MeOH/H2O+0.1% TFA). Potassiumcarbonate solution is added to the product, extracted with ethyl acetate, the organic phase is dried over Na$_2$SO$_4$ and concentrated in vacuo. LC (method F): $t_R$=1.66 min; Mass spectrum (ESI$^+$): m/z=377 [M+H]$^+$.

Intermediate 5.2: 3-tert-Butoxycarbonylamino-1-[3-(4-methoxycarbonyl-phenyl)-propyl]-1-[3-(4-methoxy-phenyl)-propyl]-piperidinium trifluoroacetate 4-[3-(3-tert-Butoxycarbonylamino-piperidin-1-yl)-propyl]-benzoic acid methyl ester (360 mg, 0.96 mmol), 1-(3-Bromo-propyl)-4-methoxy-benzene (360 µl, 2 mmol), potassium carbonate (150 mg, 1.08 mmol) and sodium iodide (100 mg, 0.67 mmol) are dissolved in acetonitril (10 ml) and stirred at reflux for 3 days. The reaction is filtered and purified by preparative HPLC-MS (MeOH/H2O+0.1% TFA). LC (method F): $t_R$=1.85 min; Mass spectrum (ESI$^+$): m/z=525 [M-P]$^+$.

Intermediate 5.3

3-Amino-1-[3-(4-methoxycarbonyl-phenyl)-propyl]-1-[3-(4-methoxy-phenyl)-propyl]-piperidinium chloride hydrochloride

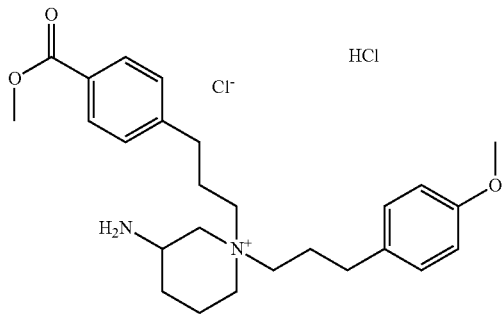 [SMILES: COC(=O)c1ccc(CCC[N+]2(CCCc3ccc(OC)cc3)CCCC(N)C2)cc1 ; [Cl-] ; Cl]

3-tert-Butoxycarbonylamino-1-[3-(4-methoxycarbonyl-phenyl)-propyl]-1-[3-(4-methoxy-phenyl)propyl]-piperidinium trifluoroacetate (525 mg, 0.82 mmol) is dissolved in dioxane (10 ml), a 4 M solution of HCl in dioxane (10 ml, 40 mmol) is added, stirred at room temperature for 2 h and concentrated in vacuo. LC (method 004_CC_ZQ7): $t_R$=1.80 min; Mass spectrum (ESI$^+$): m/z=425 [M]$^+$.

Example 5

3-[(3,5-Diamino-6-chloro-pyrazine-2-carbonyl)-amino]-1-[3-(4-methoxycarbonyl-phenyl)propyl]-1-[3-(4-methoxy-phenyl)-propyl]-piperidinium chloride

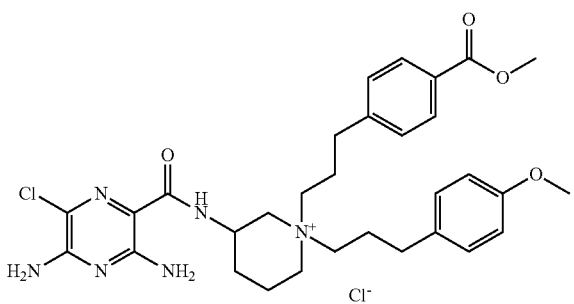 [SMILES: COC(=O)c1ccc(CCC[N+]2(CCCc3ccc(OC)cc3)CCCC(NC(=O)c3nc(Cl)c(N)nc3N)C2)cc1 ; [Cl-]]

3-Amino-1-[3-(4-methoxycarbonyl-phenyl)-propyl]-1-[3-(4-methoxy-phenyl)-propyl]-piperidinium chloride hydrochloride (410 mg, 0.824 mmol)), 3,5-Diamino-6-chloro-pyrazine-2-carboxylic acid (160 mg, 0.84 mmol) and N,N-Diisopropylethylamine (400 µl, 2.3 mmol) are dissolved in N,N-dimethylformamide (5 ml), 2-(1H-Benzotriazol-1-yl)-1,1,3,3-tetramethyluronium tetrafluoroborate (265 mg, 0.825 mmol) is added. The reaction is stirred at room temperature for 1 h and purified by preparative HPLC-MS (MeOH/H2O+0.1% TFA). 0.8 mL 1 M HCl is added to form chloride salt and solvent removed in vacuo. LC (method F): $t_R$=1.75 min; Mass spectrum (ESI$^+$): m/z=595[M]$^+$. IC50=0.038 µM

Example 5.1

1-[3-(4-Carboxy-phenyl)-propyl]-3-[(3,5-diamino-6-chloro-pyrazine-2-carbonyl)-amino]-1-[3-(4-methoxy-phenyl)-propyl]-piperidinium

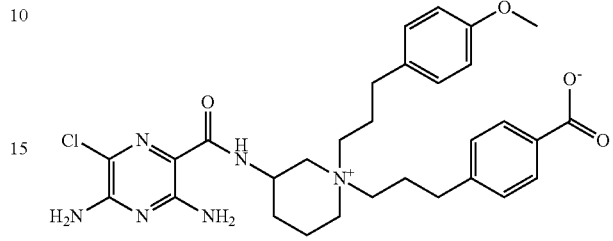

3-[(3,5-Diamino-6-chloro-pyrazine-2-carbonyl)-amino]-1-[3-(4-methoxycarbonyl-phenyl)-propyl]-1-[3-(4-methoxy-phenyl)-propyl]-piperidinium chloride (460 mg, 0.73 mmol)) is dissolved in methanol (4 ml) and 1N sodium hydroxide (4 ml, 4 mmol) and stirred at room temperature overnight and additional 2 h at 50° C. The reaction is acidified with 1M HCl and purified by preparative HPLC-MS (MeOH/H2O+0.1% NH4OH). LC (method F): $t_R$=1.61 min; Mass spectrum (ESI$^+$): m/z=581[M]$^+$. IC50=0.11 µM

Example 5.2

3-[(3,5-Diamino-6-chloro-pyrazine-2-carbonyl)-amino]-1-{3-[4-(methoxycarbonylmethylcarbamoyl)-phenyl]-propyl}-1-[3-(4-methoxy-phenyl)-propyl]-piperidinium chloride

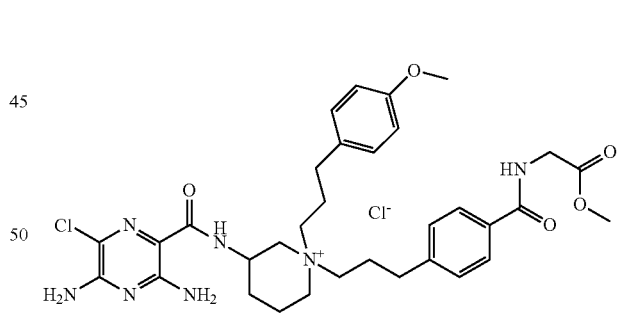

1-[3-(4-Carboxy-phenyl)-propyl]-3-[(3,5-diamino-6-chloro-pyrazine-2-carbonyl)-amino]-1-[3-(4-methoxy-phenyl)-propyl]-piperidinium (40 mg, 0.069 mmol), glycine methylester hydrochloride (10 mg, 0.08 mmol) and N,N-Diisopropylethylamine (25 µl, 0.2 mmol) are dissolved in N,N-dimethylformamide (2 ml), 2-(1H-Benzotriazol-1-yl)-1,1,3,3-tetramethyluronium tetrafluoroborate (25 mg, 0.078 mmol) is added. The reaction is stirred at room temperature for 2 h and purified by preparative HPLC-MS (MeOH/H2O+0.1% TFA). 0.07 mL 1 M HCl is added to form chloride salt and solvent removed in vacuo. LC (method H): $t_R$=1.35 min; Mass spectrum (ESI$^+$): m/z=652 [M]$^+$. IC50=0.042 µM Table of analoges:

| Ex. | Structure and name | ESI+ (M)+ | Rt | HPLC method | IC50 [µM] |
|---|---|---|---|---|---|
| 5.3 | 1-(3-{4-[Bis-(3-dimethylamino-propyl)-carbamoyl]-phenyl}-propyl)-3-[(3,5-diamino-6-chloro-pyrazine-2-carbonyl)-amino]-1-[3-(4-methoxy-phenyl)-propyl]-piperidinium chloride dihydrochloride | (M + H) ++375 | 1.10 | H | 0.055 |
| 5.4 | 3-[(3,5-Diamino-6-chloro-pyrazine-2-carbonyl)-amino]-1-[3-(4-methoxy-phenyl)-propyl]-1-{3-[4-(3-sulfo-propylcarbamoyl)-phenyl]-propyl}-piperidinium chloride | 702 | 1.42 | H | 0.26 |
| 5.5 | 3-[(3,5-Diamino-6-chloro-pyrazine-2-carbonyl)-amino]-1-[3-(4-{2-[2-(2-hydroxy-ethoxy)-ethoxy]-ethylcarbamoyl}-phenyl)-propyl]-1-[3-(4-methoxy-phenyl)-propyl]-piperidinium chloride | 712 | 1.32 | H | 0.07 |
| 5.6 | 1-[3-(4-Carbamoyl-phenyl)-propyl]-3-[(3,5-diamino-6-chloro-pyrazine-2-carbonyl)-amino]-1-[3-(4-methoxy-phenyl)-propyl]-piperidinium chloride | 580 | 1.30 | H | 0.025 |

Table of analoges:

| Ex. | Structure and name | ESI+ (M)+ | Rt | HPLC method | IC50 [μM] |
|---|---|---|---|---|---|
| 5.7 | 3-[(3,5-Diamino-6-chloro-pyrazine-2-carbonyl)-amino]-1-{3-[4-(3-dimethylamino-propylcarbamoyl)-phenyl]-propyl}-1-[3-(4-methoxy-phenyl)-propyl]-piperidinium chloride hydrochloride | 665 | 1.15 | H | 0.02 |
| 5.8 | 3-[(3,5-Diamino-6-chloro-pyrazine-2-carbonyl)-amino]-1-{3-[4-(2-methoxycarbonyl-ethylcarbamoyl)-phenyl]-propyl}-1-[3-(4-methoxy-phenyl)-propyl]-piperidinium chloride | 667 | 1.38 | H | 0.024 |

Example 5.9

1-{3-[4-(Carboxymethyl-carbamoyl)-phenyl]-propyl}-3-[(3,5-diamino-6-chloro-pyrazine-2-carbonyl)-amino]-1-[3-(4-methoxy-phenyl)-propyl]-piperidinium chloride

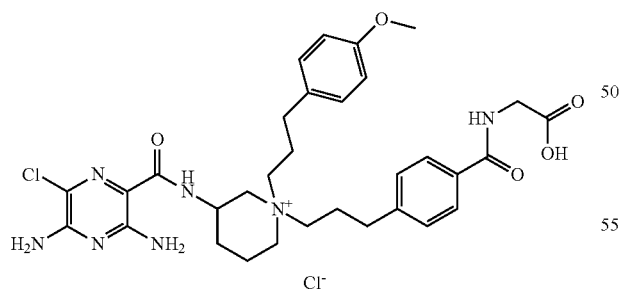

3-[(3,5-Diamino-6-chloro-pyrazine-2-carbonyl)-amino]-1-{3-[4-(methoxycarbonylmethyl-carbamoyl)phenyl]-propyl}-1-[3-(4-methoxy-phenyl)-propyl]-piperidinium chloride (20 mg, 0.029 mmol)) is dissolved in methanol (1 ml) and 1N sodium hydroxide (0.2 ml, 0.2 mmol) and stirred at room temperature overnight. The reaction is acidified with 1M HCl and purified by preparative HPLC-MS (MeOH/H2O+0.1% NH4OH). 0.03 mL 1 M HCl is added to form chloride salt and solvent removed in vacuo. LC (method F): $t_R$=1.53 min; Mass spectrum (ESI$^+$): m/z=638 [M]$^+$. IC50=0.14 nM.

Example 5.10

1-{3-[4-(Carboxyethyl-carbamoyl)-phenyl]-propyl}-3-[(3,5-diamino-6-chloro-pyrazine-2-carbonyl)-amino]-1-[3-(4-methoxy-phenyl)-propyl]-piperidinium chloride The title compound is prepared from 3-[(3,5-Diamino-6-chloro-pyrazine-2-carbonyl)-amino]-1-{3-[4-(2-methoxycarbonyl-ethylcarbamoyl)-phenyl]-propyl}-1-[3-(4-methoxy-phenyl)-propyl]-piperidinium chloride following a procedure analogous to that described in Example 5.9. LC (F): $t_R$=1.53 min; Mass is spectrum (ESI$^+$): m/z=652 [M]$^+$. IC50=0.15

Example 6

Intermediate 6.1: 3-tert-Butoxycarbonylamino-1,1-bis-[3-(4-methoxy-phenyl)-propyl]-piperidinium trifluoroacetate

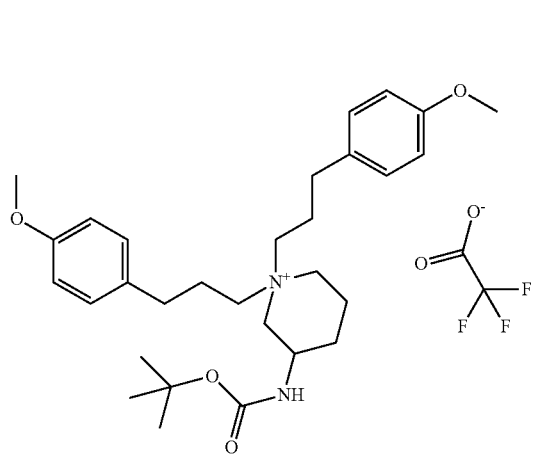

Piperidin-3-yl-carbamic acid tert-butyl ester (1 g, 5 mmol) and 1-(3-Bromo-propyl)-4-methoxy-benzene (2.3 ml, 13 mmol), potassium carbonate (1.6 g, 11.6 mmol) and sodium iodide (1.3 g, 8.7 mmol) are dissolved in acetonitril (40 ml) and stirred at reflux for 5 days. The solvent is removed under vacuo and the product purified by preparative HPLC-MS (MeOH/H2O+0.1% TFA). LC (method F): $t_R$=1.89 min; Mass spectrum (ESI$^+$): m/z=497 [M]$^+$.

Intermediate 6.2: 3-Amino-1,1-bis-[3-(4-hydroxy-phenyl)-propyl]-piperidinium bromide hydrobromide

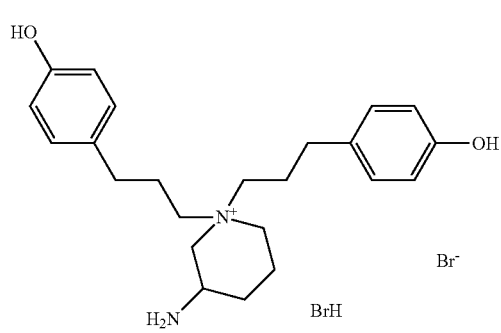 [SMILES: NC1CCC[N+](CCCc2ccc(O)cc2)(CCCc2ccc(O)cc2)C1 ; Br ; [Br-]]

3-tert-Butoxycarbonylamino-1,1-bis-[3-(4-methoxy-phenyl)-propyl]-piperidinium trifluoroacetate (2.76 g, 4.5 mmol) in dichloromethane (40 ml) are cooled to −15° C., 1 M borontribromide solution in dichloromethane (27 ml, 27 mmol) is added dropwise, the reaction is allowed to warm to room temperature and stirred overnight. Then methanol (20 ml) is added dropwise and the reaction mixture is evaporated. LC (method G): $t_R$=0.77 min; Mass spectrum (ESP): m/z=369 [M]$^+$.

Intermediate 6.3: 3-tert-Butoxycarbonylamino-1,1-bis-[3-(4-hydroxy-phenyl)-propyl]-piperidinium chloride

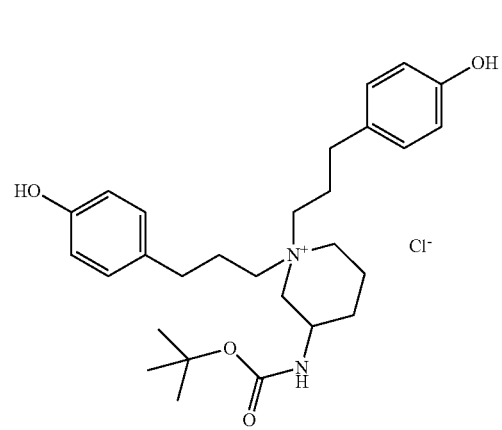 [SMILES: CC(C)(C)OC(=O)NC1CCC[N+](CCCc2ccc(O)cc2)(CCCc2ccc(O)cc2)C1 ; [Cl-]]

A solution of di-tert.butyl dicarbonate (1.1 g, 5 mmol) in dichloromethane (10 ml) is added dropwise to a solution of 3-Amino-1,1-bis-[3-(4-hydroxy-phenyl)-propyl]-piperidinium bromide hydrobromide (2.97 g, 5 mmol) and triethylamine (1.5 ml, 10.8 mmol) in methanol (20 ml) at 0° C. and stirred at this temperature for 30 min. The reaction is allowed to warm to room temperature, stirred overnight and concentrated in vacuo. The residue is triturated with a mixture of ethyl acetate and 0.1 M HCl, dissolved in methanol and concentrated in vacuo. LC (method L): $t_R$=1.07 min; Mass spectrum (ESI$^+$): m/z=469 [M]$^+$.

Intermediate 6.4: 3-tert-Butoxycarbonylamino-1,1-bis-[3-(4-methoxycarbonylmethoxy-phenyl)-propyl]-piperidinium chloride

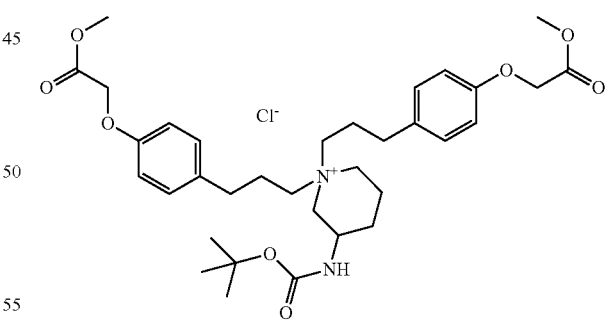

Bromo-acetic acid methylester is added to a suspension of 3-tert-Butoxycarbonylamino-1,1-bis-[3-(4-hydroxy-phenyl)-propyl]-piperidinium chloride (550 mg, 1.09 mmol) and potassium carbonate (500 mg, 3.6 mmol) in DMF (5 ml), stirred for 2 h at room temperature and concentrated in vacuo. Water is added to the residue and extracted with dichloromethane. The organic phase is washed with water, dried over Na$_2$SO$_4$ and concentrated in vacuo. LC (method WO001_002): $t_R$=1.73 min; Mass spectrum (ESI$^+$): m/z=613 [M]$^+$.

Intermediate 6.5: 3-Amino-1,1-bis-[3-(4-methoxy-carbonylmethoxy-phenyl)-propyl]-piperidinium chloride hydrochloride

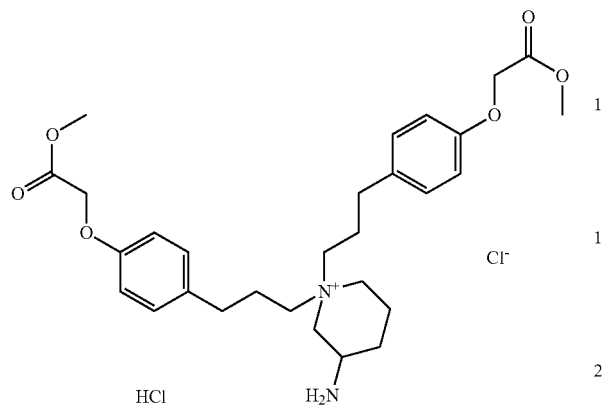

3-tert-Butoxycarbonylamino-1,1-bis-[3-(4-methoxycarbonylmethoxy-phenyl)-propyl]-piperidinium chloride (707 mg, 1.09 mmol) is dissolved in dichloromethane (1 ml) and trifluoroacetic acid (1 ml) and stirred at room temperature overnight. The mixture is evaporated, dissolved in acetonitrile and 1 M HCl (5 ml) and evaporated again. LC (method L): $t_R$=0.95 min; Mass spectrum (ESI$^+$): m/z=513 [M]$^+$.

Example 6

3-[(3,5-Diamino-6-chloro-pyrazine-2-carbonyl)-amino]-1,1-bis-[3-(4-methoxycarbonylmethoxy-phenyl)-propyl]-piperidinium trifluoroacetate

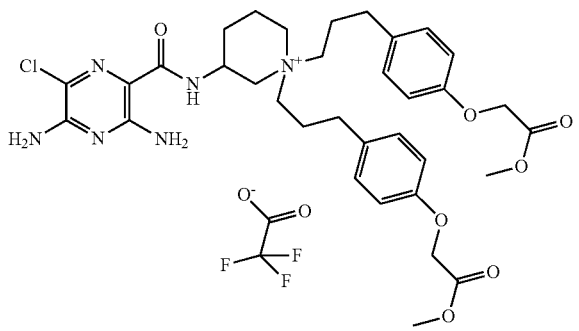 [SMILES: COC(=O)COc1ccc(CCC[N+]2(CCCc3ccc(OCC(=O)OC)cc3)CCCC(NC(=O)c3nc(Cl)c(N)nc3N)C2)cc1 ; O=C([O-])C(F)(F)F]

3-Amino-1,1-bis-[3-(4-methoxycarbonylmethoxy-phenyl)-propyl]-piperidinium chloride hydrochloride (60 mg, 0.1 mmol), 3,5-Diamino-6-chloro-pyrazine-2-carboxylic acid (22 mg, 0.115 mmol) and N,N-Diisopropylethylamine (75 µl, 0.43 mmol) are dissolved in N,N-dimethylformamide (2 ml), 2-(1H-Benzotriazol-1-yl)-1,1,3,3-tetramethyluronium tetrafluoroborate (34 mg, 0.106 mmol) is added. The reaction is stirred at room temperature overnight and purified by preparative HPLC-MS (MeOH/H2O+0.1% TFA). LC (method L): $t_R$=1.12 min; Mass spectrum (ESI$^+$): m/z=683 [M]$^+$. IC50=0.02 µM.

Example 6.1

1,1-Bis-[3-(4-carboxymethoxy-phenyl)-propyl]-3-[(3,5-diamino-6-chloro-pyrazine-2-carbonyl)-amino]-piperidinium chloride

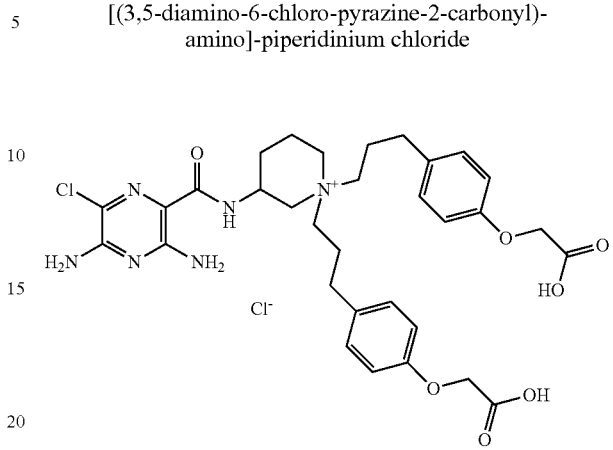

3-[(3,5-Diamino-6-chloro-pyrazine-2-carbonyl)-amino]-1,1-bis-[3-(4-methoxycarbonylmethoxy-phenyl)propyl]-piperidinium trifluoroacetate (860 mg, 1.08 mmol)) is dissolved in methanol (20 ml) and 1N sodium hydroxide (10 ml, 10 mmol) and stirred at room temperature for 4 h. The reaction is acidified with 1M HCl and purified by preparative HPLC-MS (MeOH/H2O+0.1% NH4OH). 2 mL 1 M HCl is added to form chloride salt and solvent removed in vacuo. LC (method L)): $t_R$=1.01 min; Mass spectrum (ESI$^+$): m/z=655 [M]$^+$. IC50>1 µM.

Example 6.2

(S)-1,1-Bis-[3-(4-carboxymethoxy-phenyl)-propyl]-3-[(3,5-diamino-6-chloro-pyrazine-2-carbonyl)-amino]-piperidinium chloride

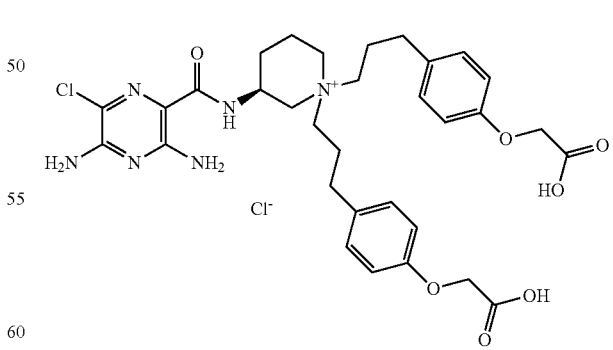

The title compound is prepared from (S)-piperidin-3-yl-carbamic acid tert-butyl ester following the same procedure analogous to that described for the racemate. The title compound and all intermediates have the same physicochemical properties as the intermediates of the racemic derivatives.

Example 6.3

3-[(3,5-Diamino-6-chloro-pyrazine-2-carbonyl)-amino]-1,1-bis-{3-[4-({2-[2-(2-hydroxyethoxy)-ethoxy]-ethylcarbamoyl}-methoxy)-phenyl]-propyl}-piperidinium trifluoroacetate

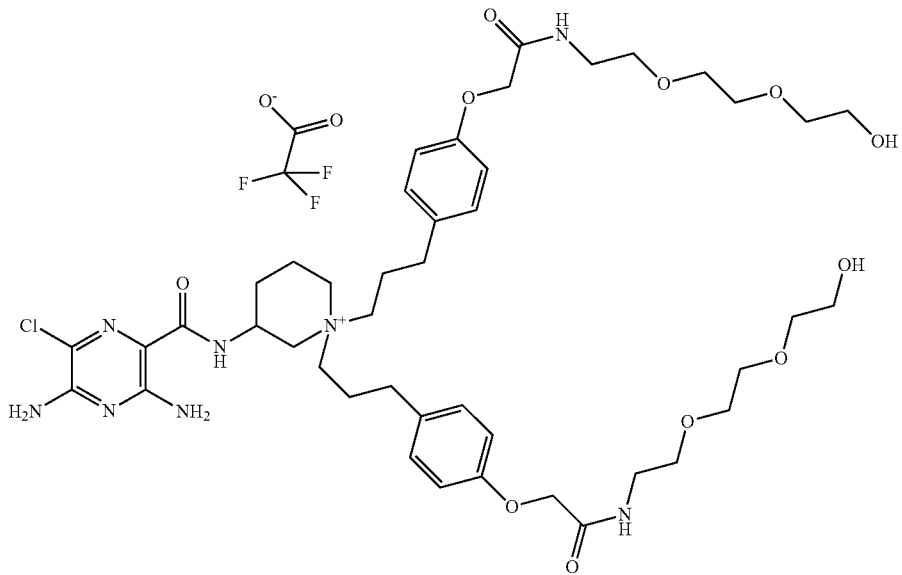 [SMILES: Nc1nc(N)c(C(=O)NC2CCC[N+](CCCc3ccc(OCC(=O)NCCOCCOCCO)cc3)(CCCc3ccc(OCC(=O)NCCOCCOCCO)cc3)C2)nc1Cl ; O=C([O-])C(F)(F)F]

1,1-Bis-[3-(4-carboxymethoxy-phenyl)-propyl]-3-[(3,5-diamino-6-chloro-pyrazine-2-carbonyl)-amino]-piperidinium chloride (42 mg, 0.06 mmol), 2-[2-(2-Aminoethoxy)-ethoxy]-ethanol (45 mg, 0.3 mmol) and N,N-Diisopropylethylamine (50 µl, 0.29 mmol) are dissolved in N,N-dimethylformamide (2 ml), 2-(1H-Benzotriazol-1-yl)-1,1,3,3-tetramethyluronium tetrafluoroborate (40 mg, 0.125 mmol) is added. The reaction is stirred at room temperature overnight and purified by preparative HPLC-MS (MeOH/H2O+0.1% TFA). LC (method L): $t_R$=1.01 min; Mass spectrum (ESI$^+$): m/z=459 [M]$^{++}$. IC50=0.103.

Table of analoges:

| Ex. | Structure and name | ESI+ (M)+ | HPLC Rt | method | IC50 [µM] |
|---|---|---|---|---|---|
| 6.4 | 1,1-Bis-[3-(4-carbamoylmethoxy-phenyl)-propyl]-3-[(3,5-diamino-6-chloro-pyrazine-2-carbonyl)-amino]-piperidinium trifluoroacetate | 653 | 0.93 | L | 0.072 |

Table of analoges:

| Ex. | Structure and name | ESI+ (M)+ | Rt | HPLC method | IC50 [μM] |
|---|---|---|---|---|---|
| 6.5 | 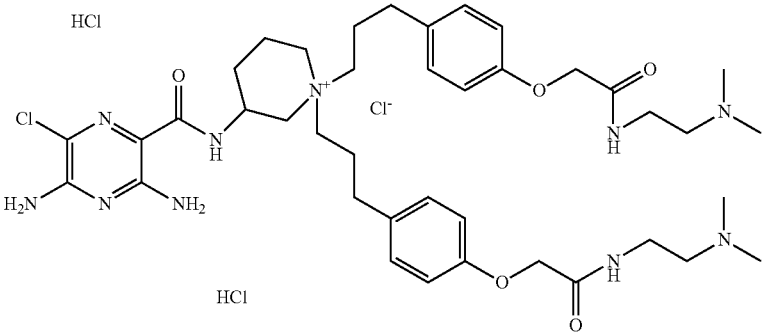<br>3-[(3,5-Diamino-6-chloro-pyrazine-2-carbonyl)-amino]-1,1-bis-(3-{4-[(2-dimethylamino-ethylcarbamoyl)-methoxy]-phenyl}-propyl)-piperidinium chloride dihydrochloride | 795 | 0.81 | L | 0.050 |
| 6.6 | 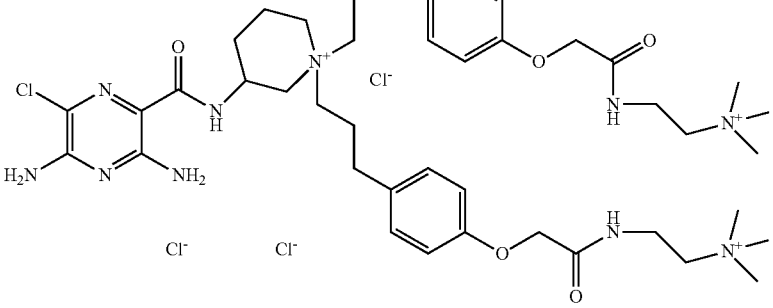<br>3-[(3,5-Diamino-6-chloro-pyrazine-2-carbonyl)-amino]-1,1-bis-(3-{4-[(2-trimethylammonium-ethylcarbamoyl)-methoxy]-phenyl}-propyl)-piperidinium trichloride | 413 (M++) | 0.79 | L | 0.068 |
| 6.7 | 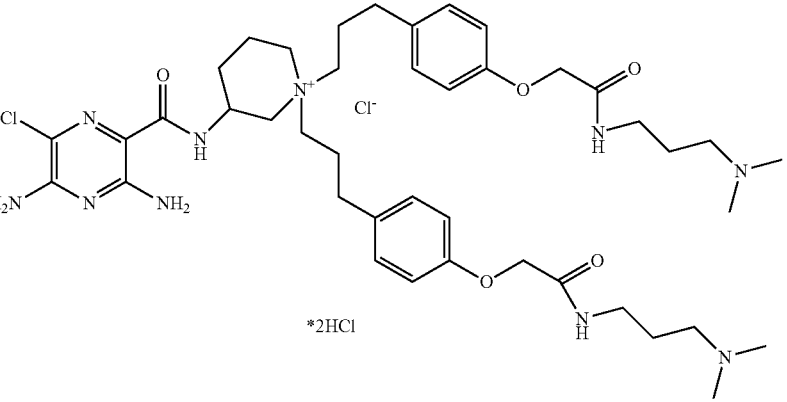<br>3-[(3,5-Diamino-6-chloro-pyrazine-2-carbonyl)-amino]-1,1-bis-(3-{4-[(3-dimethylamino-propylcarbamoyl)-methoxy]-phenyl}-propyl)-piperidinium chloride dihydrochloride | 412 (M++) | 0.82 | L | 0.031 |

-continued

Table of analoges:

| Ex. | Structure and name | ESI+ (M)+ | Rt | HPLC method | IC50 [µM] |
|---|---|---|---|---|---|
| 6.8 | 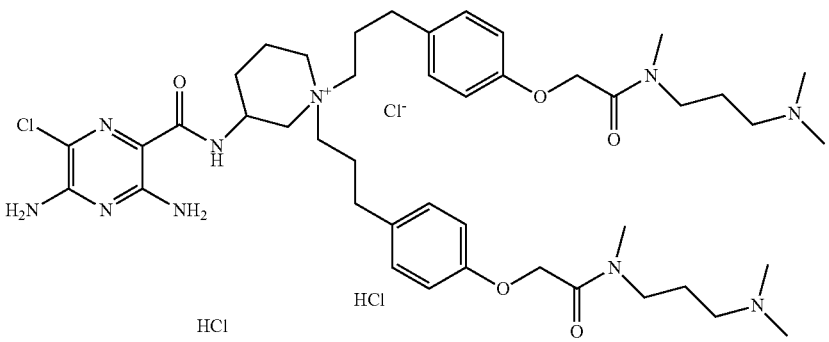<br>3-[(3,5-Diamino-6-chloro-pyrazine-2-carbonyl)-amino]-1,1-bis-[3-(4-{[(3-dimethylamino-propyl)-methyl-carbamoyl]-methoxy}-phenyl)-propyl]-piperidinium chloride dihydrochloride | 426 (M++) | 0.83 | L | 0.041 |
| 6.9 | 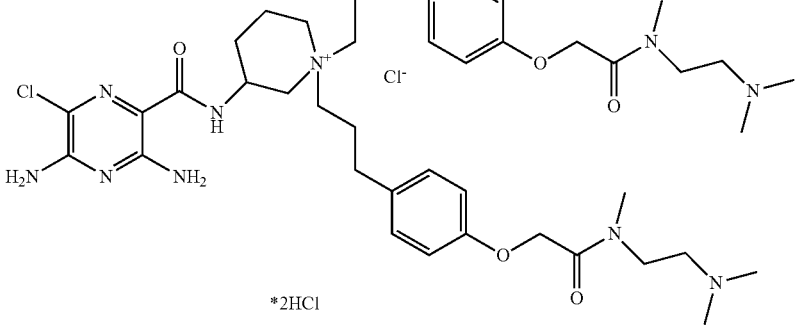<br>3-[(3,5-Diamino-6-chloro-pyrazine-2-carbonyl)-amino]-1,1-bis-[3-(4-{[(2-dimethylamino-ethyl)-methyl-carbamoyl]-methoxy}-phenyl)-propyl]-piperidinium chloride dihydrochloride | 412 (M++) | 0.81 | L | 0.065 |
| 6.10 | 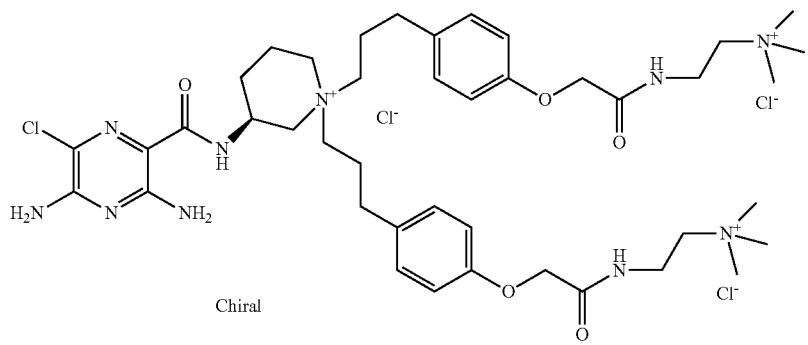<br>(S)-3-[(3,5-Diamino-6-chloro-pyrazine-2-carbonyl)-amino]-1,1-bis-(3-{4-[(2-trimethyl-ammonium-ethylcarbamoyl)-methoxy]-phenyl}-propyl)-piperidinium trichloride | 275 (M+++) | 0.79 | L | 0.068 |

Table of analoges:

| Ex. | Structure and name | ESI+ (M)+ | Rt | HPLC method | IC50 [μM] |
|---|---|---|---|---|---|
| 6.11 | 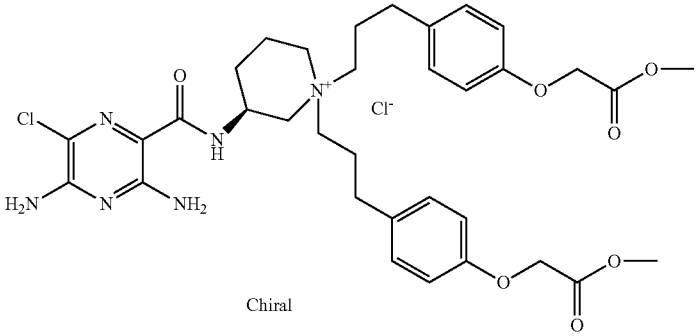<br>(S)-3-[(3,5-Diamino-6-chloro-pyrazine-2-carbonyl)-amino]-1,1-bis-[3-(4-methoxycarbonylmethoxy-phenyl)-propyl]-piperidinium chloride | 683 | 1.12 | L | 0.045 |
| 6.12 | 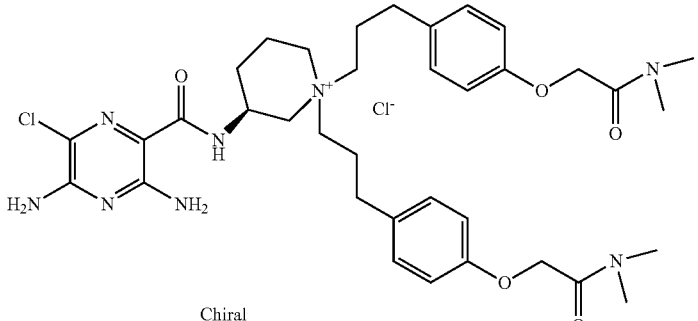<br>(S)-3-[(3,5-Diamino-6-chloro-pyrazine-2-carbonyl)-amino]-1,1-bis-[3-(4-dimethylcarbamoylmethoxy-phenyl)-propyl]-piperidinium chloride | 709 | 1.03 | L | 0.134 |
| 6.13 | 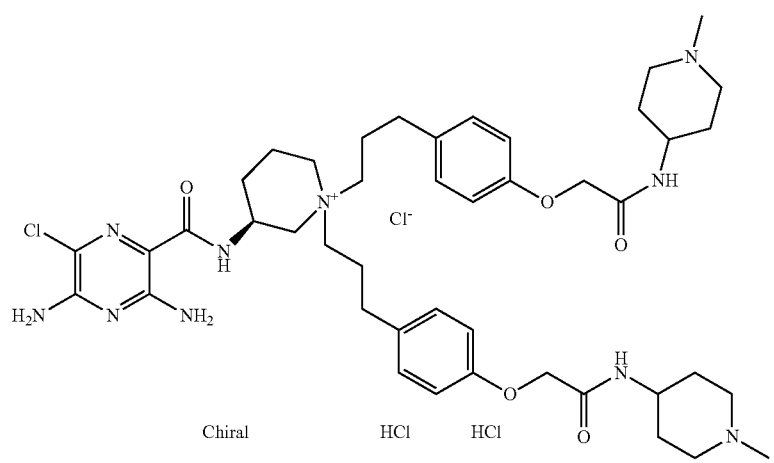<br>(S)-3-[(3,5-Diamino-6-chloro-pyrazine-2-carbonyl)-amino]-1,1-bis-(3-{4-[(1-methyl-piperidin-4-ylcarbamoyl)-methoxy]-phenyl}-propyl)-piperidinium chloride dihydrochloride | 424 (M++) | 0.82 | L | 0.015 |

-continued

Table of analoges:

| Ex. | Structure and name | ESI+ (M)+ | Rt | HPLC method | IC50 [μM] |
|---|---|---|---|---|---|
| 6.14 | 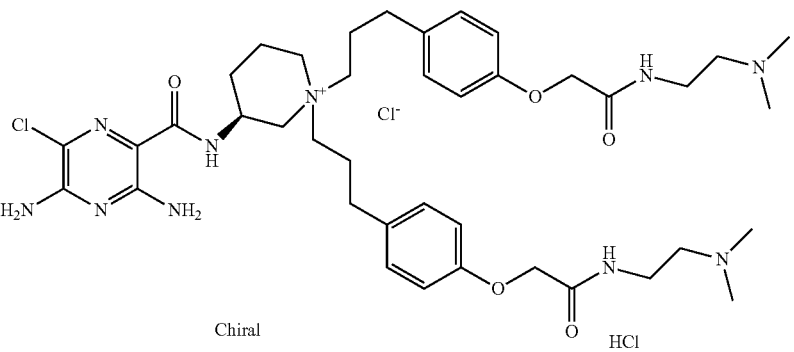<br>(S)-3-[(3,5-Diamino-6-chloro-pyrazine-2-carbonyl)-amino]-1,1-bis-(3-{4-[(2-dimethylamino-ethylcarbamoyl)-methoxy]-phenyl}-propyl)-piperidinium chloride dihydrochloride | 795 | 0.80 | L | 0.045 |
| 6.15 | 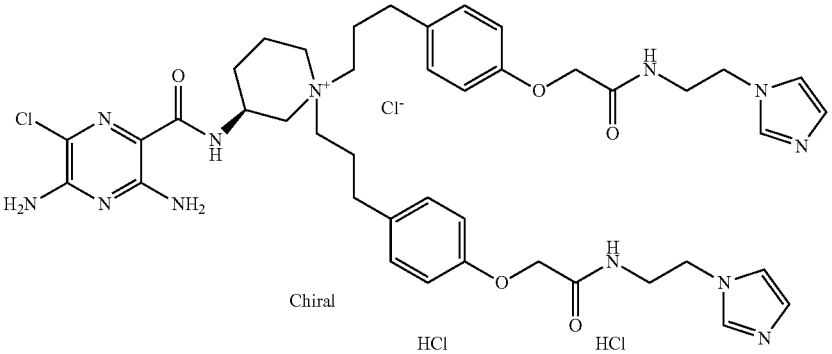<br>(S)-3-[(3,5-Diamino-6-chloro-pyrazine-2-carbonyl)-amino]-1,1-bis-(3-{4-[(2-imidazol-1-yl-ethylcarbamoyl)-methoxy]-phenyl}-propyl)-piperidinium chloride dihydrochloride | 841 | 0.68 | H | 0.009 |
| 6.16 | 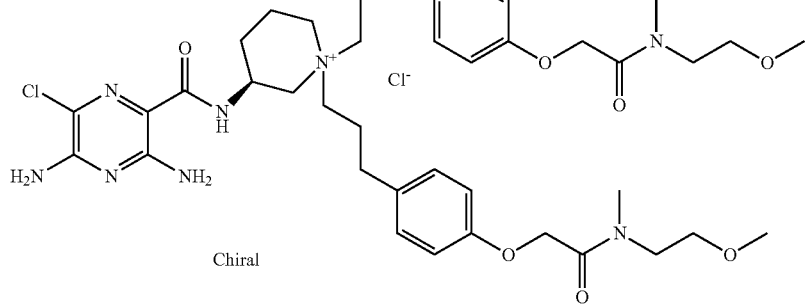<br>(S)-3-[(3,5-Diamino-6-chloro-pyrazine-2-carbonyl)-amino]-1,1-bis-[3-(4-{[(2-methoxy-ethyl)-methyl-carbamoyl]-methoxy}-phenyl)-propyl]-piperidinium chloride | 797 | 1.15 | H | 0.042 |

-continued

Table of analoges:

| Ex. | Structure and name | ESI+ (M)+ | Rt | HPLC method | IC50 [μM] |
|---|---|---|---|---|---|
| 6.17 | 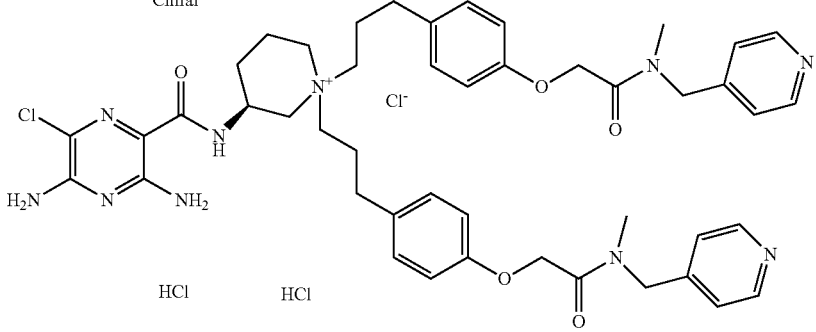<br>(S)-3-[(3,5-Diamino-6-chloro-pyrazine-2-carbonyl)-amino]-1,1-bis-(3-{4-[(methyl-pyridin-4-ylmethyl-carbamoyl)-methoxy]-phenyl}-propyl)-piperidinium chloride dihydrochloride | 863 | 0.75 | H | 0.021 |
| 6.18 | 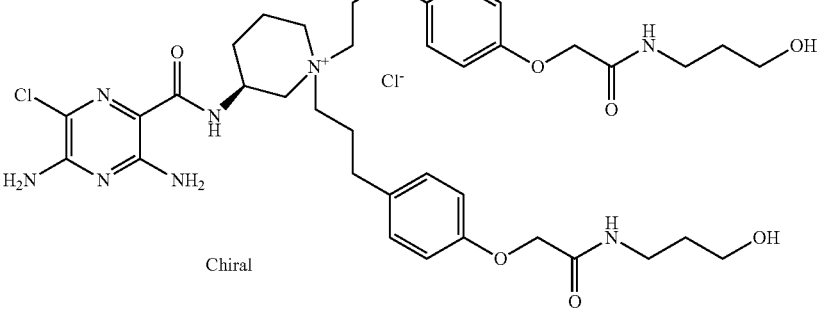<br>(S)-3-[(3,5-Diamino-6-chloro-pyrazine-2-carbonyl)-amino]-1,1-bis-(3-{4-[(3-hydroxy-propylcarbamoyl)-methoxy]-phenyl}-propyl)-piperidinium chloride | 769 | 1.03 | H | 0.013 |
| 6.19 | 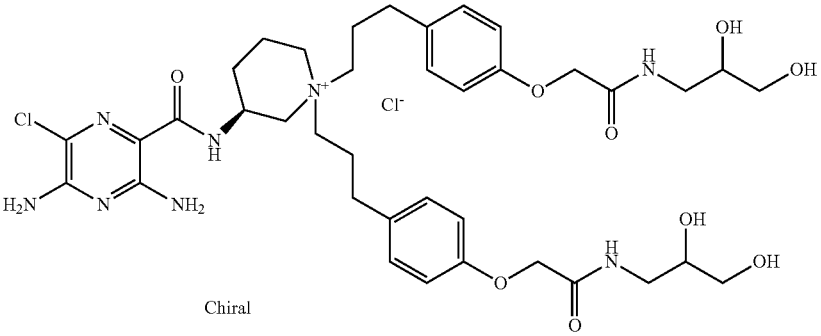<br>(S)-3-[(3,5-Diamino-6-chloro-pyrazine-2-carbonyl)-amino]-1,1-bis-(3-{4-[(2,3-dihydroxy-propylcarbamoyl)-methoxy]-phenyl}-propyl)-piperidinium chloride | 801 | 0.94 | H | 0.030 |

-continued

Table of analoges:

| Ex. | Structure and name | ESI+ (M)+ | Rt | HPLC method | IC50 [μM] |
|---|---|---|---|---|---|
| 6.20 | 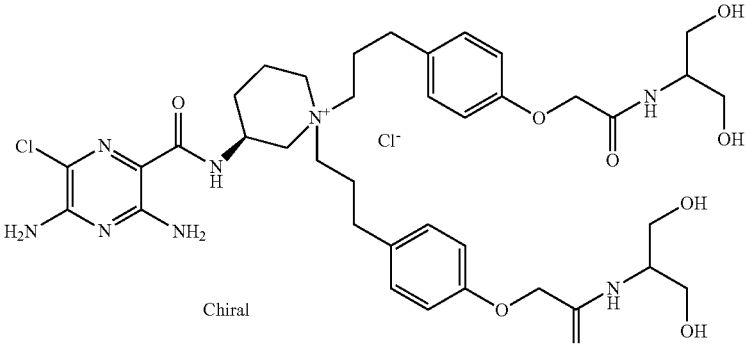<br>(S)-3-[(3,5-Diamino-6-chloro-pyrazine-2-carbonyl)-amino]-1,1-bis-(3-{4-[(2-hydroxy-1-hydroxymethyl-ethylcarbamoyl)-methoxy]-phenyl}-propyl)-piperidinium chloride | 801 | 0.94 | H | 0.046 |
| 6.21 | 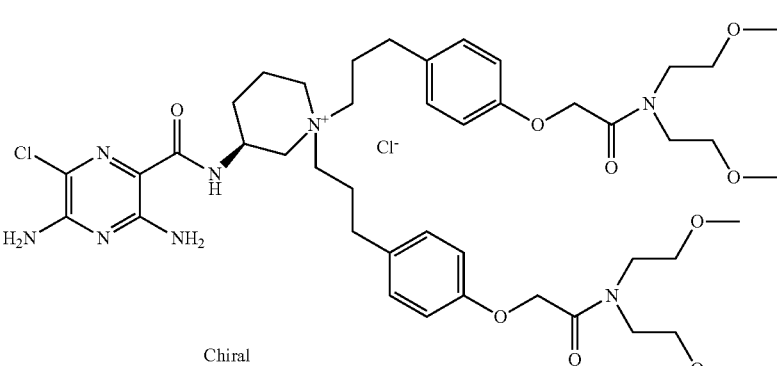<br>1,1-Bis-[3-(4-{[bis-(2-methoxy-ethyl)-carbamoyl]-methoxy}-phenyl)-propyl]-(S)-3-[(3,5-diamino-6-chloro-pyrazine-2-carbonyl)-amino]-piperidinium chloride | 885 | 1.25 | H | 0.023 |
| 6.22 | 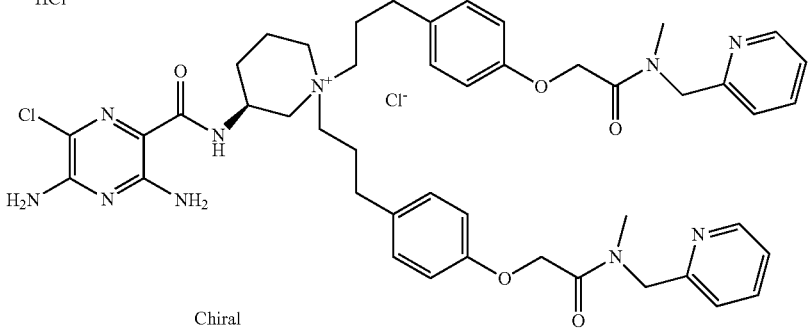<br>(S)-3-[(3,5-Diamino-6-chloro-pyrazine-2-carbonyl)-amino]-1,1-bis-(3-{4-[(methyl-pyridin-2-ylmethyl-carbamoyl)-methoxy]-phenyl}-propyl)-piperidinium chloride dihydrochloride | 863 | 0.94 | H | 0.018 |

-continued

Table of analoges:

| Ex. | Structure and name | ESI+ (M)+ | Rt | HPLC method | IC50 [μM] |
|---|---|---|---|---|---|
| 6.23 | 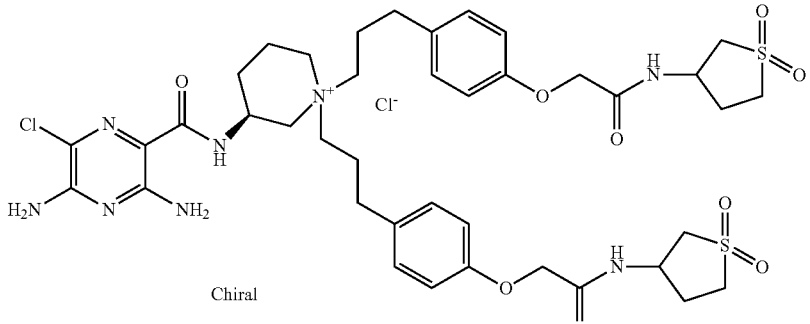<br>(S)-3-[(3,5-Diamino-6-chloro-pyrazine-2-carbonyl)-amino]-1,1-bis-(3-{4-[(1,1-dioxo-tetrahydro-thiophen-3-ylcarbamoyl)-methoxy]-phenyl}-propyl)-piperidinium chloride | 889 | 1.02 | H | 0.035 |
| 6.24 | 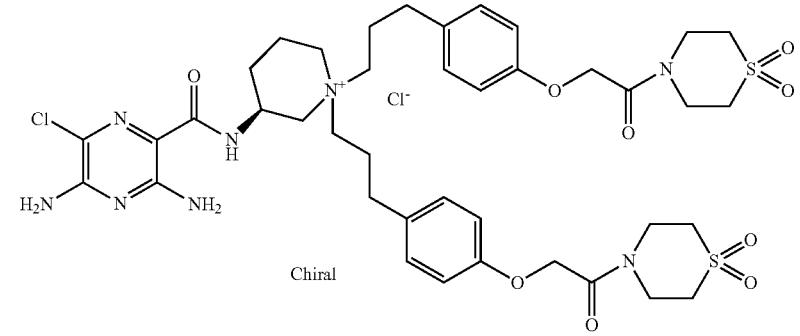<br>(S)-3-[(3,5-Diamino-6-chloro-pyrazine-2-carbonyl)-amino]-1,1-bis-(3-{4-[2-(1,1-dioxo--thiomorpholin-4-yl)-2-oxo-ethoxy]-phenyl}-propyl)-piperidinium chloride | 889 | 0.98 | H | 0.047 |
| 6.25 | 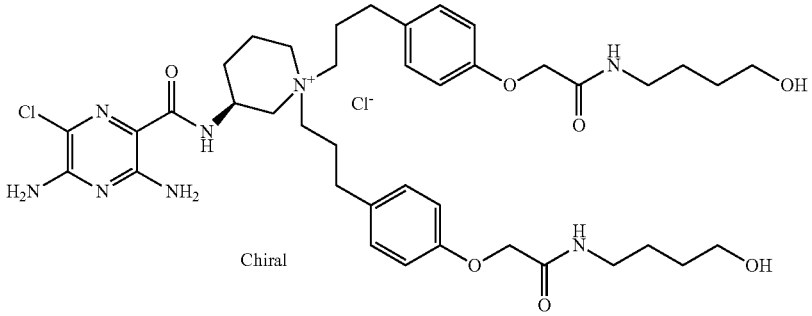<br>(S)-3-[(3,5-Diamino-6-chloro-pyrazine-2-carbonyl)-amino]-1,1-bis-(3-{4-[(4-hydroxy-butylcarbamoyl)-methoxy]-phenyl}-propyl)-piperidinium chloride | 797 | 1.07 | H | 0.014 |

-continued

Table of analoges:

| Ex. | Structure and name | ESI+ (M)+ | Rt | HPLC method | IC50 [μM] |
|---|---|---|---|---|---|
| 6.26 | 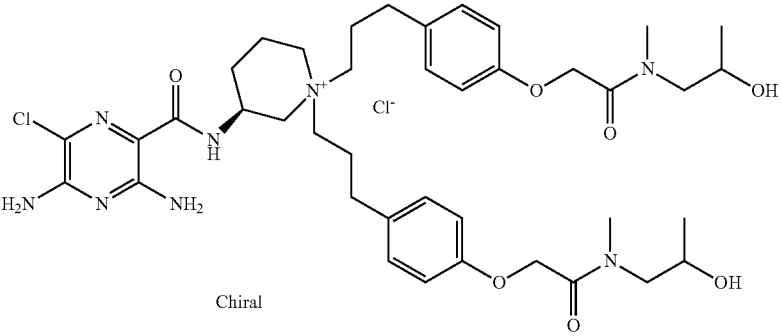 (S)-3-[(3,5-Diamino-6-chloro-pyrazine-2-carbonyl)-amino]-1,1-bis-[3-(4-{[(2-hydroxy-propyl)-methyl-carbamoyl]-methoxy}-phenyl)-propyl]-piperidinium chloride | 797 | 1.08 | H | 0.070 |
| 6.27 | 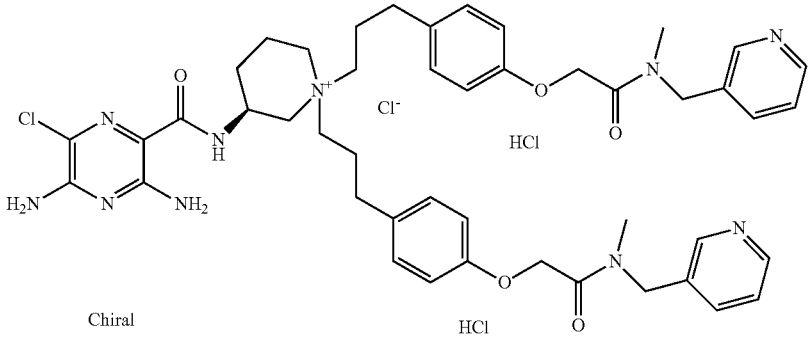 (S)-3-[(3,5-Diamino-6-chloro-pyrazine-2-carbonyl)-amino]-1,1-bis-(3-{4-[(methyl-pyridin-3-ylmethyl-carbamoyl)-methoxy]-phenyl}-propyl)-piperidinium chloride dihydrochloride | 863 | 0.79 | H | 0.017 |
| 6.28 | 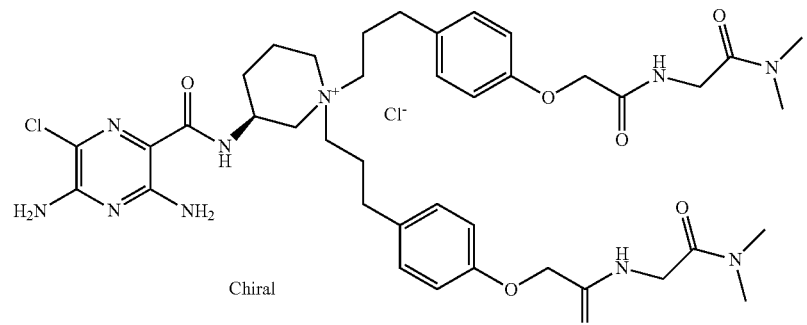 (S)-3-[(3,5-Diamino-6-chloro-pyrazine-2-carbonyl)-amino]-1,1-bis-(3-{4-[(dimethylcarbamoyl-methyl-carbamoyl)-methoxy]-phenyl}-propyl)-piperidinium chloride | 823 | 1.09 | H | 0.041 |

| Ex. | Structure and name | ESI+ (M)+ | Rt | HPLC method | IC50 [µM] |
|---|---|---|---|---|---|
| 6.29 | 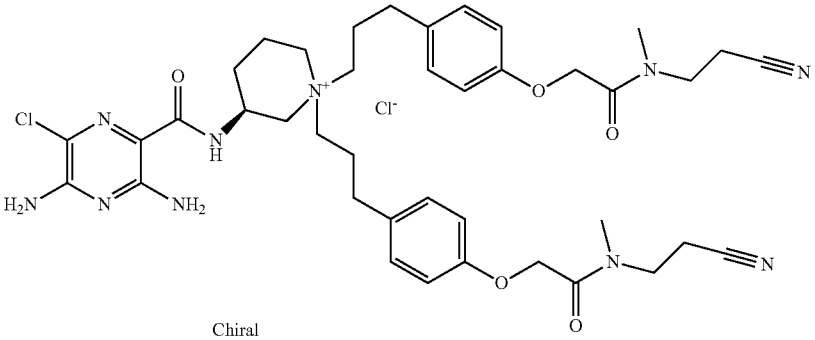<br>Chiral<br>(S)-1,1-Bis-[3-(4-{[(2-cyano-ethyl)-methyl-carbamoyl]-methoxy}-phenyl)-propyl]-3-[(3,5-diamino-6-chloro-pyrazine-2-carbonyl)-amino]-piperidinium chloride | 787 | 1.06 | H | 0.105 |
| 6.30 | 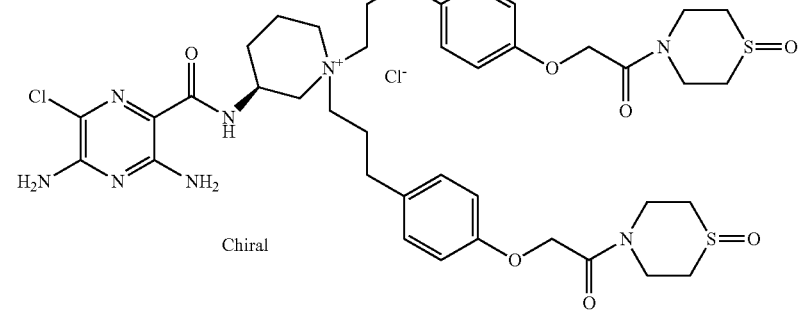<br>Chiral<br>(S)-3-[(3,5-Diamino-6-chloro-pyrazine-2-carbonyl)-amino]-1,1-bis-(3-{4-[2-oxo-2-(1-oxothiomorpholin-4-yl)-ethoxy]-phenyl}-propyl)-piperidinium chloride | 857 | 0.94 | H | 0.209 |
| 6.31 | 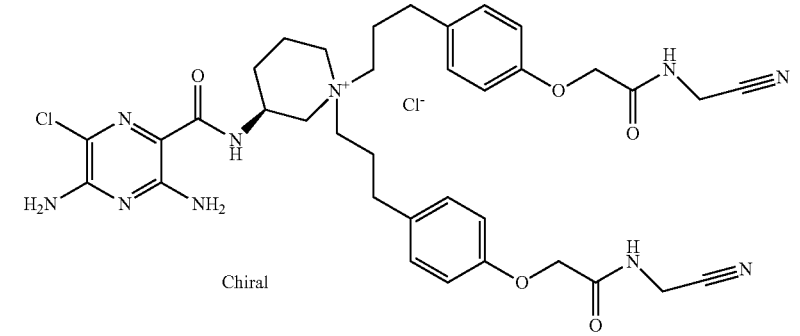<br>Chiral<br>(S)-1,1-Bis-(3-{4-[(cyanomethyl-carbamoyl)-methoxy]-phenyl}-propyl)-3-[(3,5-diamino-6-chloro-pyrazine-2-carbonyl)-amino]-piperidinium chloride | 731 | 1.03 | H | 0.018 |

-continued

Table of analoges:

| Ex. | Structure and name | ESI+ (M)+ | Rt | HPLC method | IC50 [μM] |
|---|---|---|---|---|---|
| 6.32 | 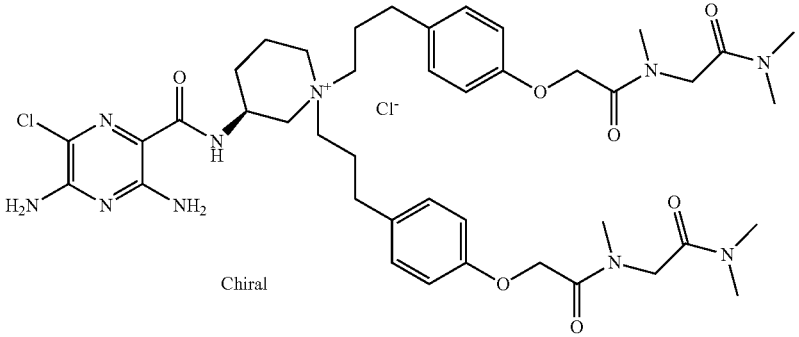<br>(S)-3-[(3,5-Diamino-6-chloro-pyrazine-2-carbonyl)-amino]-1,1-bis-(3-{4-[(dimethylcarbamoyl-methyl-methyl-carbamoyl)-methoxy]-phenyl}-propyl)-piperidinium chloride | 851 | 1.05 | H | 0.232 |
| 6.33 | 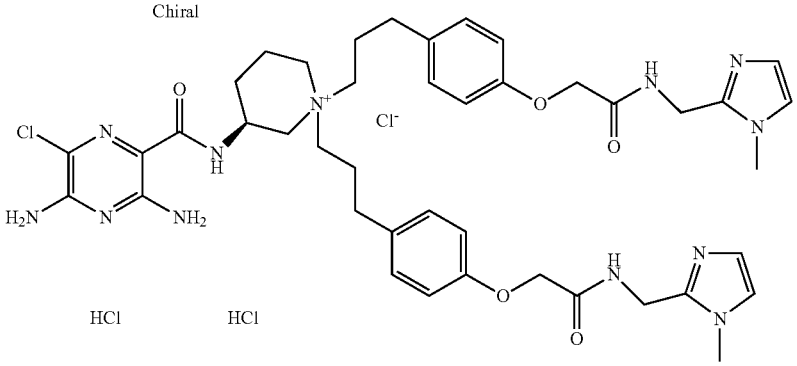<br>(S)-3-[(3,5-Diamino-6-chloro-pyrazine-2-carbonyl)-amino]-1,1-bis-[3-(4-{[(1-methyl-1H-imidazol-2-ylmethyl)-carbamoyl]-methoxy}-phenyl)-propyl]-piperidinium chloride | 841 | 0.74 | H | 0.021 |
| 6.34 | 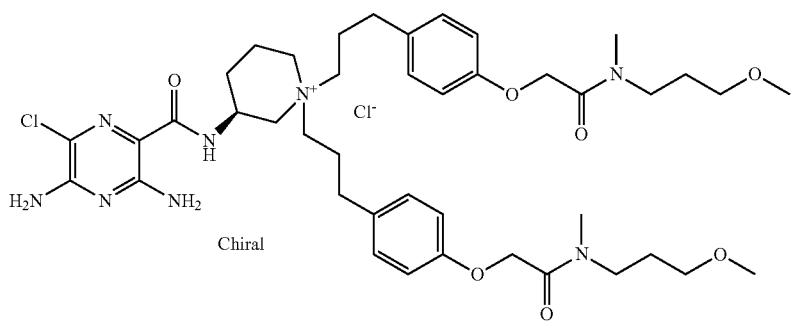<br>(S)-3-[(3,5-Diamino-6-chloro-pyrazine-2-carbonyl)-amino]-1,1-bis-[3-(4-{[(3-methoxy-propyl)-methyl-carbamoyl]-methoxy}-phenyl)-propyl]-piperidinium chloride | 875 | 1.21 | H | 0.044 |

Table of analoges:

| Ex. | Structure and name | ESI+ (M)+ | Rt | HPLC method | IC50 [μM] |
|---|---|---|---|---|---|
| 6.35 | 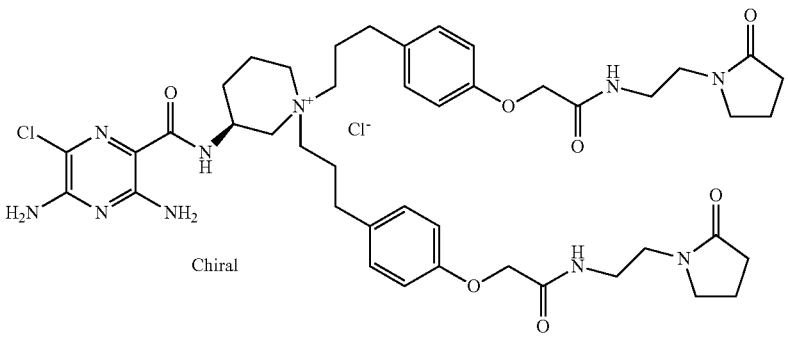<br>(S)-3-[(3,5-Diamino-6-chloro-pyrazine-2-carbonyl)-amino]-1,1-bis-[3-(4-{[2-(2-oxo-pyrrolidin-1-yl)-ethylcarbamoyl]-methoxy}-phenyl)-propyl]-piperidinium chloride | 875 | 1.08 | H | 0.016 |
| 6.36 | 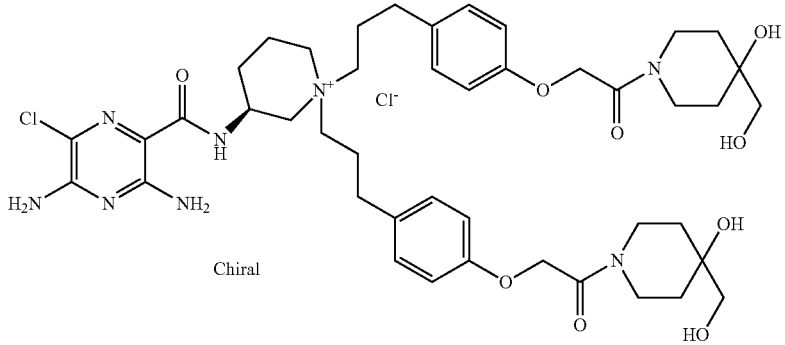<br>(S)-3-[(3,5-Diamino-6-chloro-pyrazine-2-carbonyl)-amino]-1,1-bis-(3-{4-[2-(4-hydroxy-4-hydroxymethyl-piperidin-1-yl)-2-oxo-ethoxy]-phenyl}-propyl)-piperidinium chloride | 881 | 1.00 | H | 0.067 |
| 6.37 | 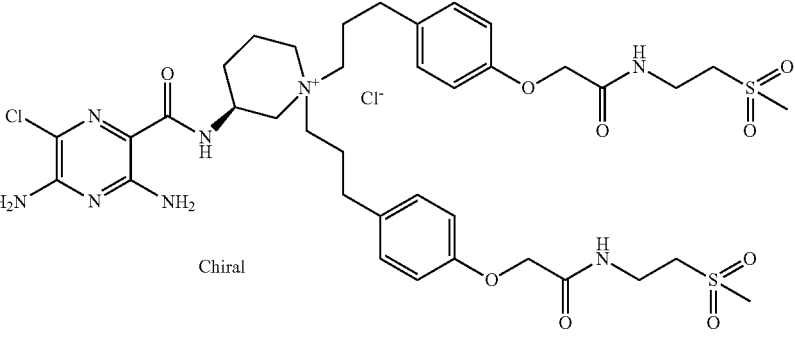<br>(S)-3-[(3,5-Diamino-6-chloro-pyrazine-2-carbonyl)-amino]-1,1-bis-(3-{4-[(2-methanesulfonyl-ethylcarbamoyl)-methoxy]-phenyl}-propyl)-piperidinium chloride | 865 | 1.00 | H | 0.028 |

-continued

Table of analoges:

| Ex. | Structure and name | ESI+ (M)+ | Rt | HPLC method | IC50 [μM] |
|---|---|---|---|---|---|
| 6.38 | 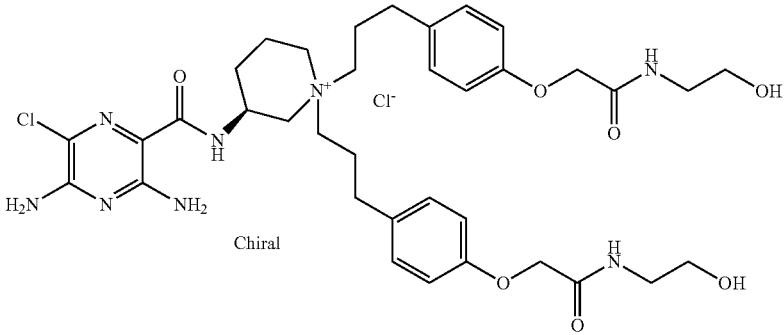<br>(S)-3-[(3,5-Diamino-6-chloro-pyrazine-2-carbonyl)-amino]-1,1-bis-(3-{4-[(2-hydroxy-ethylcarbamoyl)-methoxy]-phenyl}-propyl)-piperidinium chloride | 741 | 0.99 | H | 0.045 |
| 6.39 | 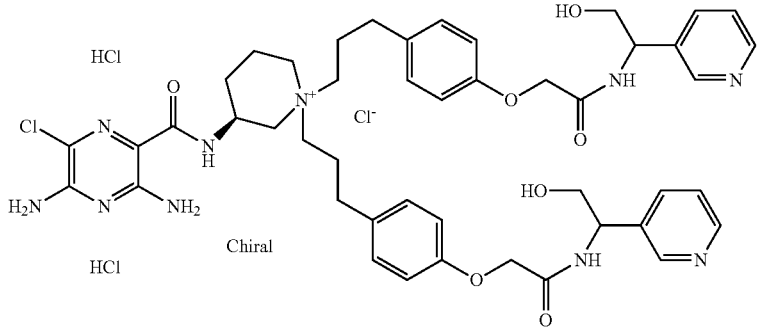<br>(S)-3-[(3,5-Diamino-6-chloro-pyrazine-2-carbonyl)-amino]-1-(3-{4-[2-(2-hydroxy-1-pyridin-3-yl-ethylamino)-allyloxy]-phenyl}-propyl)-1-(3-{4-[(2-hydroxy-1-pyridin-3-yl-ethylcarbamoyl)-methoxy]-phenyl}-propyl)-piperidinium chloride dihydrochloride | 895 | 0.76 | H | 0.011 |
| 6.40 | 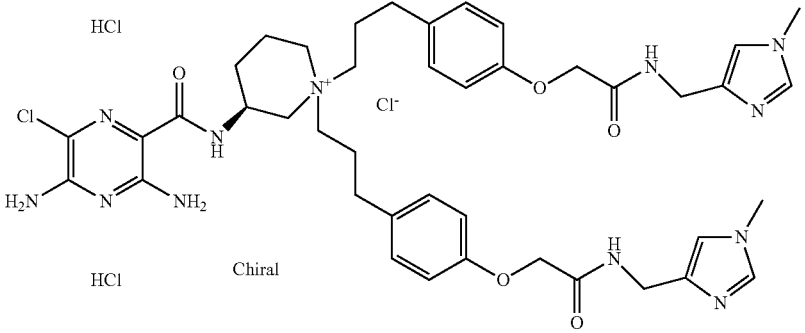<br>(S)-3-[(3,5-Diamino-6-chloro-pyrazine-2-carbonyl)-amino]-1,1-bis-[3-(4-{[(1-methyl-1H-imidazol-4-ylmethyl)-carbamoyl]-methoxy}-phenyl)-propyl]-piperidinium chloride dihydrochloride | 841 | 0.74 | H | 0.021 |

-continued

Table of analoges:

| Ex. | Structure and name | ESI+ (M)+ | Rt | HPLC method | IC50 [μM] |
|---|---|---|---|---|---|
| 6.41 | 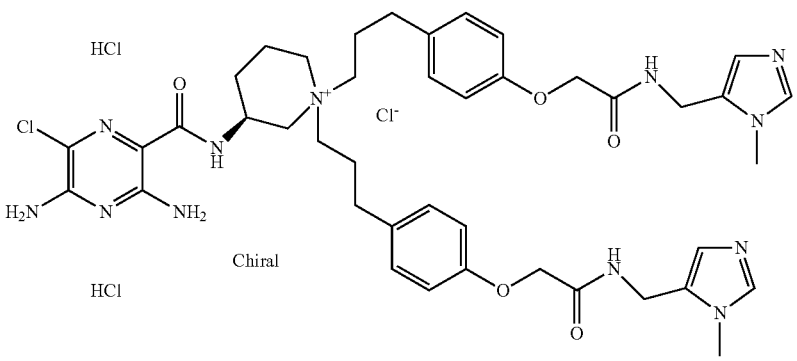<br>(S)-3-[(3,5-Diamino-6-chloro-pyrazine-2-carbonyl)-amino]-1,1-bis-[3-(4-{[(3-methyl-3H-imidazol-4-ylmethyl)-carbamoyl]-methoxy}-phenyl)-propyl]-piperidinium chloride dihydrochloride | 841 | 0.74 | H | 0.018 |
| 6.42 | 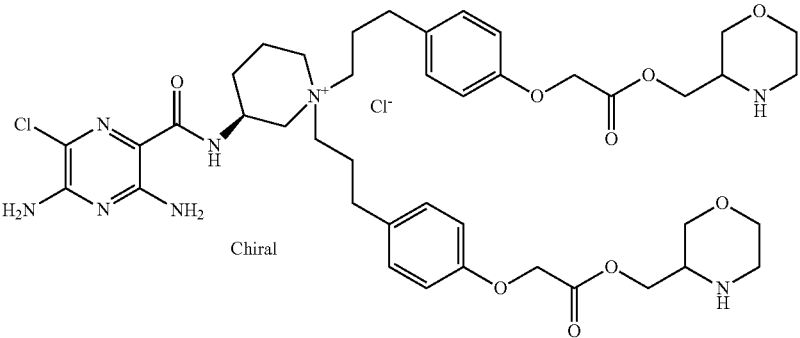<br>(S)-3-[(3,5-Diamino-6-chloro-pyrazine-2-carbonyl)-amino]-1,1-bis-{3-[4-(morpholin-3-ylmethoxycarbonylmethoxy)-phenyl]-propyl}-piperidinium chloride | 853 | 1.02 | H | 0.112 |
| 6.43 | 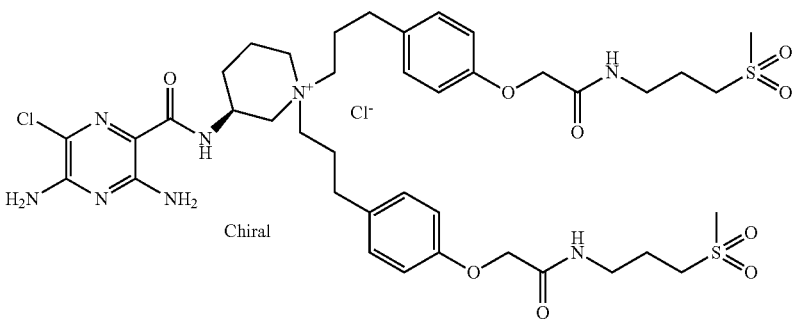<br>(S)-3-[(3,5-Diamino-6-chloro-pyrazine-2-carbonyl)-amino]-1,1-bis-(3-{4-[(3-methanesulfonyl-propylcarbamoyl)-methoxy]-phenyl}-propyl)-piperidinium chloride | 893 | 1.01 | H | 0.064 |

-continued

Table of analoges:

| Ex. | Structure and name | ESI+ (M)+ | Rt | HPLC method | IC50 [μM] |
|---|---|---|---|---|---|
| 6.44 | 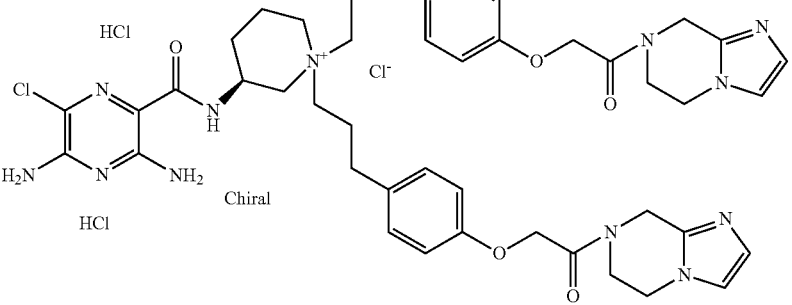<br>(S)-3-[(3,5-Diamino-6-chloro-pyrazine-2-carbonyl)-amino]-1,1-bis-(3-{4-[2-(5,6-dihydro-8H-imidazo[1,2-a]pyrazin-7-yl)-2-oxo-ethoxy]-phenyl}-propyl)-piperidinium chloride dihydrochloride | 865 | 0.70 | H | 0.088 |
| 6.45 | 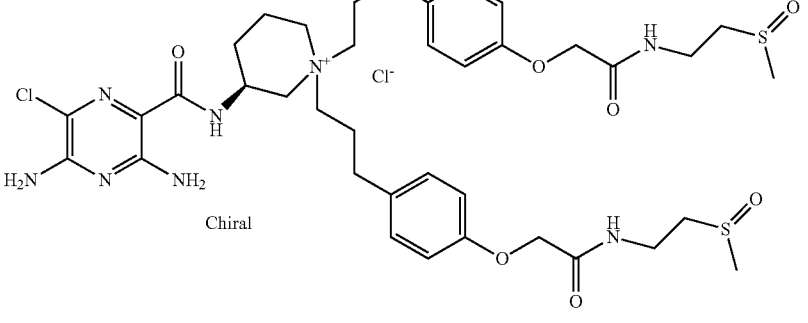<br>(S)-3-[(3,5-Diamino-6-chloro-pyrazine-2-carbonyl)-amino]-1,1-bis-(3-{4-[(2-methanesulfinyl-ethylcarbamoyl)-methoxy]-phenyl}-propyl)-piperidinium chloride | 833 | 0.98 | H | 0.039 |
| 6.46 | 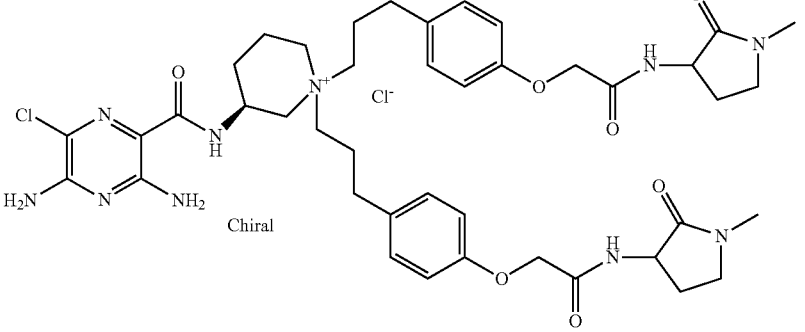<br>(S)-3-[(3,5-Diamino-6-chloro-pyrazine-2-carbonyl)-amino]-1,1-bis-(3-{4-[(1-methyl-2-oxo-pyrrolidin-3-ylcarbamoyl)-methoxy]-phenyl}-propyl)-piperidinium chloride | 847 | 1.04 | H | 0.083 |

Table of analoges:

| Ex. | Structure and name | ESI+ (M)+ | Rt | HPLC method | IC50 [μM] |
|---|---|---|---|---|---|
| 6.47 | 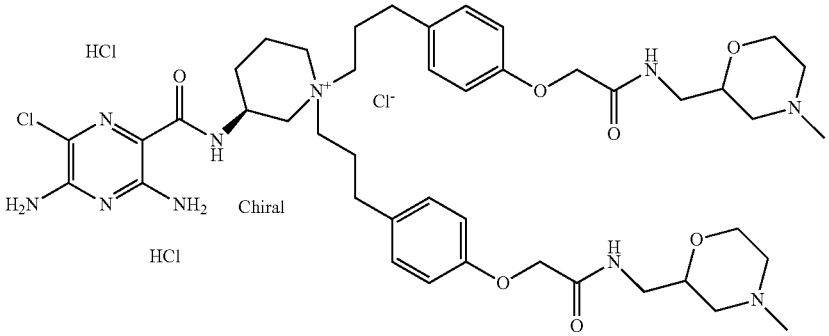<br>(S)-3-[(3,5-Diamino-6-chloro-pyrazine-2-carbonyl)-amino]-1,1-bis-[3-(4-{[(4-methyl-morpholin-2-ylmethyl)-carbamoyl]-methoxy}-phenyl)-propyl]-piperidinium chloride dihydrochloride | 879 | 0.77 | H | 0.011 |
| 6.48 | 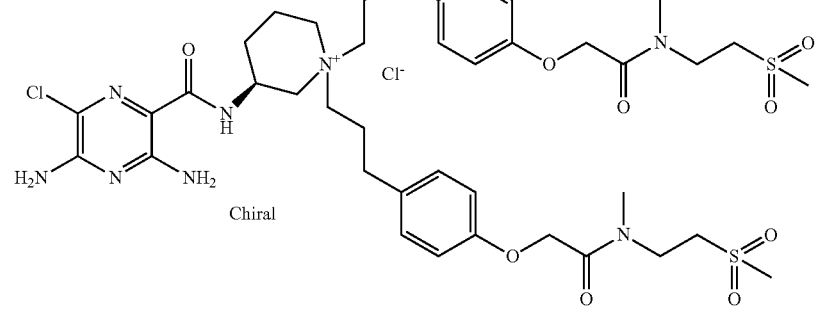<br>(S)-3-[(3,5-Diamino-6-chloro-pyrazine-2-carbonyl)-amino]-1,1-bis-[3-(4-{[(2-methane-sulfonyl-ethyl)-methyl-carbamoyl]-methoxy}-phenyl)-propyl]-piperidinium chloride | 893 | 1.00 | H | 0.085 |
| 6.49 | 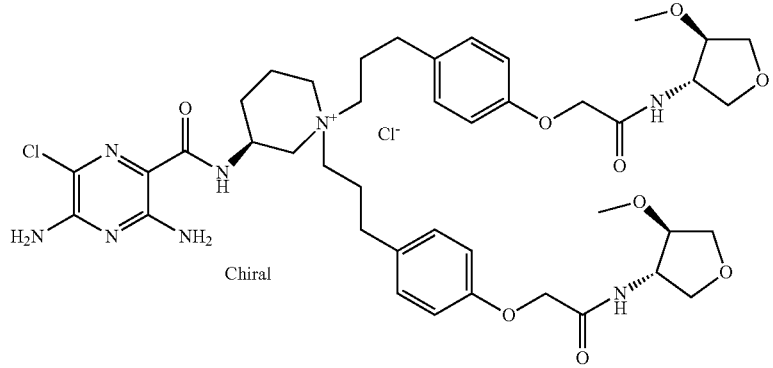<br>(S)-3-[(3,5-Diamino-6-chloro-pyrazine-2-carbonyl)-amino]-1,1-bis-(3-{4-[(4-methoxy-tetrahydro-furan-3-ylcarbamoyl)-methoxy]-phenyl}-propyl)-piperidinium chloride | 854 | 1.15 | H | 0.027 |

-continued

Table of analoges:

| Ex. | Structure and name | ESI+ (M)+ | Rt | HPLC method | IC50 [μM] |
|---|---|---|---|---|---|
| 6.50 | 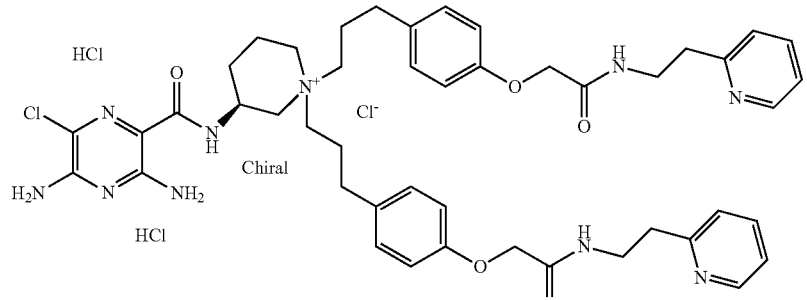<br>(S)-3-[(3,5-Diamino-6-chloro-pyrazine-2-carbonyl)-amino]-1,1-bis-(3-{4-[(2-pyridin-2-yl-ethylcarbamoyl)-methoxy]-phenyl}-propyl)-piperidinium chloride dihydrochloride | 863 | 0.79 | H | 0.006 |
| 6.51 | 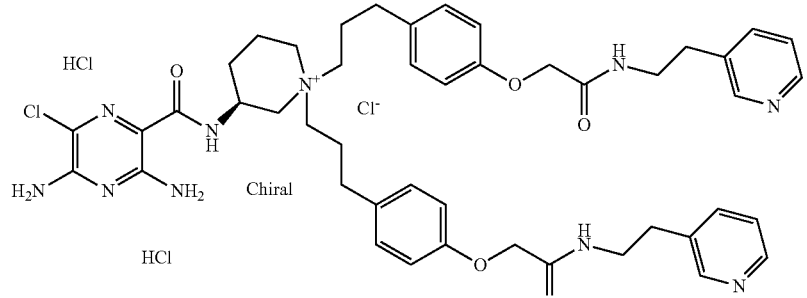<br>(S)-3-[(3,5-Diamino-6-chloro-pyrazine-2-carbonyl)-amino]-1,1-bis-(3-{4-[(2-pyridin-3-yl-ethylcarbamoyl)-methoxy]-phenyl}-propyl)-piperidinium chloride dihydrochloride | 863 | 0.79 | H | 0.005 |
| 6.52 | 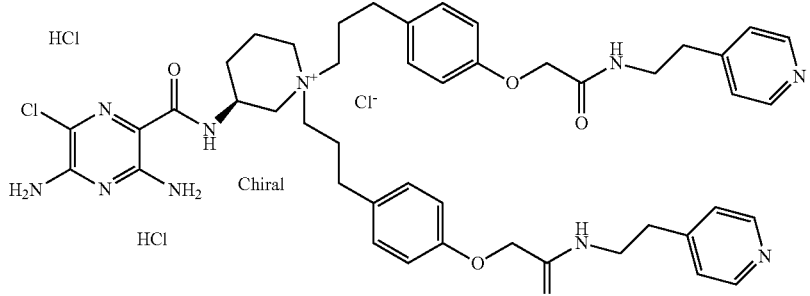<br>(S)-3-[(3,5-Diamino-6-chloro-pyrazine-2-carbonyl)-amino]-1,1-bis-(3-{4-[(2-pyridin-4-yl-ethylcarbamoyl)-methoxy]-phenyl}-propyl)-piperidinium chloride dihydrochloride | 863 | 0.76 | H | 0.004 |
| 6.53 | 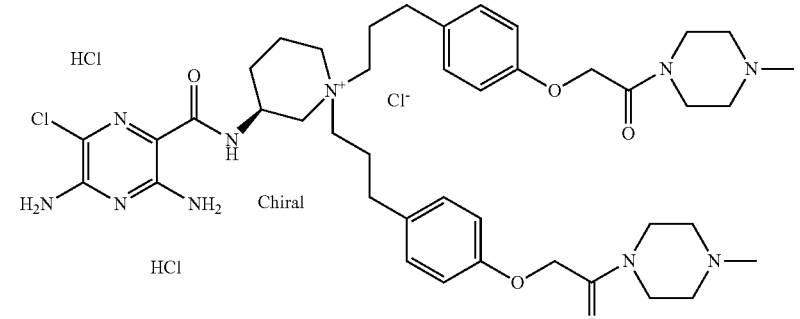<br>(S)-3-[(3,5-Diamino-6-chloro-pyrazine-2-carbonyl)-amino]-1,1-bis-(3-{4-[2-(4-methyl-piperazin-1-yl)-2-oxo-ethoxy]-phenyl}-propyl)-piperidinium chloride dihydrochloride | 819 | 0.69 | H | 0.039 |

-continued

Table of analoges:

| Ex. | Structure and name | ESI+ (M)+ | Rt | HPLC method | IC50 [μM] |
|---|---|---|---|---|---|
| 6.54 | 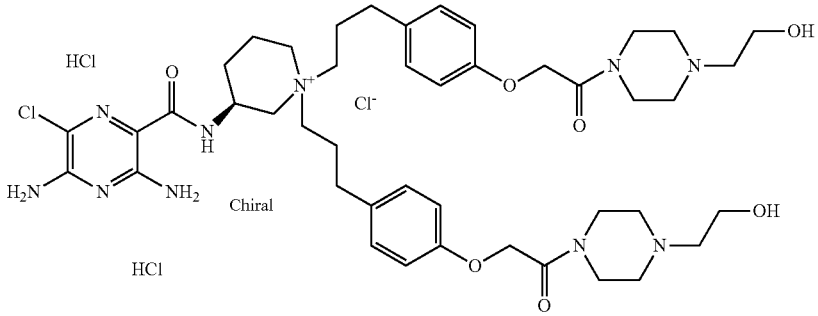<br>(S)-3-[(3,5-Diamino-6-chloro-pyrazine-2-carbonyl)-amino]-1,1-bis-[3-(4-{2-[4-(2-hydroxy-ethyl)-piperazin-1-yl]-2-oxo-ethoxy}-phenyl)-propyl]-piperidinium chloride dihydrochloride | 879 | 0.67 | H | 0.098 |
| 6.55 | 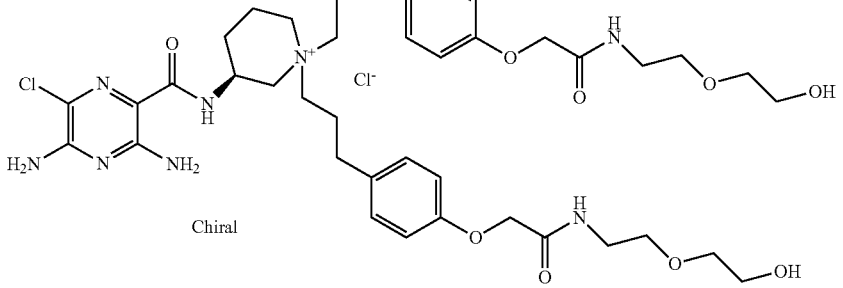<br>(S)- c 3-[(3,5-Diamino-6-chloro-pyrazine-2-carbonyl)-amino]-1,1-bis-[3-(4-{[2-(2-hydroxy-ethoxy)-ethylcarbamoyl]-methoxy}-phenyl)-propyl]-piperidinium hloride | 829 | 1.04 | H | 0.025 |
| 6.56 | 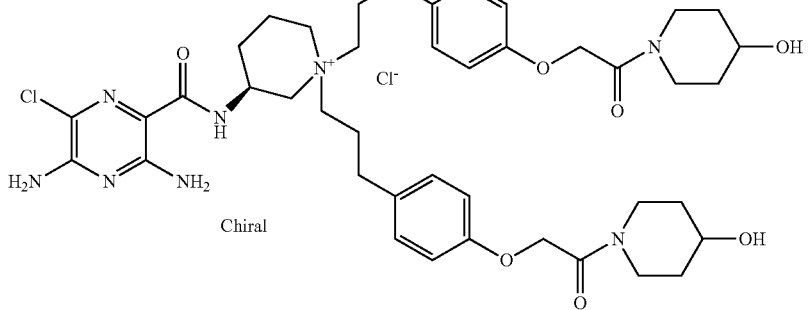<br>(S)-3-[(3,5-Diamino-6-chloro-pyrazine-2-carbonyl)-amino]-1,1-bis-(3-{4-[2-(4-hydroxy-piperidin-1-yl)-2-oxo-ethoxy]-phenyl}-propyl)-piperidinium chloride | 821 | 1.04 | H | 0.092 |

-continued

Table of analoges:

| Ex. | Structure and name | ESI+ (M)+ | Rt | HPLC method | IC50 [μM] |
|---|---|---|---|---|---|
| 6.57 | 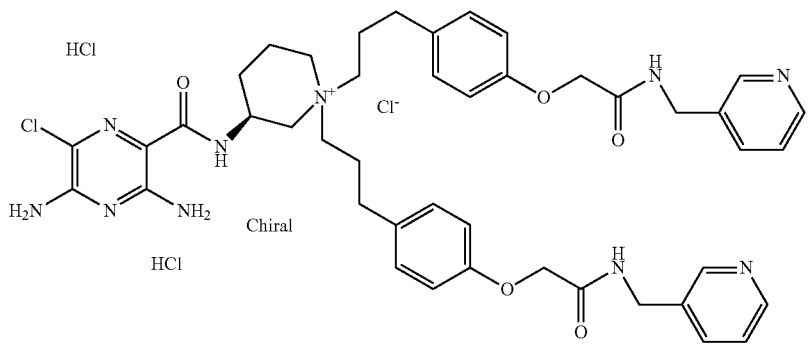(S)-3-[(3,5-Diamino-6-chloro-pyrazine-2-carbonyl)-amino]-1,1-bis-[3-(4-{[(pyridin-3-ylmethyl)-carbamoyl]-methoxy}-phenyl)-propyl]-piperidinium chloride dihydrochloride | 835 | 0.79 | H | 0.004 |
| 6.58 | 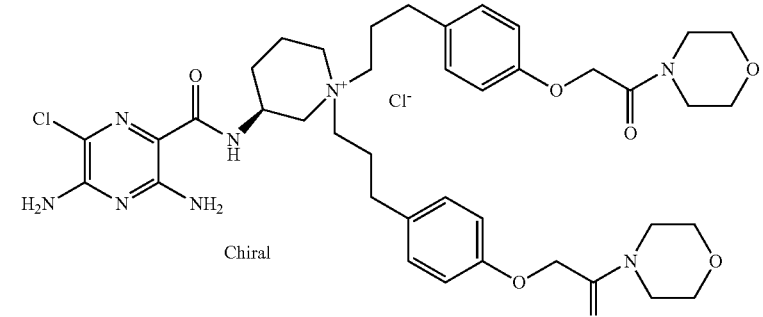(S)-3-[(3,5-Diamino-6-chloro-pyrazine-2-carbonyl)-amino]-1,1-bis-{3-[4-(2-morpholin-4-yl-2-oxo-ethoxy)-phenyl]-propyl}-piperidinium chloride | 793 | 1.09 | H | 0.072 |
| 6.59 | 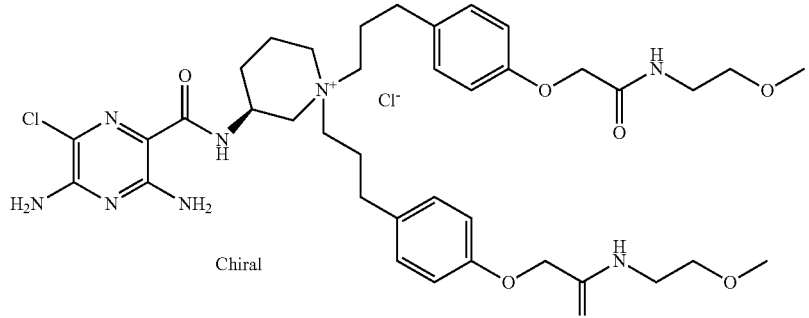(S)-3-[(3,5-Diamino-6-chloro-pyrazine-2-carbonyl)-amino]-1,1-bis-(3-{4-[(2-methoxy-ethylcarbamoyl)-methoxy]-phenyl}-propyl)-piperidinium chloride | 769 | 1.14 | H | 0.012 |

-continued

Table of analoges:

| Ex. | Structure and name | ESI+ (M)+ | Rt | HPLC method | IC50 [μM] |
|---|---|---|---|---|---|
| 6.60 | 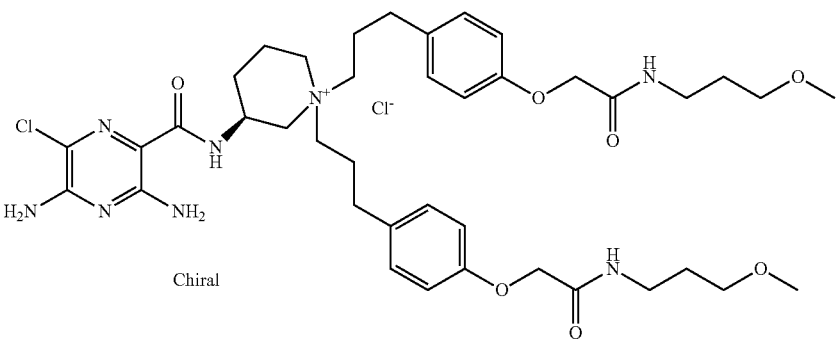<br>(S)-3-[(3,5-Diamino-6-chloro-pyrazine-2-carbonyl)-amino]-1,1-bis-(3-{4-[(3-methoxy-propylcarbamoyl)-methoxy]-phenyl}-propyl)-piperidinium chloride | 797 | 1.20 | H | 0.007 |
| 6.61 | 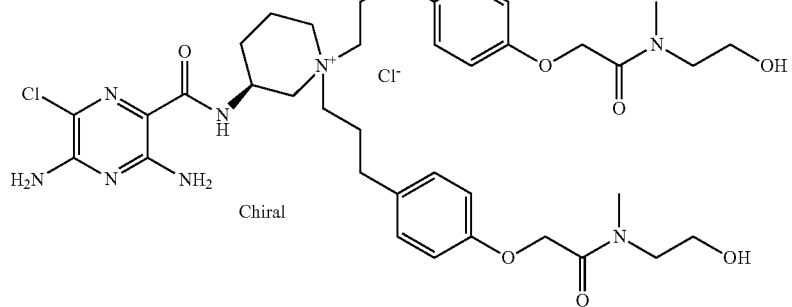<br>(S)-3-[(3,5-Diamino-6-chloro-pyrazine-2-carbonyl)-amino]-1,1-bis-[3-(4-{[(2-hydroxy-ethyl)-methyl-carbamoyl]-methoxy}-phenyl)-propyl]-piperidinium chloride | 769 | 1.00 | H | 0.108 |
| 6.62 | 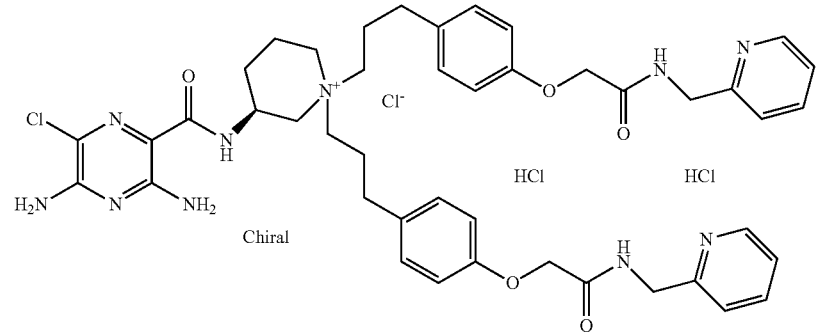<br>(S)-3-[(3,5-Diamino-6-chloro-pyrazine-2-carbonyl)-amino]-1,1-bis-[3-(4-{[(pyridin-2-ylmethyl)-carbamoyl]-methoxy}-phenyl)-propyl]-piperidinium chloride dihydrochloride | 835 | 0.86 | H | 0.005 |

-continued

Table of analoges:

| Ex. | Structure and name | ESI+ (M)+ | Rt | HPLC method | IC50 [μM] |
|---|---|---|---|---|---|
| 6.63 | 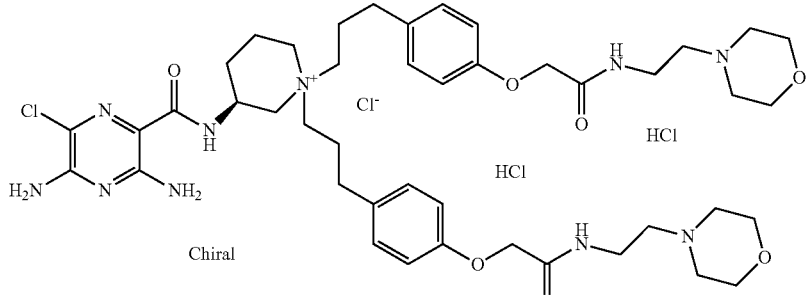<br>(S)-3-[(3,5-Diamino-6-chloro-pyrazine-2-carbonyl)-amino]-1,1-bis-(3-{4-[(2-morphiolin-4-yl-ethylcarbamoyl)-methoxy]-phenyl}-propyl)-piperidinium chloride dihydrochloride | 879 | 0.75 | H | 0.042 |
| 6.64 | 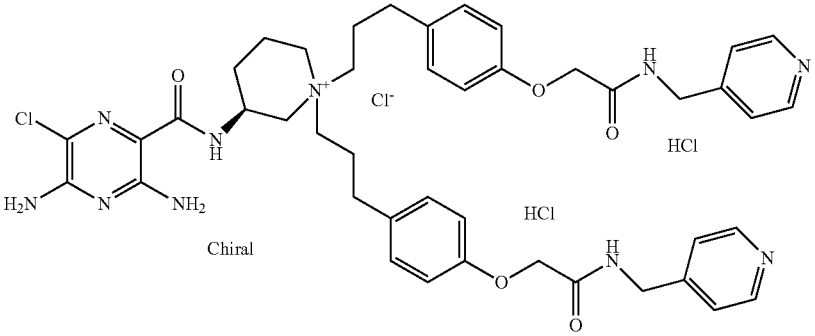<br>(S)-3-[(3,5-Diamino-6-chloro-pyrazine-2-carbonyl)-amino]-1,1-bis-[3-(4-{[(pyridin-4-ylmethyl)-carbamoyl]-methoxy}-phenyl)-propyl]-piperidinium chloride dihydrochloride | 835 | 0.75 | H | 0.004 |
| 6.65 | 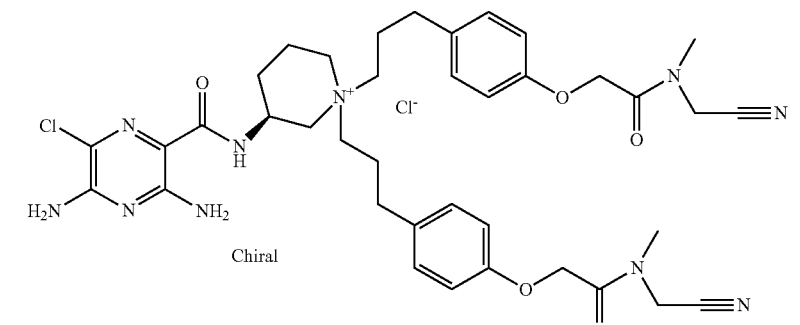<br>(S)-1,1-Bis-(3-{4-[(cyanomethyl-methyl-carbamoyl)-methoxy]-phenyl}-propyl)-3-[(3,5-diamino-6-chloro-pyrazine-2-carbonyl)-amino]-piperidinium chloride | 759 | 1.08 | H | 0.094 |

Table of analoges:

| Ex. | Structure and name | ESI+ (M)+ | Rt | HPLC method | IC50 [µM] |
|---|---|---|---|---|---|
| 6.66 | 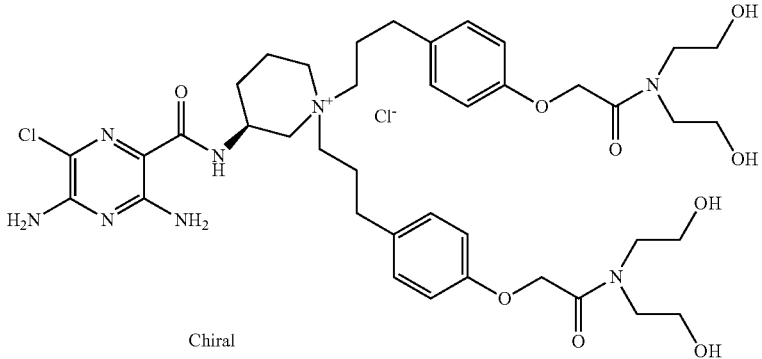<br>(S)-1,1-Bis-[3-(4-{[bis-(2-hydroxy-ethyl)-carbamoyl]-methoxy}-phenyl)-propyl]-3-[(3,5-diamino-6-chloro-pyrazine-2-carbonyl)-amino]-piperidinium chloride | 829 | 0.92 | H | 0.121 |
| 6.67 | 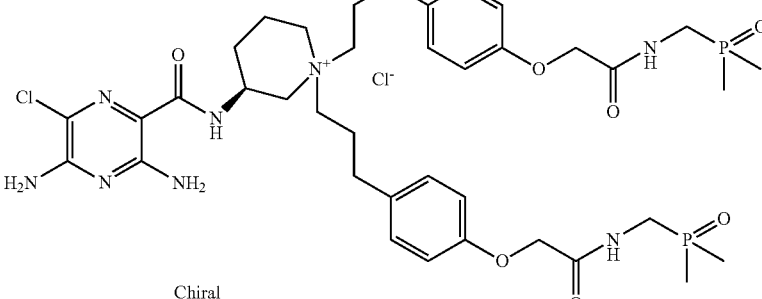<br>(S)-3-[(3,5-Diamino-6-chloro-pyrazine-2-carbonyl)-amino]-1,1-bis-[3-(4-{[(dimethyl-phosphinoylmethyl)-carbamoyl]-methoxy}-phenyl)-propyl]-piperidinium chloride | 833 | 0.96 | H | 0.131 |

Example 6.15

3-[(3,5-Diamino-6-chloro-pyrazine-2-carbonyl)-amino]-1,1-bis-[3-(4-hydroxy-phenyl)propyl]-piperidinium trifluoroacetate

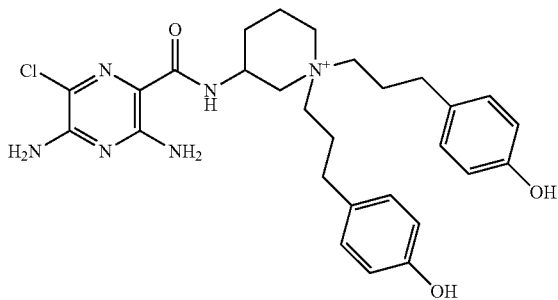

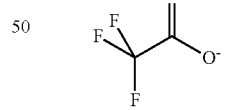

-continued

3-Amino-1,1-bis-[3-(4-hydroxy-phenyl)-propyl]-piperidinium chloride hydrochloride (390 mg, 0.88 mmol), 3,5-Diamino-6-chloro-pyrazine-2-carboxylic acid (180 mg, 0.94 mmol) and N,N-Diisopropylethylamine (750 µl, 4.3 mmol) are dissolved in N,N-dimethyl-formamide (15 ml), 2-(1H-Benzotriazol-1-yl)-1,1,3,3-tetramethyluronium tetrafluoroborate (290 mg, 0.9 mmol) is added. The reaction is stirred at room temperature overnight and purified by preparative HPLC-MS (MeOH/H2O+0.1% TFA). LC (method I): $t_R$=1.43 min; Mass spectrum (ESI$^+$): m/z=539 [M]$^+$. IC50=0.013.

Example 7

{(S)-2-[(3,5-Diamino-6-chloro-pyrazine-2-carbonyl)-amino]-3-methoxycarbonyl-propyl}-bis-[3-(4-methoxy-phenyl)-propyl]-methyl-ammonium chloride

Intermediate 7.1: (S)-3-Benzyloxycarbonylamino-4-{bis-[3-(4-methoxy-phenyl)-propyl]-amino}-butyric acid methyl ester

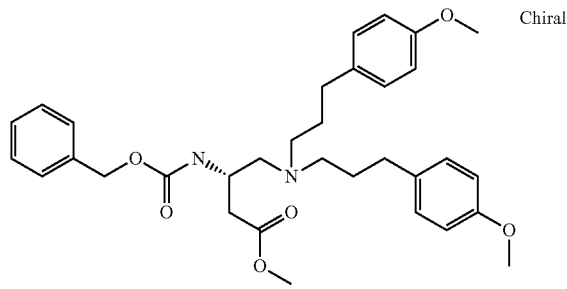 [SMILES: COC(=O)C[C@@H](CN(CCCc1ccc(OC)cc1)CCCc1ccc(OC)cc1)NC(=O)OCc1ccccc1]

Sodium triacetoxyborohydride (700 mg, 3 mmol) is added to a solution of S-4-Amino-3-benzyloxycarbonylamino-butyric acid methyl ester hydrochloride (230 mg, 0.76 mmol), 3-(4-Methoxyphenyl)-propionaldehyde (350 mg, 2 mmol) and DIPEA (130 µl, 0.76 mmol) in THF (5 ml) and acetic acid (44 µl, 0.76 mmol) and stirred at room temperature overnight. The resulting mixture is filtered through a pad of basic aluminum oxide. The pad is washed with dichloromethane/methanol (9:1) and the combined filtrates are concentrated in vacuo. The product is purified by preparative HPLC-MS (MeOH/H2O+0.1% TFA). The product is dissolved in dichloromethane/methanol (9:1), a potassium carbonate solution (5M) is added and filtered through a pad of basic aluminum oxide. The pad is washed with dichloromethane/methanol (9:1) and the combined filtrates are concentrated in vacuo to give the free base. LC (method Z002_003): $t_R$=1.17 min; Mass spectrum (ESI$^+$): m/z=563 [M+H]$^+$.

Intermediate 7.2: (S)-(2-Benzyloxycarbonylamino-3-methoxycarbonyl-propyl)-bis-[3-(4-methoxy-phenyl)-propyl]-methyl-ammonium chloride

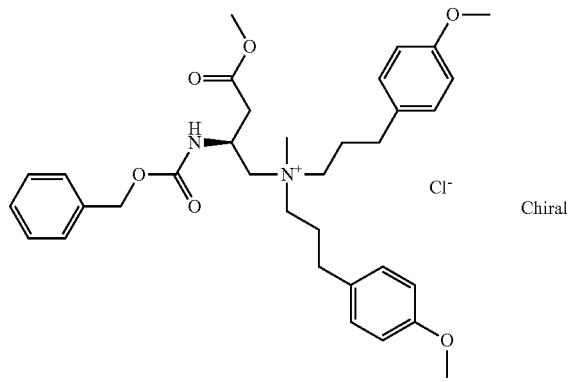 [SMILES: COC(=O)C[C@@H](C[N+](C)(CCCc1ccc(OC)cc1)CCCc1ccc(OC)cc1)NC(=O)OCc1ccccc1 ; [Cl-]]

(S)-3-Benzyloxycarbonylamino-4-{bis-[3-(4-methoxyphenyl)-propyl]-amino}-butyric acid methyl ester (122 mg, 0.217 mmol) and methyliodide (20 µl, 0.316 mmol) are dissolved in acetonitril and stirred at 40° C. overnight. The solvent and MeI are removed under vacuo and the product is purified by preparative HPLC-MS (MeOH/H2O+0.1% TFA). Approx. 0.5 mL 1 M HCl is added to the fractions and concentrated in vacuo. LC (method Z002_003): $t_R$=1.17 min; Mass spectrum (ESI$^+$): m/z=577 [M+]$^+$.

Intermediate 7.3: (S-2-Amino-3-methoxycarbonyl-propyl)-bis-[3-(4-methoxy-phenyl)-propyl]-methyl-ammonium chloride hydrochloride

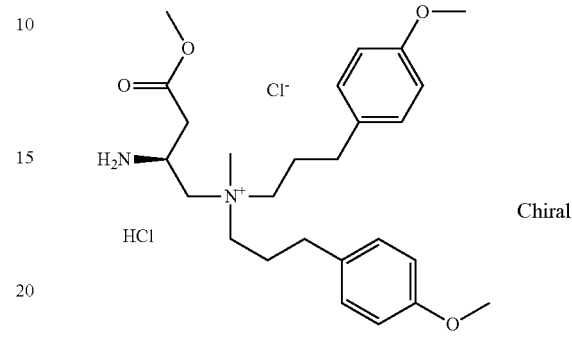

S-(2-Benzyloxycarbonylamino-3-methoxycarbonyl-propyl)-bis-[3-(4-methoxy-phenyl)-propyl]-methyl-ammonium chloride (80 mg, 0.13 mmol) is dissolved in methanol (2 ml) and 1M HCl (0.5 ml), 50 mg of Pd/C (10%) is added and shaked under 50 psi hydrogen pressure at room temperature for 3 h. The reaction is filtered and the filtrate concentrated in vacuo. LC (method I): $t_R$=1.45 min; Mass spectrum (ESI$^+$): m/z=443 [M+]$^+$.

Example 7

{(S)-2-[(3,5-Diamino-6-chloro-pyrazine-2-carbonyl)-amino]-3-methoxycarbonyl-propyl}-bis-[3-(4-methoxy-phenyl)-propyl]-methyl-ammonium chloride

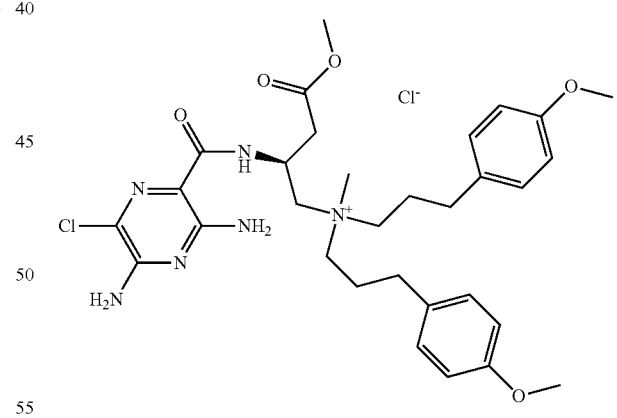

(S-2-Amino-3-methoxycarbonyl-propyl)-bis-[3-(4-methoxy-phenyl)-propyl]-methyl-ammonium chloride hydrochloride (55 mg, 0.107 mmol)), 3,5-Diamino-6-chloro-pyrazine-2-carboxylic acid (22 mg, 0.117 mmol) and N,N-Diisopropylethylamine (50 µl, 0.29 mmol) are dissolved in N,N-dimethylformamide (1 ml), 2-(1H-Benzotriazol-1-yl)-1,1,3,3-tetramethyluronium tetrafluoroborate (36 mg, 0.112 mmol) is added. The reaction is stirred at room temperature overnight. The resulting mixture is filtered through a pad of basic aluminum oxide. The pad is washed with N,N-dimethylformamide/methanol (9:1) and the combined filtrates are concentrated in vacuo. The product is purified by preparative HPLC-MS (MeOH/H2O+0.1% TFA). 0.1 mL 1 M HCl is added to form chloride salt and solvent removed in vacuo. LC (method I): $t_R$=1.61 min; Mass spectrum (ESI+): m/z=613 [M]$^+$. IC50=0.021.

Example 7.1

{(R)-2-[(3,5-Diamino-6-chloro-pyrazine-2-carbonyl)-amino]-3-methoxycarbonyl-propyl}-bis-[3-(4-methoxy-phenyl)-propyl]-methyl-ammonium chloride

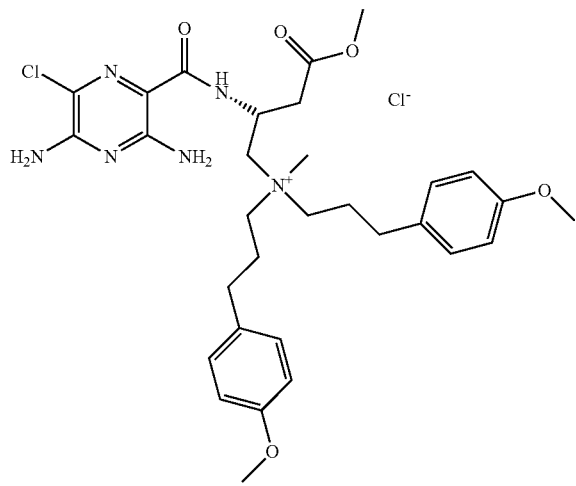

The title compound is prepared from R-4-Amino-3-benzyloxycarbonylamino-butyric acid methyl ester hydrochloride following a procedure analogous to that described for the S-derivative. The title compound and all intermediates have the same physicochemical properties as the intermediates of the S-derivatives. IC50=1.3

Example 7.2

{(S)-3-Carboxy-2-[(3,5-diamino-6-chloro-pyrazine-2-carbonyl)-amino]-propyl}-bis-[3-(4-methoxy-phenyl)-propyl]-methyl-ammonium

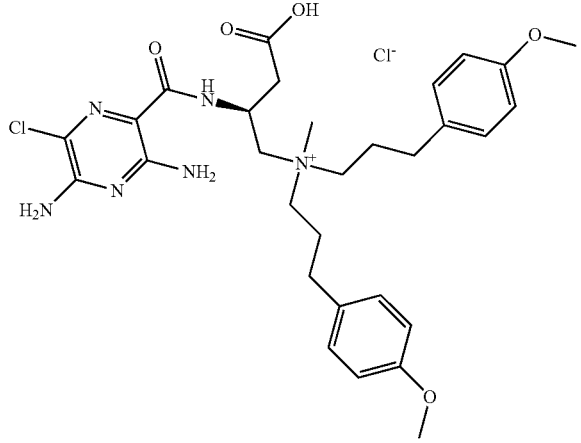 [SMILES: COc1ccc(CCC[N+](C)(CCCc2ccc(OC)cc2)C[C@H](CC(=O)O)NC(=O)c2nc(Cl)c(N)nc2N)cc1 ; [Cl-]]

{(S)-2-[(3,5-Diamino-6-chloro-pyrazine-2-carbonyl)-amino]-3-methoxycarbonyl-propyl}-bis-[3-(4-methoxy-phenyl)-propyl]-methyl-ammonium chloride (28 mg, 0.044 mmol) is dissolved in tetrahydrofurane (1 ml) and 1N sodium hydroxide (0.22 ml, 0.22 mmol) and stirred at room temperature overnight. The reaction is acidified with 1M HCl and purified by preparative HPLC-MS (MeOH/H2O+0.1% TFA). LC (method F): $t_R$=1.68 min; Mass spectrum (ESI+): m/z=599 [M+H]$^+$. IC50=1.38 µM (Metabolite)

Example 7.3

[(S)-2-[(3,5-Diamino-6-chloro-pyrazine-2-carbonyl)-amino]-3-(2-trimethylammonium-ethylcarbamoyl)-propyl]-bis-[3-(4-methoxy-phenyl)-propyl]-methyl-ammonium dichloride

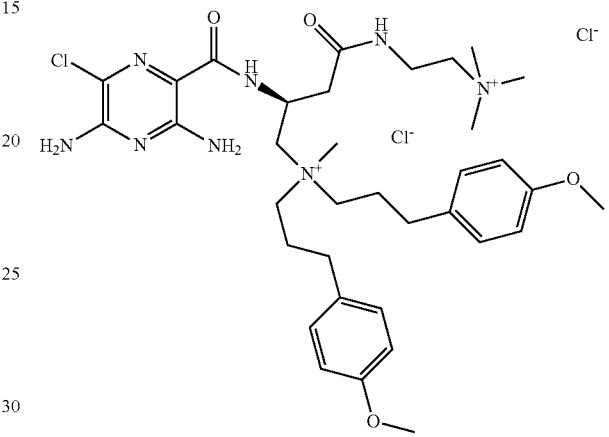

{(S)-3-Carboxy-2-[(3,5-diamino-6-chloro-pyrazine-2-carbonyl)-amino]-propyl}-bis-[3-(4-methoxy-phenyl)-propyl]-methyl-ammonium (5 mg, 0.008 mmol)), (2-Aminoethyl)-trimethyl-ammonium chloride hydrochloride (2 mg, 0.011 mmol) and N,N-Diisopropylethylamine (4 µl, 0.023 mmol) are dissolved in N,N-dimethylformamide (1 ml), 2-(1H-Benzotriazol-1-yl)-1,1,3,3-tetramethyluronium tetrafluoroborate (2.7 mg, 0.008 mmol) is added. The reaction is stirred at room temperature overnight. The resulting mixture is purified by preparative HPLC-MS (MeOH/H2O+0.1% TFA). 0.1 mL 1 M HCl is added to form chloride salt and solvent removed in vacuo. LC (method G): $t_R$=1.31 min; Mass spectrum (ESI$^+$): m/z=342 [M]$^{++}$.

Example 8

1-[3-(4-Carboxymethoxy-phenyl)-propyl]-3-[(3,5-diamino-6-chloro-pyrazine-2-carbonyl)amino]-1-[3-(4-methoxycarbonylmethoxy-phenyl)-propyl]-piperidinium trifluoroacetate

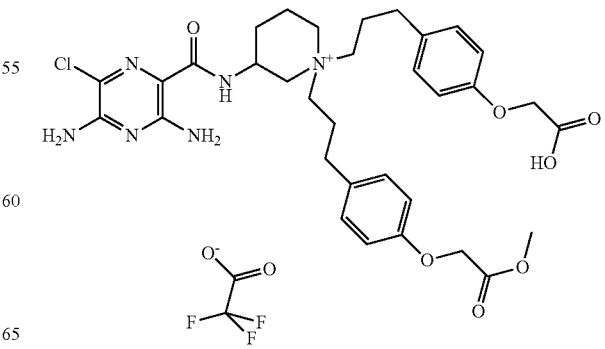

3-[(3,5-Diamino-6-chloro-pyrazine-2-carbonyl)-amino]-1,1-bis-[3-(4-methoxycarbonylmethoxy-phenyl)-propyl]-piperidinium trifluoroacetate is kept in a moisture atmosphere for one week at room temperature. The resulting mixture of starting material and mono saponified ester is purified by preparative HPLC-MS (MeOH/H2O+0.1% TFA). LC (method L): $t_R$=1.07 min; Mass spectrum (ESI+): m/z=669 [M]+. IC50=0.165.

Example 8.1

3-[(3,5-Diamino-6-chloro-pyrazine-2-carbonyl)-amino]-1-(3-{4-[(2-dimethylaminoethylcarbamoyl)-methoxy]-phenyl}-propyl)-1-[3-(4-methoxycarbonylmethoxy-phenyl)-propyl]-piperidinium chloride hydrochloride

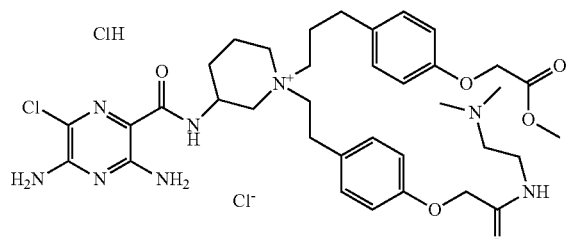

1-[3-(4-Carboxymethoxy-phenyl)-propyl]-3-[(3,5-diamino-6-chloro-pyrazine-2-carbonyl)-amino]-1-[3-(4-methoxycarbonylmethoxy-phenyl)-propyl]-piperidinium trifluoroacetate (78 mg, 0.1 mmol), 2-dimethylamino-ethylamine (10 mg, 0.11 mmol)) and N,N-Diisopropylethylamine (45 µl, 0.26 mmol) are dissolved in N,N-dimethylformamide (2 ml), 2-(1H-Benzotriazol-1-yl)-1,1,3,3-tetramethyluronium tetrafluoroborate (35 mg, 0.11 mmol) is added. The reaction is stirred at room temperature overnight. The resulting mixture is purified by preparative HPLC-MS (MeOH/H2O+0.1% TFA). 0.1 mL 1 M HCl is added to form chloride salt and solvent removed in vacuo. LC (method L): $t_R$=0.94 min; Mass spectrum (ESI+): m/z=370 [M]$^{++}$. IC50=0.085

Example 8.2

3-[(3,5-Diamino-6-chloro-pyrazine-2-carbonyl)-amino]-1-{3-[4-({2-[2-(2-hydroxy-ethoxy)ethoxy]-ethylcarbamoyl}-methoxy)-phenyl]-propyl}-1-[3-(4-methoxycarbonylmethoxy-phenyl)-propyl]-piperidinium chloride

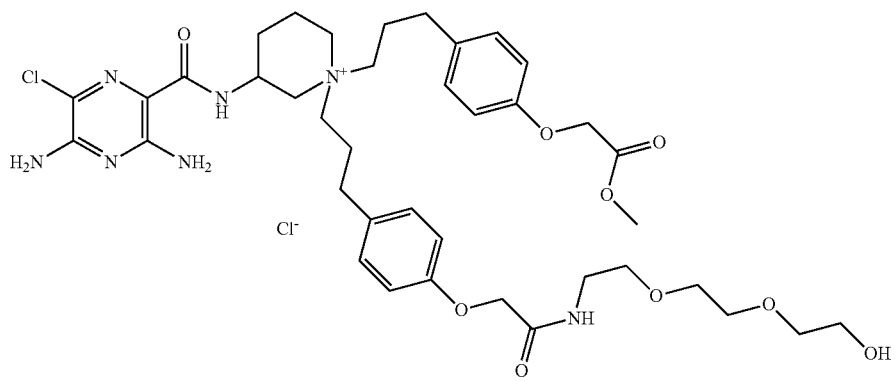 [SMILES: COC(=O)COc1ccc(CCC[N+]2(CCCc3ccc(OCC(=O)NCCOCCOCCO)cc3)CCCC(NC(=O)c3nc(Cl)c(N)nc3N)C2)cc1 ; [Cl-]]

The title compound is prepared from piperidine-3-yl-carbamic acid tert-butyl ester following a procedure analogous to that described for CCWAZU00596. Mass spectrum (ESI$^+$): m/z=800 [M+H]$^+$. IC50=0.37

Example 9

Intermediate 9.1: 3-Amino-1,1-bis-[3-(4-{2-[2-(2-hydroxy-ethoxy)-ethoxy]-ethoxy}-phenyl)propyl]-piperidinium chloride hydrochloride

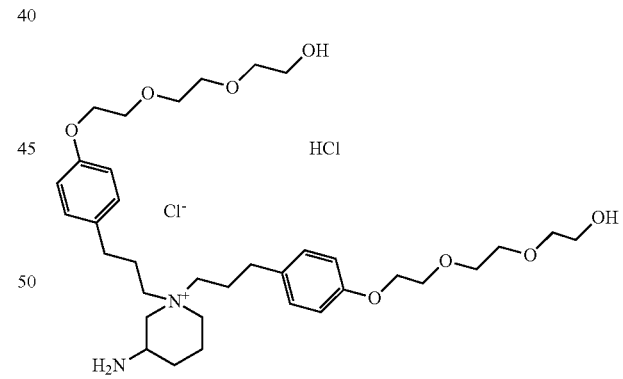

3-tert-Butoxycarbonylamino-1,1-bis-[3-(4-hydroxy-phenyl)-propyl]-piperidinium chloride (100 mg, 0.2 mmol), triethyleneglycol (1 ml, 7.5 mmol) and triphenylphosphane (110 mg, 0.41 mmol) are dissolved in THF (1 ml), diisopropyl-azodicarboxylate (85 µl, 0.4 mmol) is added and stirred for 5 h at 50° C. Additional triphenylphosphane (110 mg, 0.41 mmol) and diisopropyl-azodicarboxylate (85 µl, 0.4 mmol) are added and stirred at 50° C. overnight. The reaction mixture is evaporated and purified by preparative HPLC-MS (MeOH/H2O+0.1% TFA). The residue is dissolved in dichloromethane (1 ml) and TFA (1 ml), stirred at room temperature overnight and concentrated in vacuo. The residue is dissolved in methanol, 1M HCl (1 ml) is added and evaporated. LC (method L): $t_R$=0.94 min; Mass spectrum (ESI$^+$): m/z=633 [M]$^+$.

Table of analoges:

| Intermediate | Structure and name | ESI+ (M)+ | Rt | HPLC method |
|---|---|---|---|---|
| 9.1.1 | 3-Amino-1,1-bis-[3-(4-{2-[2-(2-hydroxy-ethoxy)-ethoxy]-ethoxy}-phenyl)-propyl]-piperidinium chloride hydrochloride | 633 | 0.94 | L |
| 9.1.2 | 3-Amino-1,1-bis-(3-{4-[2-(2-{2-[2-(2-hydroxy-ethoxy)-ethoxy]-ethoxy}-ethoxy)-ethoxy]-phenyl}-propyl)-piperidinium chloride hydrochloride | 405 (M + H)$^{++}$ | 1.00 | L |
| 9.1.3 | 3-Amino-1,1-bis-[3-(4-ethoxy-phenyl)-propyl]-piperidinium chloride hydrochloride | 425 | 1.12 | L |

-continued

Table of analoges:

| Intermediate | Structure and name | ESI+ (M)+ | Rt | HPLC method |
|---|---|---|---|---|
| 9.1.4 | 3-Amino-1,1-bis-{3-[4-(2-methoxy-ethoxy)-phenyl]-propyl}-piperidinium chloride hydrochloride | 485 | 1.00 | L |
| 9.1.5 | 3-Amino-1,1-bis-{3-[4-(2-{2-[2-(2-hydroxy-ethoxy)-ethoxy]-ethoxy}-ethoxy)-phenyl]-propyl}-piperidinium chloride hydrochloride | 721 | 0.98 | L |

Intermediate 9.1.6: (S)-3-tert-Butoxycarbonylamino-1,1-bis-[3-(4-carboxymethoxy-phenyl)-propyl]-piperidinium chloride

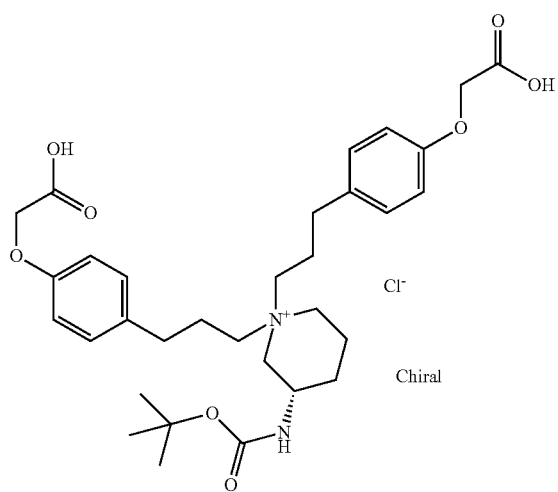 [SMILES: CC(C)(C)OC(=O)N[C@H]1CCC[N+](CCCc2ccc(OCC(=O)O)cc2)(CCCc2ccc(OCC(=O)O)cc2)C1 ; [Cl-]]

3-tert-Butoxycarbonylamino-1,1-bis-[3-(4-methoxycarbonylmethoxy-phenyl)-propyl]-piperidinium chloride (450 mg, 0.69 mmol) is dissolved in methanol (8 ml), 1 M sodium hydroxide solution (6 ml, 6 mmol) are added and stirred at room temperature overnight. The methanol is evaporated and the aqueous solution is acidified with 1 M HCl. The water phase is decanted from the oily product which is washed again with a small amount of water. The compound is dissolved in methanol and concentrated in vacuo. LC (method L): $t_R$=1.12 min; Mass spectrum (ESI$^+$): m/z=585 [M]$^+$.

Intermediate 9.1.7: (S)-3-tert-butoxycarbonylamino-1,1-bis-[3-(4-dimethylcarbamoylmethoxy-phenyl)propyl]-piperidinium trifluoroacetate

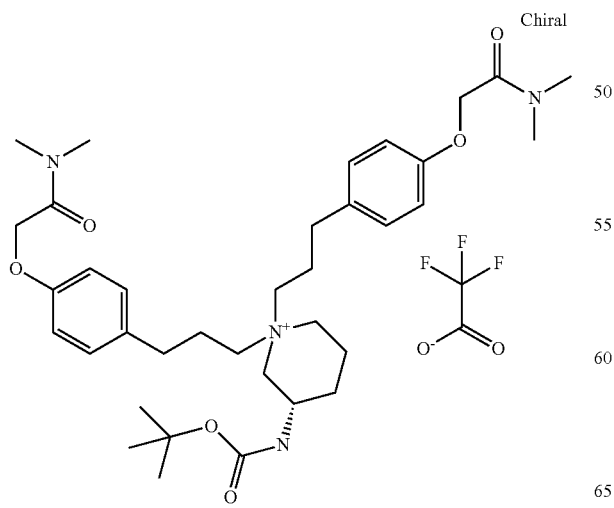

(S)-3-tert-Butoxycarbonylamino-1,1-bis-[3-(4-carboxymethoxy-phenyl)-propyl]-piperidinium chloride (460 mg, 0.73 mmol), 2 M dimethylamine solution in tetrahydrofurane (1 ml, 2 mmol)) and N,N-Diisopropylethylamine (400 μl, 2.29 mmol) are dissolved in N,N-dimethylformamide (15 ml), 2-(1H-Benzotriazol-1-yl)-1,1,3,3-tetramethyluronium tetrafluoroborate (481 mg, 1.5 mmol) is added. The reaction is stirred at room temperature overnight. The resulting mixture is purified by preparative HPLC-MS (MeOH/H2O+0.1% TFA). LC (method L): $t_R$=1.13 min; Mass spectrum (ESI$^+$): m/z=639 [M]$^+$.

Intermediate 9.1.8: 3-Amino-1,1-bis-{3-[4-(2-dimethylamino-ethoxy)-phenyl]-propyl}-piperidinium chloride dihydrochloride

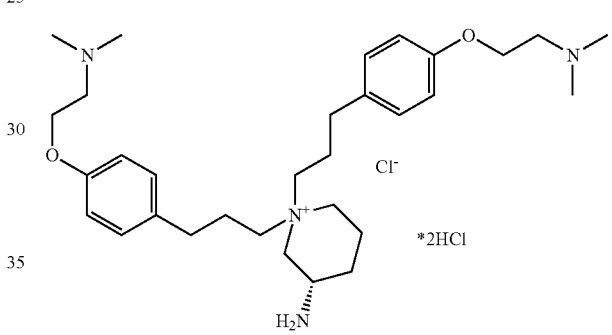

(S)-3-tert-butoxycarbonylamino-1,1-bis-[3-(4-dimethylcarbamoylmethoxy-phenyl)-propyl]-piperidinium trifluoroacetate (150 mg, 0.2 mmol) is dissolved in tetrahydrofurane (2 ml) and 4 M HCl (2 ml), stirred at 50° C. for 30 minutes and concentrated in vacuo. The residue is dissolved in dioxane (10 ml), a solution of lithiumaluminumhydydride (200 μl, 0.2 mmol) is added and stirred at room temperature for 2 h. 1 M HCl (1 ml) is added to the reaction mixture and concentrated in vacuo. LC (method L): $t_R$=0.63 min; Mass spectrum (ESI$^+$): m/z=511 [M]$^+$.

Example 9

3-[(3,5-Diamino-6-chloro-pyrazine-2-carbonyl)-amino]-1,1-bis-[3-(4-{2-[2-(2-hydroxyethoxy)-ethoxy]-ethoxy}-phenyl)-propyl]-piperidinium chloride

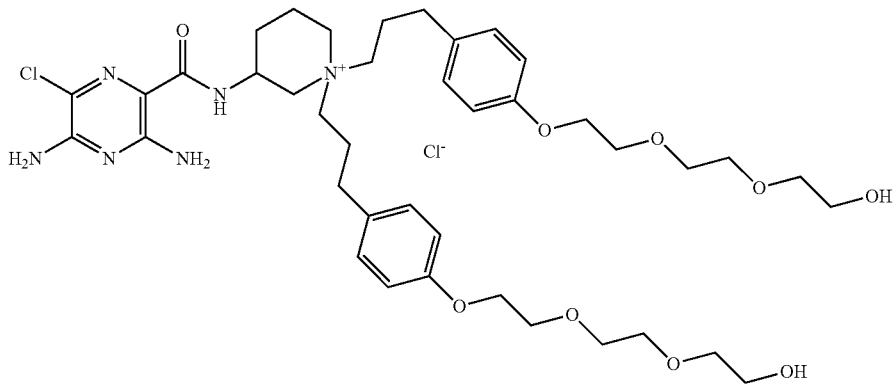 [SMILES: Nc1nc(N)c(C(=O)NC2CCC[N+](CCCc3ccc(OCCOCCOCCO)cc3)(CCCc3ccc(OCCOCCOCCO)cc3)C2)nc1Cl ; [Cl-]]

3-Amino-1,1-bis-[3-(4-{2-[2-(2-hydroxy-ethoxy)-ethoxy]-ethoxy}-phenyl)-propyl]-piperidinium chloride hydrochloride (60 mg, 0.068 mmol), 3,5-Diamino-6-chloro-pyrazine-2-carboxylic acid (14 mg, 0.073 mmol) and N,N-Diisopropylethylamine (120 μl, 0.69 mmol) are dissolved in N,N-dimethylformamide (2 ml), 2-(1H-Benzotriazol-1-yl)-1,1,3,3-tetramethyluronium tetrafluoroborate (22 mg, 0.069 mmol) is added. The reaction is stirred at room temperature overnight and purified by preparative HPLC-MS (MeOH/H2O+0.1% TFA). 0.1 mL 1 M HCl is added to form chloride salt and solvent removed in vacuo. LC (method L): $t_R$=1.09 min; Mass spectrum (ESI+): m/z=803 [M]+. IC50=0.095.

Table of analoges:

| Ex. | Structure and name | ESI+ (M)+ | Rt | HPLC method | IC50 |
|---|---|---|---|---|---|
| 9.1 | 3-[(3,5-Diamino-6-chloro-pyrazine-2-carbonyl)-amino]-1,1-bis-(3-{4-[2-(2-{2-[2-(2-hydroxy-ethoxy)-ethoxy]-ethoxy}-ethoxy)-ethoxy]-phenyl}-propyl)-piperidinium chloride | 979 | 1.14 | L | 0.111 |

-continued

Table of analoges:

| Ex. | Structure and name | ESI+ (M)+ | Rt | HPLC method | IC50 |
|---|---|---|---|---|---|
| 9.2 | 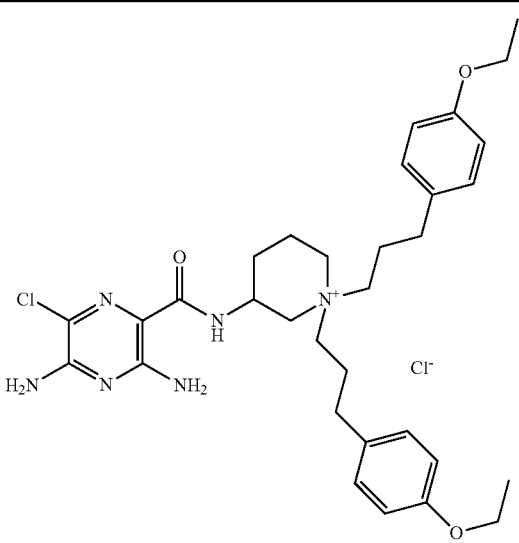<br>3-[(3,5-Diamino-6-chloro-pyrazine-2-carbonyl)-amino]-1,1-bis-[3-(4-ethoxy-phenyl)-propyl]-piperidinium chloride | 595 | 1.28 | L | 0.026 |
| 9.3 | 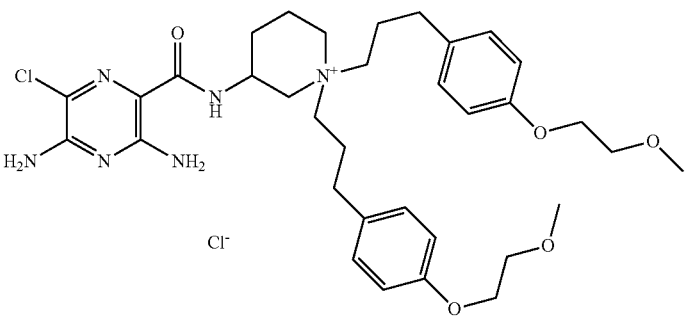 [SMILES: COCCOc1ccc(CCC[N+]2(CCCc3ccc(OCCOC)cc3)CCCC(NC(=O)c3nc(Cl)c(N)nc3N)C2)cc1 ; [Cl-]]<br>3-[(3,5-Diamino-6-chloro-pyrazine-2-carbonyl)-amino]-1,1-bis-{3-[4-(2-methoxy-ethoxy)-phenyl]-propyl}-piperidinium chloride | 655 | 1.16 | L | 0.022 |
| 9.4 | 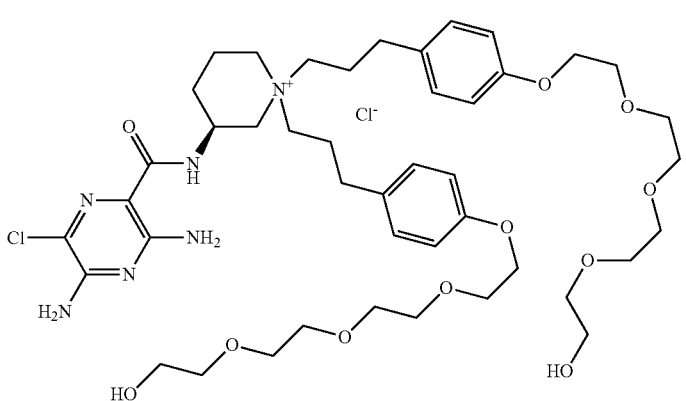 [SMILES: Nc1nc(N)c(C(=O)N[C@H]2CCC[N+](CCCc3ccc(OCCOCCOCCOCCO)cc3)(CCCc3ccc(OCCOCCOCCOCCO)cc3)C2)nc1Cl ; [Cl-]]<br>3-[(3,5-Diamino-6-chloro-pyrazine-2-carbonyl)-amino]-1,1-bis-{3-[4-(2-{2-[2-(2-hydroxy-ethoxy)-ethoxy]-ethoxy}-ethoxy)-phenyl]-propyl}-piperidinium chloride | 891 | 1.12 | L | 0.067 |

| Ex. | Structure and name | ESI+ (M)+ | Rt | HPLC method | IC50 |
|---|---|---|---|---|---|
| 9.5 | 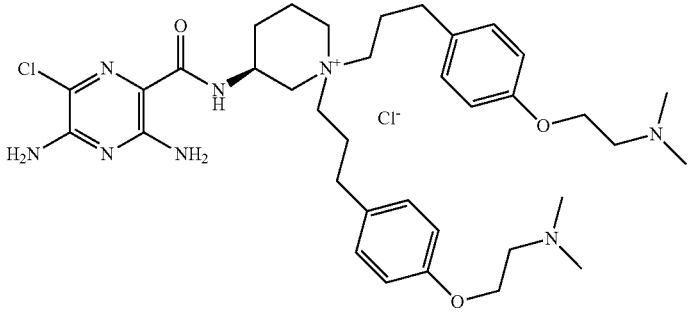 [SMILES: CN(C)CCOc1ccc(CCC[N+]2(CCCc3ccc(OCCN(C)C)cc3)CCC[C@H](NC(=O)c3nc(Cl)c(N)nc3N)C2)cc1 ; [Cl-]]

3-[(3,5-Diamino-6-chloro-pyrazine-2-carbonyl)-amino]-
1,1-bis-{3-[4-(2-dimethylamino-ethoxy)-phenyl]-propyl}-
piperidinium chloride dihydrochloride | 681 | 0.79 | L | 0.063 |

Example 9.6

(S)-3-[(3,5-Diamino-6-chloro-pyrazine-2-carbonyl)-amino]-1,1-bis-{3-[4-(2-hydroxyethoxy)-phenyl]-propyl}-piperidinium chloride

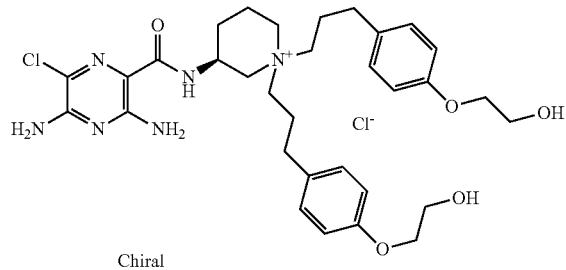 [SMILES: Nc1nc(N)c(C(=O)N[C@H]2CCC[N+](CCCc3ccc(OCCO)cc3)(CCCc3ccc(OCCO)cc3)C2)nc1Cl ; [Cl-]]

Chiral (S)-1,1-Bis-[3-(4-carboxymethoxy-phenyl)-propyl]-3-[(3,5-diamino-6-chloro-pyrazine-2-carbonyl)amino]-piperidinium chloride (50 mg, 0.072 mmol) is dissolved in tetrahydrofurane (1 ml), N,N-carbonyldiimidazole (25 mg, 0.154 mmol) is added and stirred for 30 minutes at 40° C. The reaction fixture is cooled to room temperature, a sodium borohydride (15 mg, 0.4 mmol) in water (100 μl) is added and stirred at room temperature for 1 h. Then 1 M HCl (0.4 ml 0.4 mmol) is added and the resulting mixture is purified by preparative HPLC-MS (MeOH/H2O+0.1% TFA). 0.1 mL 1 M HCl is added to form chloride salt and solvent removed in vacuo. LC (method L): $t_R$=1.00 min; Mass spectrum (ESI+): m/z=627 [M]+. IC50=0.038.

Example 10

Intermediate 10.1: 3-Amino-1,1-bis-[3-(3-methoxy-phenyl)-propyl]-piperidinium chloride hydrochloride

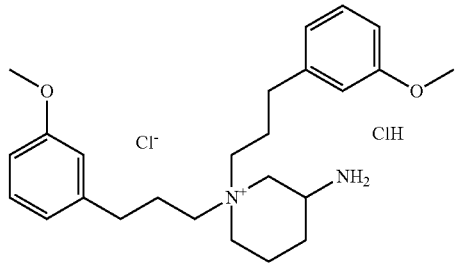 [SMILES: COc1cccc(CCC[N+]2(CCCc3cccc(OC)c3)CCCC(N)C2)c1 ; [Cl-] ; Cl]

Piperidin-3-yl-carbamic acid tert-butyl ester (110 mg, 0.55 mmol) and 1-(3-Bromo-propyl)-3-methoxy-benzene (320 mg, 1.4 mmol), potassium carbonate (100 mg, 0.72 mmol) and sodium iodide (150 mg, 1 mmol) are dissolved in acetonitril (2 ml) and stirred at reflux overnight and purified by preparative HPLC-MS (MeOH/H2O+0.1% TFA). The residue is dissolved in dichloromethane (1 ml) and TFA (1 ml), stirred at room temperature for 1 h and concentrated in vacuo. The residue is dissolved in acetonitril, 1M HCl (1 ml) is added and evaporated. LC (method L): $t_R$=1.02 min; Mass spectrum (ESI$^+$): m/z=397 [M]$^+$.

| Inter-mediate | Structure and name | ESI+ (M)+ | Rt | HPLC method |
|---|---|---|---|---|
| 10.1.1 | 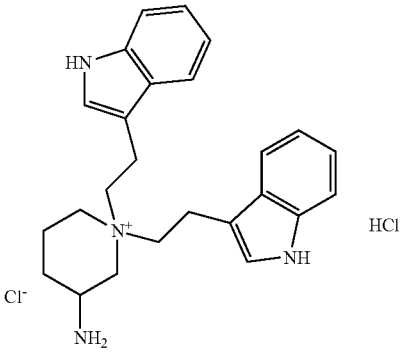 [SMILES: [Cl-] ; NC1CCC[N+](CCc2c[nH]c3ccccc23)(CCc2c[nH]c3ccccc23)C1 ; Cl]<br>3-Amino-1,1-bis-[2-(1H-indol-3-yl)-ethyl]-piperidinium chloride hydrochloride | 387 | 0.93 | L |
| 10.1.2 | 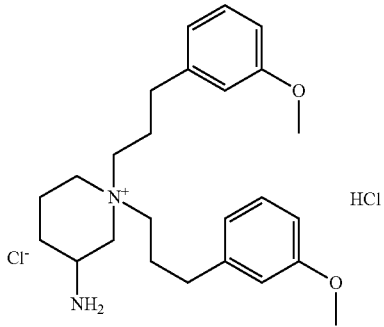 [SMILES: [Cl-] ; COc1cccc(CCC[N+]2(CCCc3cccc(OC)c3)CCCC(N)C2)c1 ; Cl]<br>3-Amino-1,1-bis-[3-(3-methoxy-phenyl)-propyl]-piperidinium chloride hydrochloride | 397 | 1.02 | L |
| 10.1.3 | 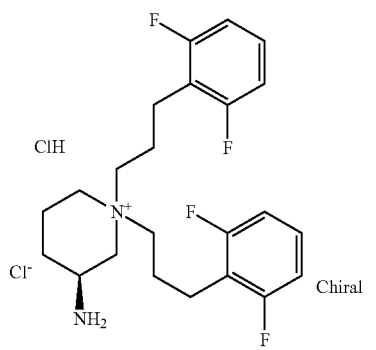<br>3-Amino-1,1-bis-[3-(2,6-difluoro-phenyl)-propyl]-piperidinium chloride hydrochloride | 409 | 1.02 | L |
Table of analoges:

-continued
Table of analoges:
| Intermediate | Structure and name | ESI+ (M)+ | Rt | HPLC method |
|---|---|---|---|---|
| 10.1.4 | 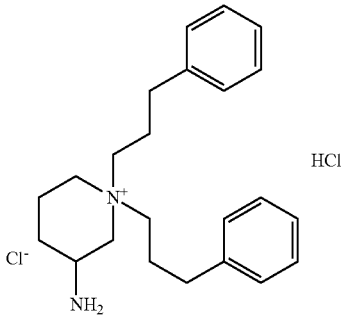 [SMILES: [Cl-] ; NC1CCC[N+](CCCc2ccccc2)(CCCc2ccccc2)C1 ; Cl]<br>3-Amino-1,1-bis-[3-(3-phenyl)-propyl]-piperidinium chloride hydrochloride | 337 | 1.01 | L |
| 10.1.5 | 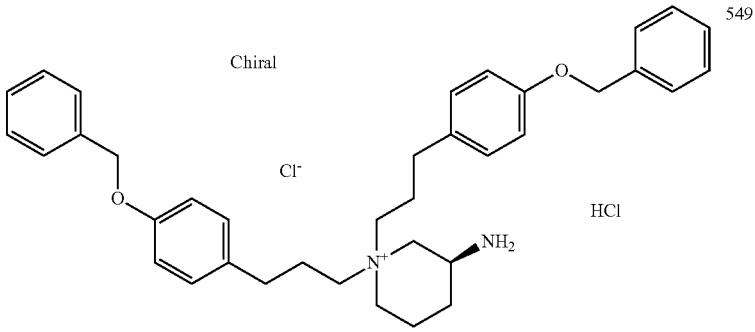<br>3-Amino-1,1-bis-[3-(4-benzyloxy-phenyl)-propyl]-piperidinium chloride hydrochloride | 549 | 1.31 | L |
| 10.1.6 | 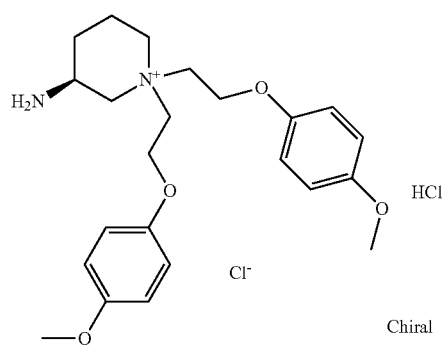 [SMILES: COc1ccc(OCC[N+]2(CCOc3ccc(OC)cc3)CCC[C@H](N)C2)cc1 ; [Cl-] ; Cl]<br>3-Amino-1,1-bis-[2-(4-methoxy-phenoxy)-ethyl]-piperidinium chloride hydrochloride | 401 | 0.92 | L |

Table of analoges:

| Intermediate | Structure and name | ESI+ (M)+ | Rt | HPLC method |
|---|---|---|---|---|
| 10.1.7 | 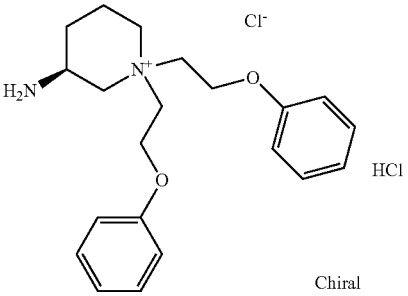 [SMILES: N[C@H]1CCC[N+](CCOc2ccccc2)(CCOc2ccccc2)C1 ; [Cl-] ; Cl]<br>3-Amino-1,1-bis-[2-phenoxy-ethyl]-piperidinium chloride hydrochloride (Chiral) | 341 | 0.91 | L |
| 10.1.8 | 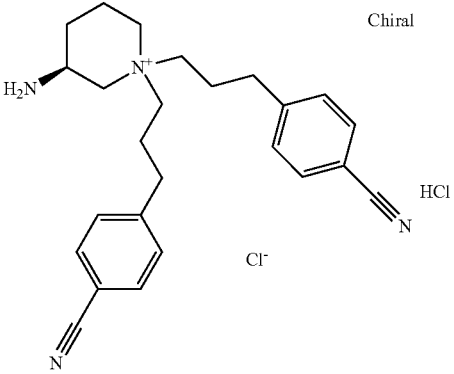 [SMILES: N#Cc1ccc(CCC[N+]2(CCCc3ccc(C#N)cc3)CCC[C@H](N)C2)cc1 ; [Cl-] ; Cl]<br>3-Amino-1,1-bis-[3-(4-cyano-phenyl)-propyl]-piperidinium chloride hydrochloride (Chiral) | 387 | 0.82 | L |

The following analogues are prepared in analogy to Example 1:

| Ex. | Structure and name | ESI+ (M)+ | Rt | HPLC method | IC50 [µM] |
|---|---|---|---|---|---|
| 10.1 | 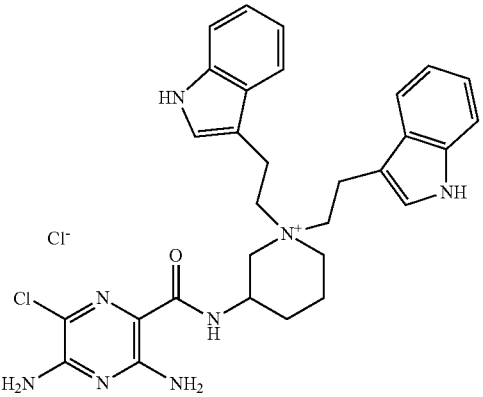 [SMILES: Nc1nc(N)c(C(=O)NC2CCC[N+](CCc3c[nH]c4ccccc34)(CCc3c[nH]c4ccccc34)C2)nc1Cl ; [Cl-]]<br>3-[(3,5-Diamino-6-chloro-pyrazine-2-carbonyl)-amino]-1,1-bis-[2-(1H-indol-3-yl)-ethyl]-piperidinium chloride | 557 | 1.12 | L | 0.140 |

-continued

| Ex. | Structure and name | ESI+ (M)+ | Rt | HPLC method | IC50 [μM] |
|---|---|---|---|---|---|
| 10.2 | 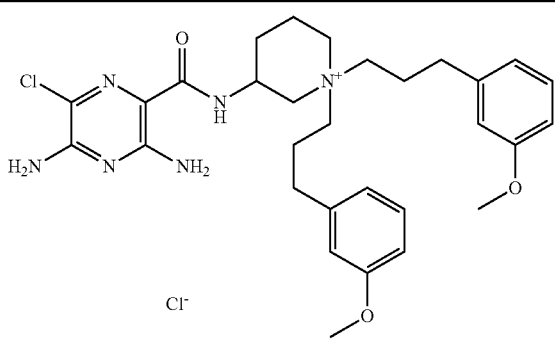<br>3-[(3,5-Diamino-6-chloro-pyrazine-2-carbonyl)-amino]-1,1-bis-[3-(3-methoxy-phenyl)-propyl]-piperidinium chloride | 567 | 1.19 | L | 0.027 |
| 10.3 | 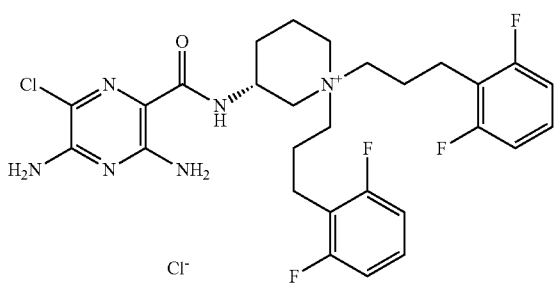 [SMILES: Nc1nc(N)c(C(=O)N[C@@H]2CCC[N+](CCCc3c(F)cccc3F)(CCCc3c(F)cccc3F)C2)nc1Cl ; [Cl-]]<br>3-[(3,5-Diamino-6-chloro-pyrazine-2-carbonyl)-amino]-1,1-bis-[3-(2,6-difluoro-phenyl)-propyl]-piperidinium chloride | 579 | 1.20 | L | 0.047 |
| 10.4 | 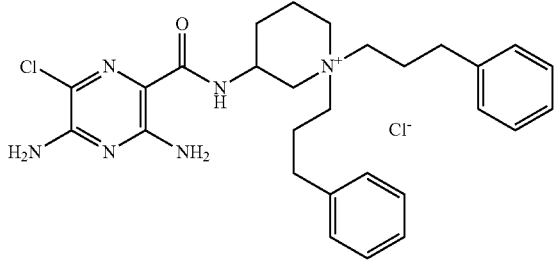 [SMILES: Nc1nc(N)c(C(=O)NC2CCC[N+](CCCc3ccccc3)(CCCc3ccccc3)C2)nc1Cl ; [Cl-]]<br>3-[(3,5-Diamino-6-chloro-pyrazine-2-carbonyl)-amino]-1,1-bis-(3-phenyl-propyl)-piperidinium chloride | 507 | 1.20 | L | 0.015 |
| 10.5 | 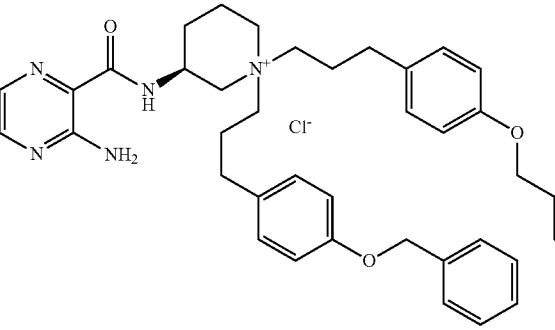<br>1,1-Bis-[3-(4-benzyloxy-phenyl)-propyl]-3-[(3,5-diamino-6-chloro-pyrazine-2-carbonyl)-amino]-piperidinium chloride | 721 | 1.44 | L | |

| Ex. | Structure and name | ESI+ (M)+ | Rt | HPLC method | IC50 [µM] |
|---|---|---|---|---|---|
| 10.6 | 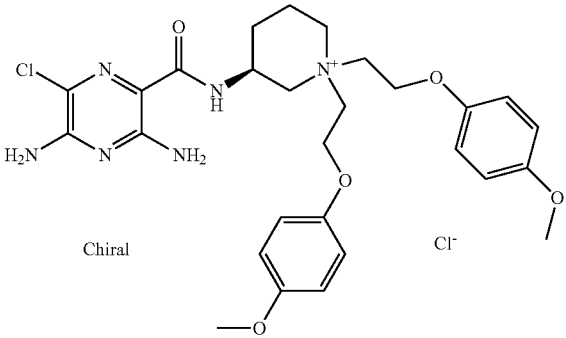 [SMILES: COc1ccc(OCC[N+]2(CCOc3ccc(OC)cc3)CCC[C@H](NC(=O)c3nc(Cl)c(N)nc3N)C2)cc1 ; [Cl-]]<br>3-[(3,5-Diamino-6-chloro-pyrazine-2-carbonyl)-amino]-1,1-bis-[2-(4-methoxy-phenoxy)-ethyl]-piperidinium chloride | 571 | 1.15 | L | 0.104 |
| 10.7 | 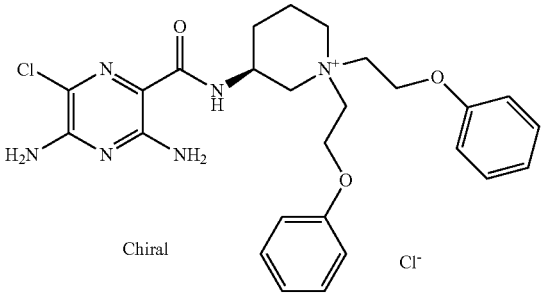 [SMILES: Nc1nc(N)c(C(=O)N[C@H]2CCC[N+](CCOc3ccccc3)(CCOc3ccccc3)C2)nc1Cl ; [Cl-]]<br>3-[(3,5-Diamino-6-chloro-pyrazine-2-carbonyl)-amino]-1,1-bis-[2-phenoxy-ethyl]-piperidinium chloride | 511 | 1.16 | L | 0.158 |
| 10.8 | 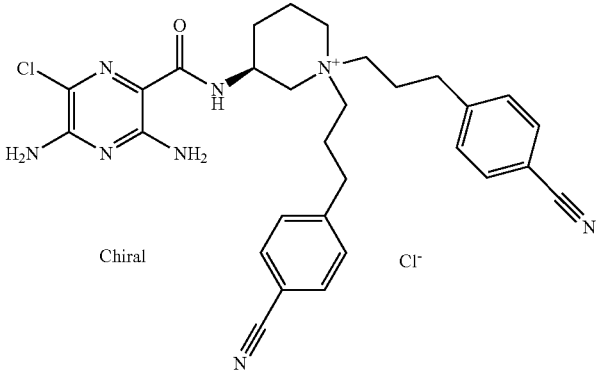 [SMILES: N#Cc1ccc(CCC[N+]2(CCCc3ccc(C#N)cc3)CCC[C@H](NC(=O)c3nc(Cl)c(N)nc3N)C2)cc1 ; [Cl-]]<br>1,1-Bis-[3-(4-cyano-phenyl)-propyl]-3-[(3,5-diamino-6-chloro-pyrazine-2-carbonyl)-amino]-piperidinium chloride | 557 | 1.03 | L | 0.034 |

Example 10.9

3-[(3,5-Diamino-6-chloro-pyrazine-2-carbonyl)-amino]-1,1-bis-[3-(3-hydroxy-phenyl)propyl]-piperidinium chloride

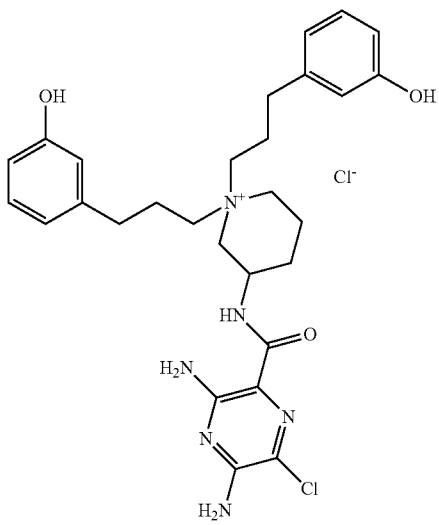 [SMILES: Nc1nc(N)c(C(=O)NC2CCC[N+](CCCc3cccc(O)c3)(CCCc3cccc(O)c3)C2)nc1Cl ; [Cl-]]

3-[(3,5-Diamino-6-chloro-pyrazine-2-carbonyl)-amino]-1,1-bis-[3-(3-methoxy-phenyl)-propyl]-piperidinium chloride (60 mg, 0.089 mmol) in dichloromethane (1 ml) are cooled to −15° C., borontribromide (0.2 ml, 1.16 mmol) is added dropwise, the reaction is allowed to warm to room temperature and stirred for 1 h. Then methanol (2 ml) is added dropwise and the reaction mixture is evaporated. The residue is purified by preparative HPLC-MS (MeOH/H2O+0.1% TFA). 0.1 mL 1 M HCl is added to form chloride salt and solvent removed in vacuo. LC (method L): $t_R$=1.01 min; Mass spectrum (ESI$^+$): m/z=539 [M]$^+$. IC50=0.013.

Example 10.10

Intermediate 10.1.9: (S)-3-tert-Butoxycarbonylamino-1,1-bis-[3-(3-methoxy-phenyl)-propyl]-piperidinium hydroxide

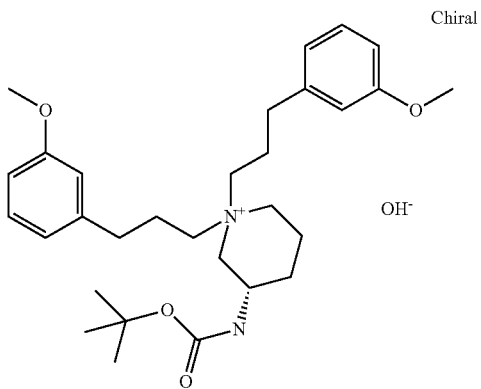

(S)-Piperidin-3-yl-carbamic acid tert-butyl ester (2.72 g, 13.6 mmol) and 1-(3-Bromo-propyl)-3-methoxy-benzene (6.6 g, 28.8 mmol), potassium carbonate (2.5 g, 18 mmol) and sodium iodide (4 g, 26.7 mmol) are dissolved in acetonitril (40 ml) and stirred at reflux for 1 day and the solvent is removed under vacuo. The residue is taken up in dichloromethane, filtered through a pad of silica, washed with a mixture of dichloromethane: methanol:conc.ammonia=4:1: 0.1 and the filtrate is evaporated. LC (method L): $t_R$=1.30 min; Mass spectrum (ESI$^+$): m/z=497 [M]$^+$.

Intermediate 1.1.10: (S)-3-Amino-1,1-bis-[3-(3-hydroxy-phenyl)-propyl]-piperidinium bromide hydrobromide

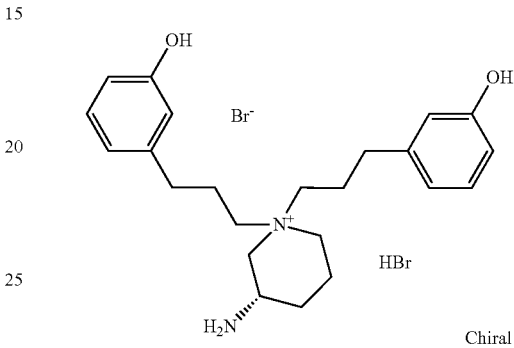

(S)-3-tert-Butoxycarbonylamino-1,1-bis-[3-(3-methoxyphenyl)-propyl]-piperidinium trifluoroacetate (6.16 g, 12 mmol) in dichloromethane (50 ml) are cooled to −15° C., 1 M borontribromide solution in dichloromethane (40 ml, 40 mmol) is added dropwise, the reaction is allowed to warm to room temperature and stirred for 1 hour. Then methanol (30 ml) is added dropwise and the reaction mixture is stirred at room temperature over night and evaporated. LC (method L): $t_R$=0.77 min; Mass spectrum (ESI$^+$): m/z=369 [M]$^+$.

Intermediate 10.1.11

(S)-3-tert-Butoxycarbonylamino-1,1-bis-[3-(3-hydroxy-phenyl)-propyl]-piperidinium bromide

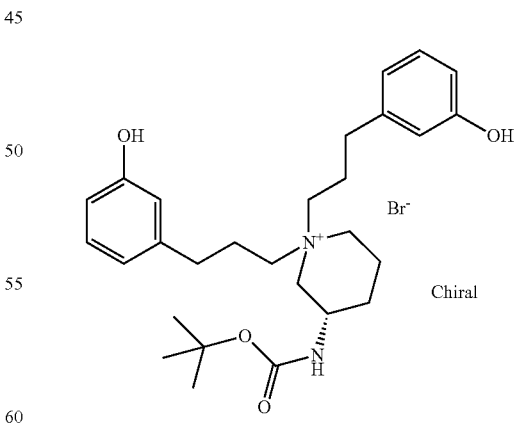

A solution of di-tert.butyl dicarbonate (2.45 g, 11.2 mmol) in dichloromethane (20 ml) is added dropwise to a solution of (S)-3-Amino-1,1-bis-[3-(3-hydroxy-phenyl)-propyl]-piperidinium bromide hydrobromide (5.85 g, 11 mmol) and triethylamine (2.3 ml, 16.5 mmol) in methanol (20 ml) at 0° C. and stirred at this temperature for 30 min. The reaction is allowed to warm to room temperature, stirred overnight and concentrated in vacuo. LC (method L): $t_R$=1.11 min; Mass spectrum (ESI$^+$): m/z=469 [M]$^+$.

Intermediate 10.1.12: (S)-3-tert-Butoxycarbonylamino-1,1-bis-[3-(3-methoxycarbonylmethoxy-phenyl)propyl]-piperidinium bromide

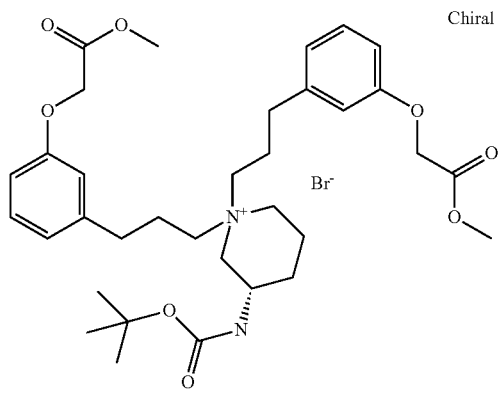 [SMILES: COC(=O)COc1cccc(CCC[N+]2(CCCc3cccc(OCC(=O)OC)c3)CCC[C@H](NC(=O)OC(C)(C)C)C2)c1 ; [Br-]]

Bromo-acetic acid methylester is added to a suspension of (S)-3-tert-Butoxycarbonylamino-1,1-bis-[3-(–hydroxy-phenyl)-propyl]-piperidinium bromide (550 mg, 1.0 mmol) and potassium carbonate (500 mg, 3.6 mmol) in DMF (5 ml), stirred for 2 h at room temperature and concentrated in vacuo. Water is added to the residue and extracted with dichloromethane. The organic phase is washed with water, dried over Na$_2$SO$_4$ and concentrated in vacuo. LC (method L): $t_R$=1.25 min; Mass spectrum (ESI$^+$): m/z=613 [M]$^+$.

Intermediate 10.1.13: (S)-3-Amino-1,1-bis-[3-(3-methoxycarbonylmethoxy-phenyl)-propyl]-piperidinium chloride hydrochloride

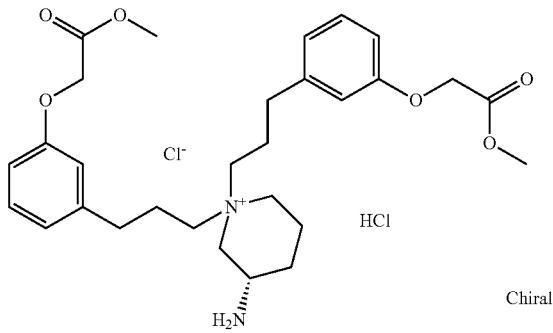 [SMILES: COC(=O)COc1cccc(CCC[N+]2(CCCc3cccc(OCC(=O)OC)c3)CCC[C@H](N)C2)c1 ; [Cl-] ; Cl]

(S)-3-tert-Butoxycarbonylamino-1,1-bis-[3-(3-methoxycarbonylmethoxy-phenyl)-propyl]-piperidinium bromide (707 mg, 1.0 mmol) is dissolved in dichloromethane (1 ml) and trifluoroacetic acid (1 ml) and stirred at room temperature overnight. The mixture is evaporated, dissolved in acetonitrile and 1 M HCl (5 ml) and evaporated again. LC (method L): $t_R$=0.99 min; Mass spectrum (ESI$^+$): m/z=513 [M]$^+$.

Example 10.10

(S)-3-[(3,5-Diamino-6-chloro-pyrazine-2-carbonyl)-amino]-1,1-bis-[3-(3-methoxycarbonylmethoxy-phenyl)-propyl]-piperidinium chloride

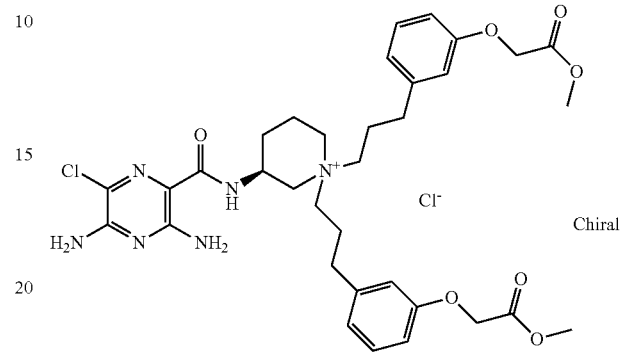

(S)-3-Amino-1,1-bis-[3-(3-methoxycarbonylmethoxy-phenyl)-propyl]-piperidinium chloride hydrochloride (60 mg, 0.1 mmol), 3,5-Diamino-6-chloro-pyrazine-2-carboxylic acid (22 mg, 0.115 mmol) and N,N-Diisopropylethylamine (75 µl, 0.43 mmol) are dissolved in N,N-dimethylformamide (2 ml), 2-(1H-Benzotriazol-1-yl)-1,1,3,3-tetramethyluronium tetrafluoroborate (34 mg, 0.106 mmol) is added. The reaction is stirred at room temperature overnight and purified by preparative HPLC-MS (MeOH/H2O+0.1% TFA). LC (method L): $t_R$=1.15 min; Mass spectrum (ESI$^+$):

m/z=683 [M]$^+$. IC50=0.025 µM

Intermediate 10.1.14: (S)-1,1-Bis-[3-(3-carboxymethoxy-phenyl)-propyl]-3-[(3,5-diamino-6-chloro-pyrazine-2-carbonyl)-amino]-piperidinium chloride

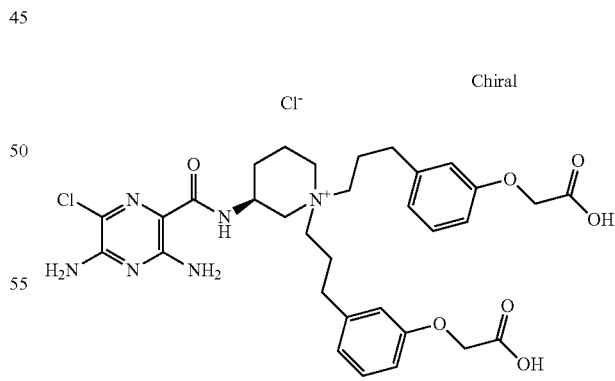

(S)3-[(3,5-Diamino-6-chloro-pyrazine-2-carbonyl)-amino]-1,1-bis-[3-(3-methoxycarbonylmethoxy-phenyl)-propyl]-piperidinium trifluoroacetate (2.67 g, 3.8 mmol)) is dissolved in dioxane (20 ml) and 6N HCl (20 ml, 120 mmol) and stirred at room temperature for 3 days and solvent is removed in vacuo. LC (method L)): $t_R$=1.06 min; Mass spectrum (ESI$^+$): m/z=655 [M]$^+$.

Example 10.11

(S)-3-[(3,5-Diamino-6-chloro-pyrazine-2-carbonyl)-amino]-1,1-bis-[3-(3-{[(1-methyl-1H-imidazol-2-ylmethyl)-carbamoyl]-methoxy}-phenyl)-propyl]-piperidinium hydroxide

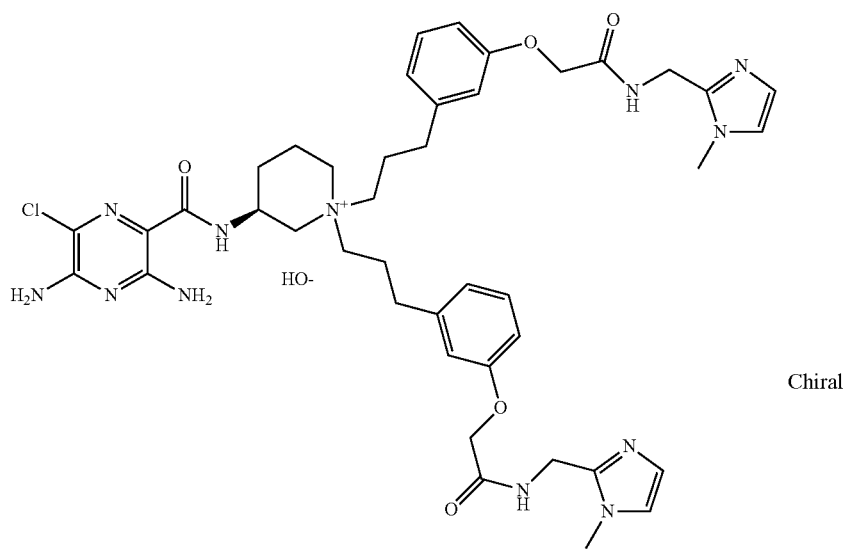

Chiral (S)-1,1-Bis-[3-(3-carboxymethoxy-phenyl)-propyl]-3-[(3,5-diamino-6-chloro-pyrazine-2-carbonyl)amino]-piperidinium chloride (100 mg, 0.13 mmol),), C-(1-Methyl-1H-imidazol-2-yl)-methylamine (53 mg, 0.29 mmol) and N,N-Diisopropylethylamine (225 µl, 1.3 mmol) are dissolved in N,N-dimethylformamide (3.5 ml), 2-(1H-Benzotriazol-1-yl)-1,1,3,3-tetramethyluronium tetrafluoroborate (93 mg, 0.29 mmol) is added. The reaction is stirred at room temperature overnight and purified by preparative HPLC-MS (MeOH/H$_2$O+0.1% TFA). The product is dissolved in dichloromethane, washed with a 2 molar potassiumcarbonate solution, dried over sodiumsulfate and concentrated in vacuo. LC (method L): $t_R$=1.15 min; Mass spectrum (ESI$^+$): m/z=841 [M]$^+$. IC50=0.007

Table of analoges:
| Ex. | STRUCTURE and NAME | HPLC-MS method | Rt | [M]+ |
|---|---|---|---|---|
| 10.12 | 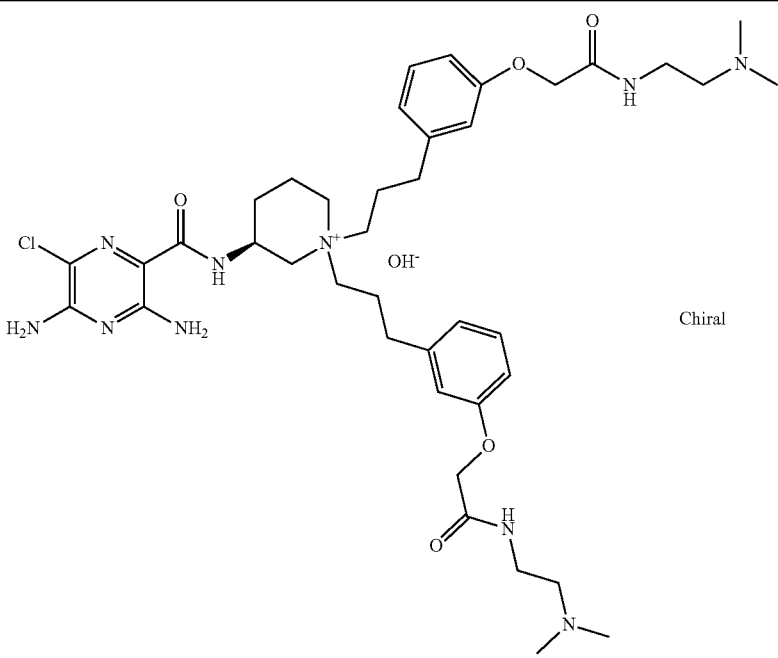 3-[(3,5-Diamino-6-chloro-pyrazine-2-carbonyl)-amino]-1,1-bis-(3-{3-[(2-dimethylamino-ethylcarbamoyl)-methoxy]-phenyl}-propyl)-piperidinium hydroxide | N | 1.14 | 795 |
| 10.13 | 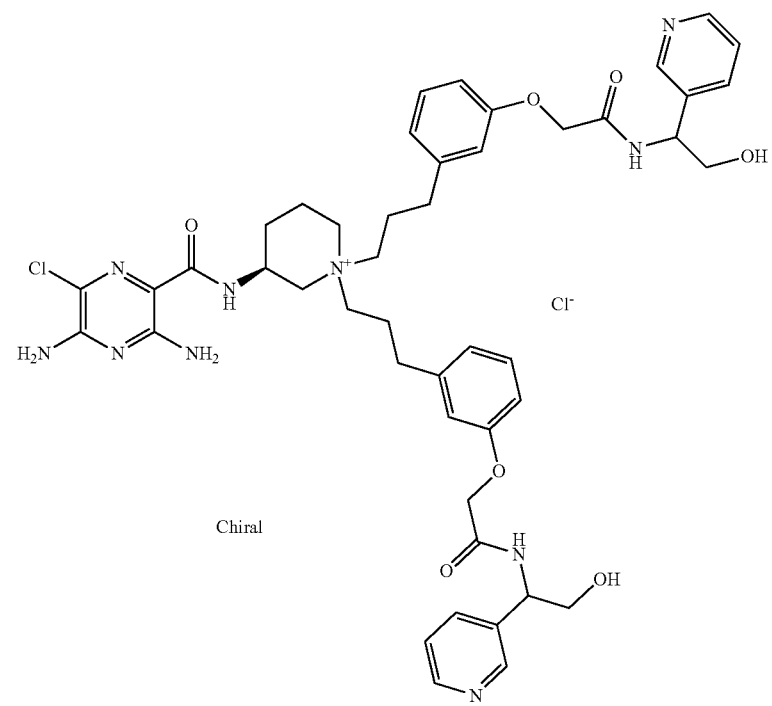 [SMILES: Nc1nc(N)c(C(=O)N[C@H]2CCC[N+](CCCc3cccc(OCC(=O)NC(CO)c4cccnc4)c3)(CCCc3cccc(OCC(=O)NC(CO)c4cccnc4)c3)C2)nc1Cl ; "Chiral" ; [Cl-]] 3-[(3,5-Diamino-6-chloro-pyrazine-2-carbonyl)-amino]-1,1-bis-(3-{3-[(2-hydroxy-1-pyridin-3-yl-ethylcarbamoyl)-methoxy]-phenyl}-propyl)-piperidinium chloride | N | 1.15 | 895 |

Example 11

1-(4-Benzyloxy-benzyl)-3-[3,5-diamino-6-chloropyrazine-2-carbonyl)-amino]-1-azonia[2.2.2]octane chloride

Intermediate 11.1.1

3,5-Diamino-6-chloropyrazine-2-carboxylic acid

Methyl-3,5-diamino-6-chloropyrazine-2-carboxylate (8.5 g, 41.9 mmol) is dissolved in dioxane (200 mL), sodium hydroxide (1 M in water, 125 mL, 125 mmol) added and the mixture stirred overnight at room temperature. The reaction mixture is acidified to pH 5 with 4 M hydrochloric acid and concentrated to one third of the initial volume. The resulting solid is collected by filtration, washed with water and dried under vacuum at 50° C. Yield: 7.4 g ESI mass spectrum: [M+H]$^+$=189
Retention time HPLC: 0.23 min (Method B)

Intermediate 11.1.2

3,5-Diamino-6-chloropyrazine-2-carboxylic-acid(1-aza-bicyclo[2.2.2]oct-3-yl)-amide A solution of 3,5-diamino-6-chloropyrazine-2-carboxylic acid (Intermediate 1.1.1, 2.50 g, 13.1 mmol), 1-aza-bicyclo[2.2.2]oct-3-ylamine dihydrochloride (2.87 g, 14.4 mmol), O-(benzotriazol-1-yl)-N,N,N',N'-tetramethyluronium tetrafluoroborate (4.62 g, 14.4 mmol) and triethylamine (6.72 mL, 39.3 mmol) in dry N,N-dimethylformamide (25 mL) is stirred overnight at room temperature under nitrogen atmosphere. The resulting solid is collected by filtration, washed with diethyl ether and dried at 50° C. under vacuum.

Yield: 2.55 g.
ESI mass spectrum: [M+H]$^+$=297
Retention time HPLC: 0.51 min (Method B)

Example 11

1-(4-Benzyloxy-benzyl)-3-[3,5-diamino-6-chloropyrazine-2-carbonyl)-amino]-1-azonia[2.2.2]octane chloride

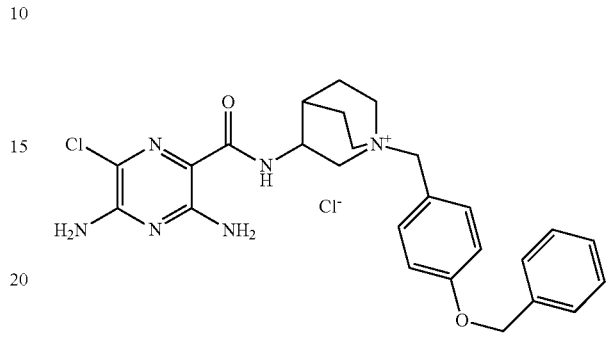

To a solution of 3,5-diamino-6-chloropyrazine-2-carboxylic-acid(1-aza-bicyclo[2.2.2]oct-3-yl)-amide (Intermediate 1.1.2, 50.0 mg, 0.17 mmol) and benzyloxybenzyl chloride (58.8 mg, 0.25 mmol) in DMSO (1 mL), potassium carbonate (23.3 mg, 0.17 mmol) and sodium iodide (6.3 mg, 0.04 mmol) are added and the mixture stirred overnight at room temperature. Water (0.5 mL) is added and the mixture purified via preparative reverse phase HPLC (gradient of acetonitrile in water+0.05% trifluoroacetic acid). Fractions containing the title compound are collected and evaporated under reduced pressure. The residue is triturated with a 2 M solution of HCl in diethyl ether (2 mL) and then dried at 50° C. under vacuum.

Yield: 47 mg
ESI mass spectrum: [M]$^+$=493
Retention time HPLC: 9.66 min (Method C)

The examples in the following table are prepared according to the method described for Example 11, employing in the alkylation step the corresponding alkyl or benzyl halides instead of benzyloxybenzyl chloride.

| Ex. | STRUCTURE | HPLC-MS Method | Rt | [M]+ |
|---|---|---|---|---|
| 11.1 | 3-[(3,5-Diamino-6-chloro-pyrazine-2-carbonyl)-amino]-1-[3-(4-methoxy-phenyl)-propyl]-1-azonia-bicyclo[2.2.2]octane | C | 8.57 | 455 |

-continued

| Ex. | STRUCTURE | HPLC-MS Method | Rt | [M]+ |
|---|---|---|---|---|
| 11.2 | 1-[3-(4-Chloro-phenyl)-propyl]-3-[(3,5-diamino-6-chloro-pyrazine-2-carbonyl)-amino]-1-azonia-bicyclo[2.2.2]octane chloride | C | 9.37 | 449 |
| 11.3 | 1-Benzyl-3-[(3,5-diamino-6-chloro-pyrazine-2-carbonyl)-amino]-1-azonia-bicyclo[2.2.2]octane chloride | C | 7.66 | 387 |
| 11.4 | 3-[(3,5-Diamino-6-chloro-pyrazine-2-carbonyl)-amino]-1-(3-phenyl-propyl)-1-azonia-bicyclo[2.2.2]octane chloride | C | 8.37 | 415 |
| 11.5 | 3-[(3,5-Diamino-6-chloro-pyrazine-2-carbonyl)-ammo]-1-(4-methoxycarbonyl-benzyl)-1-azonia-bicyclo[2.2.2]oclane chloride | C | 7.80 | 445 |

Example 12

3-[(3,5-Diamino-6-chloro-pyrazine-2-carbonyl)-amino]-1-ethoxycarbonylmethyl-1-[3-(4-methoxy-phenyl)-propyl]-piperidinium chloride Intermediate 12.1.1

(3-tert-Butoxycarbonylamino-piperidin-1-yl)-acetic acid ethyl ester

To a solution of piperidin-3-yl-carbamic acid tert-butyl ester hydrochloride (1.0 g, 4.2 mmol) and ethyl iodoacetate (0.99 g, 4.6 mmol) in acetonitrile (30 mL) is added $K_2CO_3$ (1.5 g, 10.5 mmol) and the mixture stirred overnight at room temperature. Volatiles are evaporated under reduced pressure and the residue taken up with water and extracted twice with ethyl acetate. The organic phase is dried over $MgSO_4$ and evaporated under reduced pressure. The resulting material is purified via chromatography over silica gel eluting with a mixture of EtOAc/MeOH (95:5 v/v). Yield: 0.8 g.

ESI mass spectrum: $[M+H]^+=287$

Retention time HPLC: 0.69 min (Method A)

Intermediate 12.1.2

3-Amino-1-ethoxycarbonylmethyl-1-[3-(4-methoxy-phenyl)-propyl]-piperidinium bromide trifluoroacetate salt To a solution of (3-tert-butoxycarbonylamino-piperidin-1-yl)-acetic acid ethyl ester (Intermediate 3.1.1, 800 mg, 2.3 mmol) and 1-(3-bromo-propyl)-4-methoxy-benzene (614 mg, 2.6 mmol) in acetonitrile (20 mL) $K_2CO_3$ (154 mg, 1.1 mmol) is added and the mixture heated at reflux with stirring for 72 hours. After removal of insolubles by filtration and evaporation of the solvent at reduced pressure the resulting material is dissolved in dry dichloromethane (6 mL) and trifluoroacetic acid (1 mL, 13 mmol) is added. After stirring of the resulting solution at room temperature for 4 hours volatiles are evaporated under reduced pressure and the resulting solid is co-evaporated several times with toluene. The material thus obtained is used as such in the next step. Yield: 0.58 g.

ESI mass spectrum: $[M+H]^+=335$
Retention time HPLC: 0.68 min (Method A)

Example 12

3-[(3,5-Diamino-6-chloro-pyrazine-2-carbonyl)-amino]-1-ethoxycarbonylmethyl-1-[3-(4-methoxy-phenyl)-propyl]-piperidinium chloride

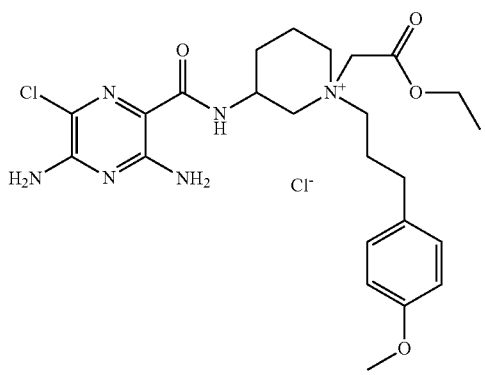 [SMILES: CCOC(=O)C[N+]1(CCCc2ccc(OC)cc2)CCCC(NC(=O)c2nc(Cl)c(N)nc2N)C1 ; [Cl-]]

A solution of 3,5-diamino-6-chloropyrazine-2-carboxylic-acid (Intermediate 1.1.1, 46 mg, 0.25 mmol), 3-amino-1-ethoxycarbonylmethyl-1-[3-(4-methoxy-phenyl)-propyl]-piperidinium bromide trifluoroacetate salt (Intermediate 3.1.2, 230 mg, 0.25 mmol), O-(benzotriazol-1-yl)-N,N,N',N'-tetramethyluronium tetrafluoroborate (86 mg, 0.27 mmol) and N,N-diisopropylethylamine (0.15 mL, 0.1 mmol) in dry N,N-dimethylformamide (5 mL) is stirred for 5 hours at room temperature. The solution is concentrated under reduced pressure to half of the volume, water (2 mL) added and the mixture purified via preparative reverse phase HPLC (gradient of acetonitrile in water+0.05% trifluoroacetic acid). Fractions containing the title compound are concentrated under reduced pressure. The residue is treated with HCl in diethyl ether (2 M, 2 mL), the solvent removed and the residue dried at 50° C. under vacuum. Yield: 56 mg. IC50=0.15.

ESI mass spectrum: $[M]^+=505$
Retention time HPLC: 9.38 min (Method C).

Example 12.1

1-Cyclohexyloxycarbonylmethyl-3-[(3,5-diamino-6-chloro-pyrazine-2-carbonyl)-amino]-1-[3-(4-methoxy-phenyl)-propyl]-piperidinium chloride Intermediate 12.2.1

(3-tert-Butoxycarbonylamino-piperidin-1-yl)-acetic acid cyclohexyl ester

Prepared according to the method described for Intermediate 12.1.1 using cyclohexyl-2-chloroacetate (738 mg, 4.2 mmol) instead of ethyl iodoacetate. Yield: 820 mg.
ESI mass spectrum: $[M]^+=341$
Retention time HPLC: 0.92 min (Method A).

Intermediate 12.2.2

3-Amino-1-cyclohexyloxycarbonylmethyl-1-[3-(4-methoxy-phenyl)-propyl]-piperidinium bromide trifluoroacetate salt Prepared according to the method described for Intermediate 12.1.2 using Intermediate 12.2.1 (820 mg, 1.8 mmol) Yield: 190 mg.
ESI mass spectrum: $[M]^+=389$
Retention time HPLC: 0.85 min (Method A).

Example 12.1

1-Cyclohexyloxycarbonylmethyl-3-[(3,5-diamino-6-chloro-pyrazine-2-carbonyl)-amino]-1-[3-(4-methoxy-phenyl)-propyl]-piperidinium chloride

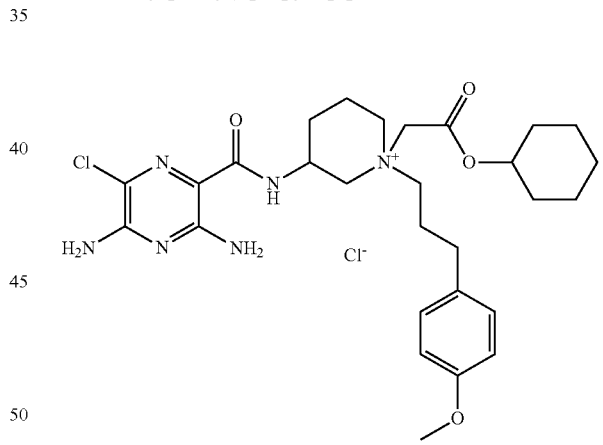

Prepared according to the method described in Example 12 using Intermediate 12.2.2 (180 mg, 0.23 mmol) Yield: 72 mg. IC50=0.21 µM.
ESI mass spectrum: $[M]^+=559$
Retention time HPLC: 10.78 min (Method C).

Intermediate 12.3.1

(S)-3-Amino-1,1-bis-(4-benzyloxy-benzyl)-piperidinium chloride (S)-Piperidin-3-yl-carbamic acid tert-butyl ester (150 mg), 4-benzyloxybenzyl chloride (383 mg), $K_2CO_3$ (227 mg) and NaI (34 mg) are stirred in dimethylsulfoxide (5 mL) for 16 h. Volatiles are evaporated in vacuo, the residue partitioned between water and ethyl acetate, the organic phase collected, dried ($Na_2SO_4$) and volatiles evaporated in vacuo to give 540 mg of crude product that is used without further purification. To the material thus obtained dichloromethane (15 mL) and trifluoroacetic acid (0.56 mL) are added. After 16 h at room temperature volatiles are evaporated in vacuo, methanolic $NH_3$ is added until a slightly basic pH is reached, volatiles are again evaporated and the residue is purified by chromatography (silica gel, dichloromethane:MeOH containing $NH_3OH$ gradient of increasing polarity) to give the title compound. Yield 110 mg.

ESI mass spectrum: $[M]^+=493$

Retention time HPLC: 1.53 min (Method E).

Example 12.2

(S)-1,1-Bis-(4-benzyloxy-benzyl)-3-[(3,5-diamino-6-chloro-pyrazine-2-carbonyl)-amino]-piperidinium chloride

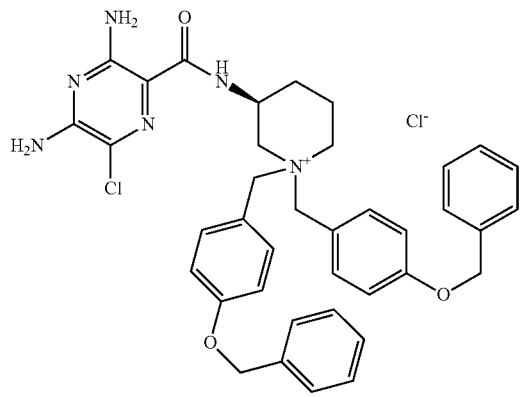 [SMILES: Nc1nc(N)c(C(=O)N[C@H]2CCC[N+](Cc3ccc(OCc4ccccc4)cc3)(Cc3ccc(OCc4ccccc4)cc3)C2)nc1Cl ; [Cl-]]

Prepared according to the method described in Example 12 using Intermediate 12.3.1 (111 mg) Yield: 40 mg.

ESI mass spectrum: $[M]^+=663$

Retention time HPLC: 9.47 min (Method D).

Example 12.3

(S)-3-[(3,5-Diamino-6-chloro-pyrazine-2-carbonyl)-amino]-1,1-bis-[3-(4-methanesulfonyl-phenyl)propyl]-piperidinium chloride Intermediate 12.4.1

1-(3-Bromo-propyl)-4-methanesulfonyl-benzene

The title compound is prepared from 3-[4-(methylthio)phenyl]proprionic acid (1.5 g, Aldrich) by a sequence of standard transformations consisting of esterification with MeOH, reduction to the corresponding alcohol with $LiAlH_4$, conversion to the bromide using N-bromosuccinimide and $PPh_3$, and oxidation to the title sulfone using 3-chloroperbenzoic acid. Yield 1.7 g.

ESI mass spectrum: $[M+NH_4]^+=294/296$

Retention time HPLC: 1.09 min (Method A).

Intermediate 12.4.2

(S)-3-Amino-1,1-bis-[3-(4-methanesulfonyl-phenyl)-propyl]-piperidinium chloride hydrochloride Prepared according to the method described in Example 12.3.1 but using a total of 4.4 eq. of Intermediate 12.4.1 as alkylant, heating at reflux in acetonitrile for ca. 60 h and purifying the intermediate carbamic acid tert-butyl ester (Boc) protected product by column chromatography (silica gel, MeOH/NH4OH gradient of increasing polarity in $CH_2Cl_2$). The carbamic acid tert-butyl ester group is removed using HCl in dioxane to give the title compound. Yield 185 mg, content ca. 61%.

ESI mass spectrum: $[M]^+=493$

Retention time HPLC: 0.65 min (Method A).

Example 12.3

(S)-3-[(3,5-Diamino-6-chloro-pyrazine-2-carbonyl)-amino]-1,1-bis-[3-(4-methanesulfonyl-phenyl)propyl]-piperidinium chloride

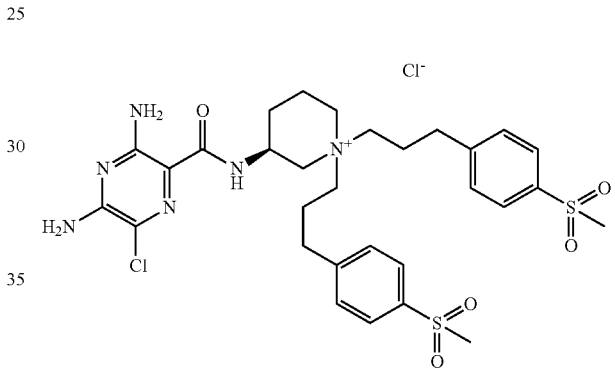

Prepared according to the method described in Example 12 using Intermediate 12.4.2 (185 mg of ca. 61% content) Yield: 72 mg.

ESI mass spectrum: $[M]^+=663$

Retention time HPLC: 6.91 min (Method D).

Example 12.4

(S)-3-[(3,5-Diamino-6-chloro-pyrazine-2-carbonyl)-amino]-1,1-bis-[3-(6-methoxy-pyridin-3-yl)-propyl]-piperidinium chloride Intermediate 12.5.1

5-(3-Bromo-propyl)-2-methoxy-pyridine

The title compound is prepared from 6-methoxy-3-pyridinecarboxaldehyde (0.5 g, Aldrich) by a sequence of standard transformations consisting of Wittig reaction with (carbethoxymethylene)triphenylphosphorane and NaOH, catalytic hydrogenation of the exocyclic C—C double bond, reduction to the corresponding alcohol with $LiAlH_4$, and conversion to the bromide using N-bromosuccinimide and $PPh_3$.

ESI mass spectrum: $[M+H]^+=230/232$

Retention time HPLC: 0.99 min (Method A).

Intermediate 12.5.2

(S)-3-Amino-1,1-bis-[3-(6-methoxy-pyridin-3-yl)-propyl]-piperidinium chloride trihydrochloride Prepared in analogy to the method described in Example 12.4.2, using Intermediate 12.5.1. Yield 345 mg, content ca. 72%.

ESI mass spectrum: $[M]^+=399$
Retention time HPLC: 0.60 min (Method A).

Intermediate 12.5.1

5-(3-Bromo-propyl)-2-methoxy-pyridine

The title compound is prepared from 6-methoxy-3-pyridinecarboxaldehyde (0.5 g, Aldrich) by a sequence of standard transformations consisting of Wittig reaction with (carbethoxymethylene)triphenylphosphorane and NaOH, catalytic hydrogenation of the exocyclic C—C double bond, reduction to the corresponding alcohol with LiAlH$_4$, and conversion to the bromide using N-bromosuccinimide and PPh$_3$.

ESI mass spectrum: $[M+H]^+=230/232$
Retention time HPLC: 0.99 min (Method A).

Intermediate 12.5.2

(S)-3-Amino-1,1-bis-[3-(6-methoxy-pyridin-3-yl)-propyl]-piperidinium chloride trihydrochloride Prepared in analogy to the method described in Example 12.4.2, using Intermediate 12.5.1. Yield 345 mg, content ca. 72%.

ESI mass spectrum: $[M]^+=399$
Retention time HPLC: 0.60 min (Method A).

Example 12.4

(S)-3-[(3,5-Diamino-6-chloro-pyrazine-2-carbonyl)-amino]-1,1-bis-[3-(6-methoxy-pyridin-3-yl)-propyl]-piperidinium chloride

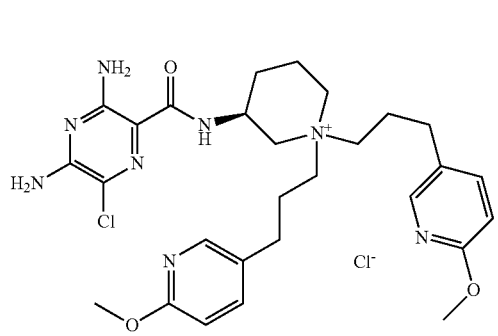 [SMILES: COc1ccc(CCC[N+]2(CCCc3ccc(OC)nc3)CCC[C@H](NC(=O)c3nc(Cl)c(N)nc3N)C2)cn1 ; [Cl-]]

Prepared according to the method described in Example 12 using Intermediate 12.5.2 (250 mg of ca. 72% content). Yield: 15 mg.

ESI mass spectrum: $[M]^+=569$
Retention time HPLC: 6.73 min (Method D).

Example 12.5

(S)-3-[(3,5-Diamino-6-chloro-pyrazine-2-carbonyl)-amino]-1-{3-(4-methoxy-phenyl)-1-2-(4-methoxy-phenyl)-ethyl]-propyl}-1-methyl-piperidinium chloride (mixture of stereoisomers)

Intermediate 12.6.1

(S)-3-Amino-1-{3-(4-methoxy-phenyl)-1-[2-(4-methoxy-phenyl)-ethyl]-propyl}-1-methyl-piperidinium chloride hydrochloride (mixture of stereoisomers)

To (S)-piperidin-3-yl-carbamic acid tert-butyl ester (0.10 g) and 1,5-bis-(4-methoxy-phenyl)-pentan-3-one (254 mg, content ca. 88%; obtained by catalytic hydrogenation on platinum oxide pre-catalyst of bis(4-methoxybenzylidene) acetone, Pfaltz-Bauer) in CH$_2$Cl$_2$ is added Ti(OiPr)$_4$ (0.22 mL). The mixture is stirred for 20 h, then NaBH$_4$ (94 mg) is added in several portions. After 20 h MeOH is added and after 30 min volatiles are evaporated, the residue treated with EtOAc and filtered. The filtrate is concentrated in vacuo and purified by column chromatography (SiOH, cHex: EtOAc gradient of increasing polarity). Material thus obtained is allowed to react with iodomethane (2 eq.) in the presence of K$_2$CO$_3$ (1 eq.) in dimethylsulfoxide at 120° C. for 30 min under microwave irradiation. Volatiles are evaporated in vacuo, the residue is purified via preparative reverse phase HPLC. The carbamic acid tert-butyl ester group is removed using HCl in dioxane to give the title compound of content ca. 68%.

ESI mass spectrum: $[M]^+=397$
Retention time HPLC: 0.87 min (Method B).

Example 12.5

(S)-3-[(3,5-Diamino-6-chloro-pyrazine-2-carbonyl)-amino]-1-{3-(4-methoxy-phenyl)-1-2-(4-methoxy-phenyl)-ethyl]-propyl}-1-methyl-piperidinium chloride (mixture of stereoisomers)

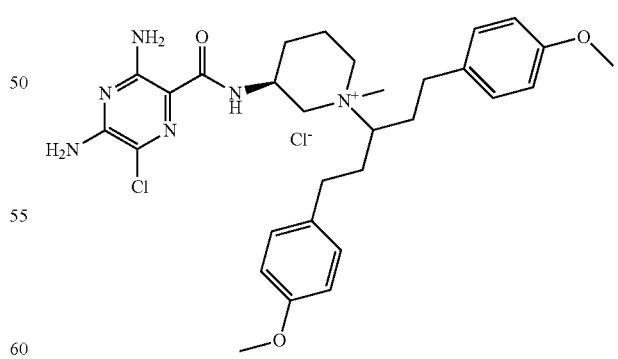

Prepared as a mixture of stereoisomers according to the method described in Example 12 using Intermediate 12.6.1 (106 mg of ca. 68% content). Yield: 16 mg.

ESI mass spectrum: $[M]^+=567$
Retention time HPLC: 7.96-8.14 min (Method D).

Example 13

1-Carboxymethyl-3-[(3,5-diamino-6-chloro-pyrazine-2-carbonyl)-amino]-1-[3-(4-methoxy-phenyl)propyl]-piperidinium chloride

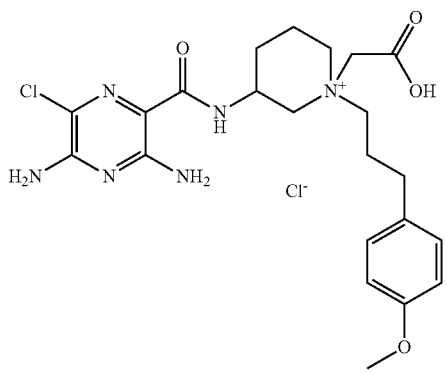 [SMILES: COc1ccc(CCC[N+]2(CC(=O)O)CCCC(NC(=O)c3nc(Cl)c(N)nc3N)C2)cc1 ; [Cl-]]

A solution of 3-[(3,5-diamino-6-chloro-pyrazine-2-carbonyl)-amino]-1-ethoxycarbonylmethyl-1-[3-(4-methoxyphenyl)-propyl]-piperidinium chloride (Example 3.1, 30 mg, 0.06 mmol) in hydrochloric acid (6 M, 1 mL) is heated at 60° C. for 36 hours. Volatiles are removed by freeze-drying. The resulting amorphous solid is triturated with diethyl ether and dried under vacuum at 50° C. Yield: 21 mg. IC50>1 µM ESI mass spectrum: $[M]^+$=477
Retention time HPLC: 6.28 min (Method C).

Example 14

3-[(3,5-Diamino-6-chloro-pyrazine-2-carbonyl)-amino]-1-methoxycarbonylmethyl-1-[3-(4-methoxyphenyl)-propyl]-piperidinium chloride

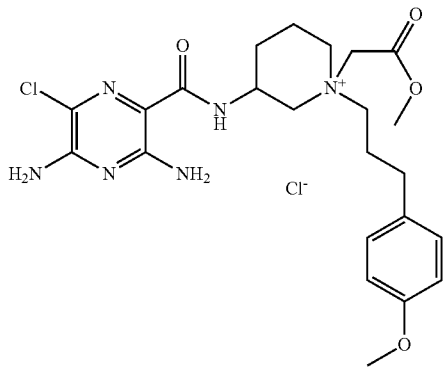 [SMILES: COC(=O)C[N+]1(CCCc2ccc(OC)cc2)CCCC(NC(=O)c2nc(Cl)c(N)nc2N)C1 ; [Cl-]]

To a solution of 1-carboxymethyl-3-[(3,5-diamino-6-chloro-pyrazine-2-carbonyl)-amino]-1-[3-(4-methoxy-phenyl)-propyl]-piperidinium chloride (Example 4.1, 20 mg, 0.04 mmol) in methanol (3 mL) 12 M hydrochloric acid (0.1 mL) is added and the reaction mixture stirred at 80° C. for 48 hours. The solvent is removed under reduced pressure and the resulting solid dried under vacuum at 50° C. Yield: 18 mg. IC 50=0.137 µM ESI mass spectrum: $[M]^+$=491
Retention time HPLC: 8.93 min (Method C).

Analytical Methods and Preparative Chromatography
Method A:
Instrument: LC/MS Waters Acquity UPLC System DAD, SQD single quadrupole
Column: HSS C18 1.8 µm 2.1×50 mm, T=35° C.
Mobile phase:
A=$H_2O$ 90%+10% $CH_3CN$+$CF_3COOH$ 0.1%
B=$CH_3CN$ 90%+$H_2O$ 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−
Scan range: 90-900 amu
Method B:
Instrument: LC/MS Waters Acquity UPLC System DAD, SQD single quadrupole
Column: BEH C18 1.7 µm 2.1×50 mm, T=35° C.
Mobile phase:
A=$H_2O$ 90%+10% $CH_3CN$+$NH_4COOH$ 5 mM
B=$CH_3CN$ 90%+$H_2O$ 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−
Scan range: 90-900 amu
Method C:
Instrument: LC/MS ThermoFinnigan HPLC Surveyor DAD, MSQ single quadrupole
Column: Synergi Hydro RP80A, 4 µm, 4.6×100 mm
Mobile phase:
A=$H_2O$ 90%+10% $CH_3CN$+$NH_4COOH$ 10 mM
B=$CH_3CN$ 90%+$H_2O$ 10%+$NH_4COOH$ 10 mM

| Time in min | % A | % B | flow rate in mL/min |
|---|---|---|---|
| | 100 | 0 | 1.2 |
| | 100 | 0 | 1.2 |
| | 0 | 100 | 1.2 |
| | 0 | 100 | 1.2 |
| | 100 | 0 | 1.2 |
| | 100 | 0 | 1.2 |

Detection: UV 254 nm, Finnigan MSQ, single quadrupole
Ion source: APCI+/APCI−
Scan range: 100-900 amu
Method D:
Instrument: LC/MS ThermoFinnigan HPLC Surveyor DAD, LCQFleet Ion Trap
Column: Simmetry Shield RPB, 5 µm, 4.6×150 mm Mobile phase:
A=H$_2$O 90%+10% CH$_3$CN+HCOOH 0.1%
B=CH$_3$CN 90%+H$_2$O 10%+HCOOH 0.1%

| Time in min: | % A | % B | flow rate in mL/min |
|---|---|---|---|
| 0.00 | 95 | 5 | 1 |
| 1.50 | 95 | 5 | 1 |
| 11.5 | 5 | 95 | 1 |
| 13 | 5 | 95 | 1 |
| 13.3 | 95 | 5 | 1 |
| 15 | 95 | 5 | 1 |

Detection: UV 254 nm; Finnigan Fleet, Ion Trap
Ion source: ES+
Scan range: 100-900 amu Method E:
Instrument: LC/MS Waters Alliance 2695 HPLC System DAD, Quattro Micro Triple quadrupole
Column: Gemini C18 3 μm 4.6×50 mm, T=35° C.
Mobile phase:
A=H$_2$O 90%+10% CH$_3$CN+CF$_3$COOH 0.1%
B=CH$_3$CN 90%+H$_2$O 10%

| Time in min | % A | % B | flow rate in mL/min |
|---|---|---|---|
| 0.00 | 70 | 30 | 1.3 |
| 3.5 | 10 | 90 | 1.3 |
| 4.5 | 10 | 90 | 1.3 |
| 4.6 | 70 | 30 | 1.3 |

Detection: UV 254 nm
Detection: Quattro Micro, triple quadrupole
Ion source: ES+
Scan range: 120-900 amu Method F:
Column: Waters Sunfire C18, 4.6×50 mm, 3.5 μm
Mobile phase:
A: water+0.1% TFA
B: methanol

| Time in min | % A | % B | flow rate in mL/min |
|---|---|---|---|
| 0.00 | 80 | 20 | 2 |
| 1.70 | 0 | 100 | 2 |
| 2.50 | 0 | 100 | 2 |
| 2.60 | 80 | 20 | 2 |
|  | 80 | 20 | 2 |

Wavelength: 210-500 nm
Temperature: 60° C.

Method G:
Column: Waters Sunfire C18, 4.6×50 mm, 3.5 μm
Mobile phase:
A: water+0.1% TFA
B: methanol

| Time in min | % A | % B | flow rate in mL/min |
|---|---|---|---|
| 0.00 | 95 | 5 | 2.0 |
| 2.00 | 0 | 100 | 2.0 |
| 2.50 | 0 | 100 | 2.0 |
| 2.60 | 95 | 5 | 2.0 | wavelength: 210-500 nm
temperature: 60° C.

Method H:
Column: Waters Sunfire C18, 4.6×50 mm, 3.5 μm
Mobile phase:
A: water+0.1% TFA
B: methanol

| Time in min | % A | % B | flow rate in mL/min |
|---|---|---|---|
| 0.00 | 80 | 20 | 2 |
| 1.70 | 0 | 100 | 2 |
| 2.50 | 0 | 100 | 2 |
| 2.60 | 80 | 20 | 2 |
|  | 80 | 20 | 2 |

Wavelength: 210-500 nm
Temperature: 60° C.

Method I:
Column: Waters Sunfire C18, 4.6×30 mm, 2.5 μm
Mobile phase:
A: water+0.1% TFA
B: methanol+0.1% TFA

| Time in min | % A | % B | flow rate in mL/min |
|---|---|---|---|
| 0.00 | 95 | 5 | 4 mL/min |
| 0.05 | 95 | 5 | 3 mL/min |
| 2.05 | 0 | 100 | 3 mL/min |
| 2.10 | 0 | 100 | 4 mL/min |
| 2.35 | 0 | 100 | 4 mL/min |

Wavelength: 210-500 nm
Temperature: 60° C.

Method K:
Column: Waters Sunfire C18, 4.6×30 mm, 2.5 μm
Mobile phase:
A: water+0.1% TFA
B: methanol+0.1% TFA

| Time in min | % A | % B | flow rate in mL/min |
|---|---|---|---|
| 0.00 | 95 | 5 | 2.2-2.9 mL/min |
| 0.30 | 95 | 5 | 2.2-2.9 mL/min |
| 1.50 | 0 | 100 | 2.2-2.9 mL/min |
| 1.55 | 0 | 100 | 2.2-2.9 mL/min |
| 1.65 | 0 | 100 | 2.2-2.9 mL/min |

Wavelength 210-500 nm
Temperature 60° C.

Method L:
Column: Waters Sunfire C18, 4.6×30 mm, 2.5 μm
Mobile phase:
A: water+0.1% TFA
B: methanol+0.1% TFA

| Time in min | % A | % B | flow rate in mL/min |
|---|---|---|---|
| 0.00 | 95 | 5 | 1.8-2.5 mL/min |
| 0.25 | 95 | 5 | 1.8-2.5 mL/min |
| 1.70 | 0 | 100 | 1.8-2.5 mL/min |
| 1.75 | 0 | 100 | 1.8-2.5 mL/min |
| 1.90 | 0 | 100 | 1.8-2.5 mL/min |

Wavelength 210-500 nm
Temperature 60° C.

Method M:
Column: Waters Sunfire C18, 4.6×50 mm, 3.5 μm

Mobile phase:
A: water+0.1% TFA
B: methanol

| Time in min | % A | % B | flow rate in mL/min |
|---|---|---|---|
| 0.00 | 95 | 5 | 1.5 |
| 1.30 | 0 | 100 | 1.5 |
| 3.00 | 0 | 100 | 1.5 |
| 3.40 | 95 | 5 | 1.5 |

Wavelength: 210-500 nm
Temperature: 40° C.
Method N:
Column: Waters Sunfire C18, 4.6×30 mm, 2.5 μm
Mobile phase:
A: water+0.1% TFA
B: methanol+0.1% TFA

| Time in min | % A | % B | flow rate in mL/min |
|---|---|---|---|
| 0.00 | 95 | 5 | 4 |
| 0.05 | 95 | 5 | 3 |
| 2.05 | 0 | 100 | 3 |
| 2.10 | 0 | 100 | 4.5 |
| 2.35 | 0 | 100 | 4.5 |

Wavelength: 210-500 nm
Temperature: 60° C.
The following abbreviations are used above and hereinafter:
ACN Acetonitrile
BOC tert-Butoxycarbonyl
DCM Dichloromethane
DIPEA Diisopropyl-ethylamine
DMAP 4-Dimethylaminopyridine
DMF N,N-Dimethylformamide
DPPF 1,1'-Bis(diphenylphosphino)ferrocene
EDC 1-Ethyl-3-(3-dimethylaminopropyl)carbodiimide hydrochloride
Eq. Molar equivalent
ESI Electrospray ionization
h hour
HATU O-(7-Azabenzotriazol-1-yl)-N,N,N',N'-tetramethyluronium hexafluorophosphate
HCl Hydrochloric acid
KOH Potassium hydroxide
l liter
LiHMDS Lithium bis(trimethylsilyl)amide
M mol/l
Min minutes
Mp melting point
NaOH Sodium hydroxide
n.d. not determined
Pd/C palladium on charcoal
r.t. ambient temperature (about 20° C.)
RT retention time
TBME Methyl tert-butyl ether
TBTU 2-(1H-Benzotriazol-1-yl)-1,1,3,3-tetramethyluronium-tetrafluoroborate
TEA Triethylamine
TFA Trifluoroacetic acid
THF Tetrahydrofurane
TLC Thin Layer Chromatography
TMS Trimethylsilyl Pharmacological Test Method The $IC_{50}$ values of the example compounds given above were determined in the Ussing Chamber assay.

Ussing Chamber: Mouse kidney M-1 cells were cultivated in DMEM containing 5% FCS and 5 μM dexamethasone for 10 to 12 days on polyester transwell filters. Filters were inserted into a teflon-coated well-plate which fit into the ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode with the software package Lab View for data acquisition and analysis. The transepithelial electrical resistance (TEER) was determined by the application of voltage steps of ±5 mV every 5 sec. Compounds were administered at a final concentration of 3 μM or at increasing concentrations (1-3-10 μM) to the apical solution. At the end of each experiment the amiloride sensitive I_SC was measured by adding 3 μM amiloride to the apical compartment. Results are expressed as inhibition in percent of the amiloride effect or as $IC_{50}$.

Permeability in CALU-3 Cells:

Permeability measurements across polarized, confluent CALU-3 cell monolayers grown on permeable filter supports are used to provide information on the potential of a compound to pass the lung epithelium. Apparent permeability coefficients (Papp) of the compounds across the CALU-3 cell monolayers are measured (pH 7.4, 37° C.) in apical-to-basal (AB) and basal-to-apical (BA) transport direction. AB permeability (Papp, AB) represents drug absorption from the lung lumen into the blood and BA permeability (Papp, BA) drug transport from the blood into the lung lumen mainly via passive permeability since Calu-3 cells as well as lung epithelial cells do not express efflux transporters like P-gp, while uptake transporters may be expressed.

CALU-3 cells ($1-2 \times 10^5$ cells/1 $cm^2$ area) are seeded on filter inserts (Costar transwell polycarbonate filters, 0.4 μm pore size) and cultured (for 10-12 days DMEM) until tight monolayers are formed. Compounds of interest are dissolved in appropriate solvent (DMSO, 10 mM stock solution). Stock solutions are diluted with HTP-4 buffer (128.13 mM NaCl, 5.36 mM KCl, 1 mM MgSO4, 1.8 mM CaCl2, 4.17 mM NaHCO3, 1.19 mM Na2HPO4×7H$_2$O, 0.41 mM NaH2PO4× H2O, 15 mM HEPES, 20 mM glucose, 0.25% BSA, pH 7.4) to prepare the transport solution (10 μM compound, final DMSO <=0.5%). The transport solution (TL) is applied to the apical or basolateral donor side for measuring A-B or B-A permeability (3 filter replicates), respectively. The receiver side contains the same buffer as the donor side. After 30 mM of accommodation, samples are collected at the start t0=0 min and at the end of the experiment to =90 min from the donor and at 0, 30, 60, and 90 min also from the receiver chamber. Volume removed is replenwashed by HTP-4 buffer. The compound concentration in the samples is measured by HPLC-MS/MS or scintillation counting. The permeability coefficient (Papp) and efflux ratio are calculated according to: Papp [cm/s]=(concentration receiver [nM]*volume receiver [mL]/time interval [sec])*(1/filter area)*(1/donor concentration [nM]).

Indications

As has been found, the compounds of formula (1) are characterised by their wide range of applications in the therapeutic field. Particular mention should be made of those applications for which the compounds according to the invention of formula (1) are preferably suited on account of their pharmaceutical efficacy as ENaC inhibitors. Examples include respiratory diseases or complaints, or allergic diseases of the airways.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (1) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (1) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Combinations

The compounds of formula (1) may be used on their own or in conjunction with other active substances of formula (1) according to the invention. If desired the compounds of formula (1) may also be used in combination with other pharmacologically active substances.

Therefore the invention further relates to medicament combinations which preferably contain, besides one or more compounds of formula (1) or a salt thereof, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Formulations

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula (1) according to the preferred embodiments above.

It is also preferred if the compounds of formula (1) are administered by inhalation, particularly preferably if they are administered once or twice a day. For this purpose, the compounds of formula (1) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include conic.) centrates or sterile ready-to-use inhalable solutions. The preparations which may be used according to the invention are described in more detail in the next part of the specification.

Inhalable Powders

If the active substances of formula (1) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (1) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (1) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finwashed pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

What we claim:
1. A compound of formula 1,

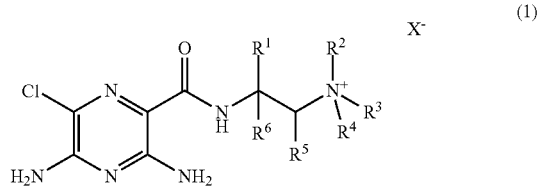

(1)

wherein
$R^6$ is selected from H or $C_{1-4}$-alkyl;
$R^2$ is selected from $C_{1-4}$-alkyl;

$R^3$ is selected from $C_{1-4}$-alkyl, optionally substituted with one or two groups selected from $C_{5-6}$-cycloalkyl, indolyl, HO(O)C—, $C_{1-4}$-alkyl-O(O)C—, $C_{5-6}$-cycloalkyl-O(O)C—, aryl-O— optionally substituted with $C_{1-4}$-alkyl-O—, aryl-$C_{1-4}$-alkyl optionally substituted with $C_{1-4}$-alkyl-O—, or aryl optionally substituted with one or two $R^{3.1}$—, $R^{3.1}$—O—, $R^{3.1}$—$CH_2$—, $R^{3.1}$—$CH_2$—O—, halogen or NC—, wherein
$R^{3.1}$ is selected independently from H, $C_{1-4}$-alkyl, benzyl, HO(O)C—,
$C_{1-4}$-alkyl-O(O)C—, HO—$CH_2$—, $C_{1-4}$-alkyl-O—$CH_2$—, ($C_{1-4}$-alkyl)$_2$N—$CH_2$—,
$C_{1-4}$-alkyl-(O)$_2$S, H[O—$CH_2$—$CH_2$]$_n$—, $R^{3.1.1}$HN(O)C—, ($R^{3.1.1}$)$_2$N(O)C—, $R^{3.1.2}$HN(O)C— or ($R^{3.1.2}$)$_2$N(O)C—, wherein
n is 3, 4 or 5,
$R^{3.1.1}$ is selected independently from H, H—[O—$CH_2$—$CH_2$]$_2$—, H—[O—$CH_2$—$CH_2$]$_3$— or a five-, six- or nine-membered heterocyclyl, wherein one, two or three elements are replaced by an element independently selected from N, O or S; each five-, six- or nine-membered heterocyclyl optionally substituted with one or two substituents independently selected from $C_{1-4}$-alkyl-, HO—, HO—$C_{1-4}$-alkyl- or O═ or two substituents $R^{3.1.1}$ together with the nitrogen atom they are bound to form a five-, six- or nine-membered heterocyclyl, wherein one or two further elements are replaced by an element independently selected from N, O or S; each five-, six- or nine-membered heterocyclyl is optionally substituted with one or two substituents independently selected from $C_{1-4}$-alkyl, $C_{1-4}$-alkyl-O— or O═, and $R^{3.1.2}$ is independently branched or unbranched $C_{1-4}$-alkyl, optionally substituted with one or two substituents selected independently from O═, NC—, HO—, $C_{1-4}$-alkyl-O—, ($C_{1-4}$-alkyl)$_2$N—, Cl($C_{1-4}$-alkyl)$_3$N—, HO(O)C—, $C_{1-4}$-alkyl-O(O)C—, HO(O)$_2$S—, $C_{1-4}$-alkyl-(O)$_2$S—, $C_{1-4}$-alkyl-(O)$_2$S—, ($C_{1-4}$-alkyl)$_2$OP— or a five- or six-membered heterocyclyl or heteroaryl, wherein one or two elements are replaced by an element independently selected from N or O; each five- or six-membered heterocyclyl or heteroaryl being optionally substituted with one or two substituents independently selected from $C_{1-4}$-alkyl or O═;
$R^4$ is selected from $C_{1-4}$-alkyl, optionally substituted with one or two groups selected from $C_{5-6}$-cycloalkyl, indolyl, HO(O)C—, $C_{1-4}$-alkyl-O(O)C—,
$C_{5-6}$-cycloalkyl-O(O)C—, aryl-O— optionally substituted with $C_{1-4}$-alkyl-O—, aryl-$C_{1-4}$-alkyl optionally substituted with $C_{1-4}$-alkyl-O—, or aryl optionally substituted with one or two $R^{4.1}$—, $R^{4.1}$—O—, $R^{4.1}$—$CH_2$—,
$R^{4.1}$—$CH_2$—O—, halogen or NC—, wherein $R^{4.1}$ is selected independently from H, $C_{1-4}$-alkyl, benzyl, HO(O)C—, $C_{1-4}$-alkyl-O(O)C—, HO—$CH_2$—, $C_{1-4}$-alkyl-O—$CH_2$—, ($C_{1-4}$-alkyl)$_2$N—$CH_2$—, $C_{1-4}$-alkyl-(O)$_2$S, H—[O—$CH_2$—$CH_2$]$_n$—, $R^{4.1.1}$HN(O)C—, ($R^{4.1.1}$)$_2$N(O)C—, $R^{4.1.2}$HN(O)C— or ($R^{4.1.2}$)$_2$N(O)C—, wherein
n is 3, 4 or 5,
$R^{4.1.1}$ is selected independently from H, H—[O—$CH_2$—$CH_2$]$_2$—, H—[O—$CH_2$—$CH_2$]$_3$— or a five-, six- or nine-membered heterocyclyl, wherein one, two or three elements are replaced by an element independently selected from N, O or S; each five-, six- or nine-membered heterocyclyl being optionally substituted with one or two substituents independently selected from $C_{1-4}$-alkyl-, HO—, HO—$C_{1-4}$-alkyl-, O═ or two substituents $R^{4.1.1}$ together with the nitrogen atom they are bound to form a five-, six- or nine-membered heterocyclyl, wherein one or two further elements are replaced by an element independently selected from N, O or S; each five-, six- or nine-membered heterocyclyl being optionally substituted with one or two substituents independently selected from $C_{1-4}$-alkyl-, HO—, HO—$C_{1-4}$-alkyl-, O═, and $R^{4.1.2}$ is branched or unbranched $C_{1-4}$-alkyl, optionally substituted with one or two substituents selected independently from O═, NC—, HO—, $C_{1-4}$-alkyl-O—, $(C_{1-4}$-alkyl$)_2$N—, Cl($C_{1-4}$-alkyl$)_3$N—, HO(O)C—, $C_{1-4}$-alkyl-O(O)C—, HO(O)$_2$S—, $C_{1-4}$-alkyl-(O)$_2$S—, $C_{1-4}$-alkyl-(O)$_2$S—, ($C_{1-4}$-alkyl$)_2$OP— or a five- or six-membered heterocyclyl or heteroaryl, wherein one or two elements are replaced by an element independently selected from N or O; each five- or six-membered heterocyclyl or heteroaryl being optionally substituted with one or two substituents independently selected from $C_{1-4}$-alkyl or O═;

$R^5$ is H;

or $R^1$ and $R^2$ are together $R^{12}$, wherein $R^{12}$ is selected from $C_{2-4}$-alkylene each optionally partially or fully substituted with $R^{12.1}$, wherein $R^{12.1}$ is selected from phenyl, optionally substituted with $C_{1-4}$-alkyl;

or $R^1$, $R^2$ and $R^4$ together with the atoms connecting them form an aza-bicyclo [2.2.2] octane;

or $R^1$ and $R^5$ are together —CH$_2$—; and $X^-$ is selected from chloride, bromide, iodide, hydroxide, hydrogensulfate, nitrate, formiate, acetate, trifluoroacetate, methanesulfonate or p-toluenesulfonate;

or a pharmaceutically acceptable salt thereof.

2. The compound according to claim 1 wherein $R^1$ and $R^2$ are together $R^{12}$ and $R^{12}$ is selected from $C_{2-4}$-alkylene each optionally partially or fully substituted with $R^{12.1}$ wherein $R^{12.1}$ is selected from phenyl, optionally substituted with $C_{1-4}$-alkyl.

3. The compound according to claim 2 wherein $R^1$ and $R^2$ are together $R^{12}$, wherein $R^{12}$ is selected from —CH$_2$—CH$_2$—, —CH$_2$—CH$_2$—CH$_2$—, —CH$_2$—CH$_2$—CH$_2$—CH$_2$— each optionally partially or fully substituted with $R^{12.1}$, wherein $R^{12.1}$ is selected from phenyl, optionally substituted with CH$_3$—.

4. The compound according to claim 1 wherein $R^1$, $R^2$ and $R^4$ together with the atoms connecting them form an aza-bicyclo[2.2.2]octane, wherein said compound is selected from compounds of formula (2)

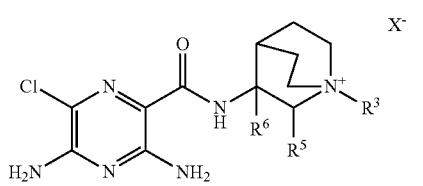

(2)

wherein $R^3$, $R^5$, $R^6$ and $X^-$ are as defined in claim 1.

5. The compound according to claim 1 wherein $R^1$ and $R^5$ are together —CH$_2$—.

6. The compound according to claim 1 wherein $R^6$ is selected from H or CH$_3$.

7. The compound according to claim 6 wherein $R^6$ is H.

8. The compound according to claim 1 wherein $R^2$ is selected from $C_{1-4}$-alkyl.

9. The compound according to claim 8 wherein $R^2$ is CH$_3$.

10. The compound according to claim 1 wherein $R^3$ is selected from $C_{1-4}$-alkyl optionally substituted with one or two groups selected from $C_{5-6}$-cycloalkyl, indolyl, HO(O)C—, $C_{1-4}$-alkyl-O(O)C—CH$_2$—, $C_{5-6}$-cycloalkyl-O(O)C—CH$_2$—, phenyl-O-optionally substituted with $C_{1-4}$-alkyl-O—, phenyl substituted with two halogen, phenyl optionally substituted with one $R^{3.1}$—, $R^{3.1}$—O—, $R^{3.1}$—CH$_2$—, $R^{3.1}$—CH$_2$—O—, halogen or NC—, wherein $R^{3.1}$ is independently selected from H, $C_{1-4}$-alkyl, benzyl, HO(O)C—, $C_{1-4}$-alkyl-O(O)C—, HO—CH$_2$—, $C_{1-4}$-alkyl-O—CH$_2$—, $(C_{1-4}$-alkyl$)_2$N—CH$_2$—, H—[O—CH$_2$—CH$_2$]$_n$—, $R^{3.1.1}$HN(O)C—, $(R^{3.1.1})_2$N(O)C—, $R^{3.1.2}$HN(O)C— or $(R^{3.1.2})_2$N(O)C—, n is 3, 4 or 5, $R^{3.1.1}$ is independently selected from H, H—[O—CH$_2$—CH$_2$]$_2$— or H—[O—CH$_2$—CH$_2$]$_3$— or a five or six-membered heterocyclyl selected from piperidinyl optionally substituted with $C_{1-4}$-alkyl, pyrrolidinyl optionally substituted with one or two substituents selected independently from $C_{1-4}$-alkyl or O═, tetrahydrofuranyl optionally substituted with $C_{1-4}$-alkyl-O—, or tetrahydrothiophenyl optionally substituted with two O═, or two substituents $R^{3.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine, each five, six- or nine-membered heterocyclyl being optionally substituted with one or two substituents selected independently from $C_{1-4}$-alkyl-, HO—, HO—$C_{1-4}$-alkyl- or O═, and $R^{3.1.2}$ is branched or unbranched $C_{1-4}$-alkyl, optionally substituted with one or two substituents selected independently from O═, NC—, HO—, $C_{1-4}$-alkyl-O—, $(C_{1-4}$-alkyl$)_2$N—, Cl($C_{1-4}$-alkyl$)_3$N—, HO(O)C—, $C_{1-4}$-alkyl-O(O)C—, HO(O)$_2$S—, $C_{1-4}$-alkyl-(O)$_2$S—, $C_{1-4}$-alkyl-(O)$_2$S—, $(C_{1-4}$-alkyl$)_2$OP— or a five or six-membered heterocyclyl or heteroaryl selected from pyrrolidinyl, pyridyl, imidazolyl, piperidinyl, piperazinyl, morpholinyl, each five or six-membered heterocyclyl or heteroaryl being optionally substituted with one or two substituents selected independently from $C_{1-4}$-alkyl or O═.

11. The compound according to claim 10 wherein $R^3$ is selected from $C_{1-4}$-alkyl optionally substituted with one or two groups selected from cyclohexyl, indolyl, HO(O)C—CH$_2$—, CH$_3$O(O)C—CH$_2$—, $C_2$H$_5$—O(O)C—CH$_2$—, cyclohexyl-O(O)C—CH$_2$—, phenyl-O-optionally substituted with CH$_3$O—, phenyl substituted with two F, or phenyl optionally substituted with one $R^{3.1}$—, $R^{3.1}$—O—, $R^{3.1}$—CH$_2$—, $R^{3.1}$—CH$_2$—O—, Cl or NC—, wherein $R^{3.1}$ is selected independently from H, CH$_3$, C$_2$H$_5$, benzyl, HO(O)C—, CH$_3$O(O)C—, HO—CH$_2$—, CH$_3$O—CH$_2$—, (CH$_3$)$_2$N—CH$_2$—, H—[O—CH$_2$—CH$_2$]$_n$—, $R^{3.1.1}$HN(O)C—, $(R^{3.1.1})_2$N(O)C—, $R^{3.1.2}$HN(O)C— or $(R^{3.1.2})_2$N(O)C—, wherein n is 3, 4 or 5, $R^{3.1.1}$ is independently selected from H, H—[O—CH$_2$—CH$_2$]$_2$—, H—[O—CH$_2$—CH$_2$]$_3$— or a five- or six-membered heterocyclyl selected from piperidinyl optionally substituted with CH$_3$, pyrrolidinyl optionally substituted with one or two substituents selected independently from $CH_3$— or O=, tetrahydrofuranyl optionally substituted with $CH_3O$—, or tetrahydrothiophenyl optionally substituted with two O=, or two substituents $R^{3.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five or six-membered heterocyclyl optionally substituted with one or two substituents selected independently from $CH_3$, HO—, $HOCH_2$—, HO—$CH_2$—$CH_2$—, or O=, and $R^{3.1.2}$ is branched or unbranched $C_{1-4}$-alkyl optionally substituted with one or two substituents independently selected from O=, NC—, HO—, $CH_3O$—, $(CH_3)_2N$—, $Cl(CH_3)_3N$—, HO(O)C—, $CH_3O(O)C$—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl is optionally substituted with one or two substituents selected independently from $CH_3$— or O=.

12. The compound according to claim 1 wherein $R^4$ is selected from $C_{1-4}$-alkyl optionally substituted with one or two groups selected from $C_{5-6}$-cycloalkyl, indolyl, HO(O)C—, $C_{1-4}$-alkyl-O(O)C—$CH_2$—, $C_{5-6}$-cycloalkyl-O(O)C—$CH_2$—, phenyl-O-optionally substituted with $C_{1-4}$-alkyl-O—, phenyl substituted with two halogen, or phenyl optionally substituted with one $R^{4.1}$—, $R^{4.1}$—O—, $R^{4.1}$—$CH_2$—, $R^{4.1}$—$CH_2$—O—, halogen or NC—, wherein $R^{4.1}$ is independently selected from H, $C_{1-4}$-alkyl, benzyl, HO(O)C—, $C_{1-4}$-alkyl-O(O)C—, HO—$CH_2$—, $C_{1-4}$-alkyl-O—$CH_2$—, $(C_{1-4}$-alkyl$)_2$N—$CH_2$—, H—[O—$CH_2$—$CH_2]_n$—, $R^{4.1.1}$HN(O)C—, $(R^{4.1.1})_2$N(O)C—, $R^{4.1.2}$HN(O)C—, or $(R^{4.1.2})_2$N(O)C—, n is 3, 4 or 5, $R^{4.1.1}$ is independently selected from H, H—[O—$CH_2$—$CH_2]_2$—, H—[O—$CH_2$—$CH_2]_3$—, or a five or six-membered heterocyclyl selected from piperidinyl optionally substituted with $C_{1-4}$-alkyl, pyrrolidinyl optionally substituted with one or two substituents selected independently from $C_{1-4}$-alkyl or O=, tetrahydrofuranyl optionally substituted with $C_{1-4}$-alkyl-O—, or tetrahydrothiophenyl optionally substituted with two O=, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine, each five-, six- or nine-membered heterocyclyl being optionally substituted with one or two substituents selected independently from $C_{1-4}$-alkyl-, HO—, HO—$C_{1-4}$-alkyl-, O=, and $R^{4.1.2}$ is branched or unbranched $C_{1-4}$-alkyl optionally substituted with one or two substituents selected independently from O=, NC—, HO—, $C_{1-4}$-alkyl-O—, $(C_{1-4}$-alkyl$)_2$N—, $Cl(C_{1-4}$-alkyl$)_3$N—, HO(O)C—, $C_{1-4}$-alkyl-O(O)C—, $HO(O)_2S$—, $C_{1-4}$-alkyl-$(O)_2S$—, $C_{1-4}$-alkyl-$(O)_2S$—, $(C_{1-4}$-alkyl$)_2OP$— or five or six-membered heterocyclyl or heteroaryl selected from pyrrolidinyl, pyridyl, imidazolyl, piperidinyl, piperazinyl, morpholinyl, each five or six-membered heterocyclyl or heteroaryl being optionally substituted with one or two substituents selected independently from $C_{1-4}$-alkyl or O=.

13. The compound according to claim 12 wherein $R^4$ is selected from $C_{1-4}$-alkyl optionally substituted with optionally substituted with one or two groups selected from cyclohexyl, indolyl, HO(O)C—, $CH_3O(O)C$—$CH_2$—, $C_2H_5$—O(O)C—$CH_2$— or cyclohexyl-O(O)C—$CH_2$—, phenyl-O— optionally substituted with $CH_3O$—, phenyl substituted with two F, or phenyl optionally substituted with one $R^{4.1}$—, $R^{4.1}$—O—, $R^{4.1}$—$CH_2$—, $R^{4.1}$—$CH_2$—O—, Cl or NC—, wherein $R^{4.1}$ is selected independently from H, $CH_3$, $C_2H_5$, benzyl, HO(O)C—, $CH_3O(O)C$—, HO—$CH_2$—, $CH_3O$—$CH_2$—, $(CH_3)_2N$—$CH_2$—, H—[O—$CH_2$—$CH_2]_n$—, $R^{4.1.1}$HN(O)C—, $(R^{4.1.1})_2$N(O)C—, $R^{4.1.2}$HN(O)C— or $(R^{4.1.2})_2$N(O)C—, wherein n is 3, 4 or 5, $R^{4.1.1}$ is independently selected from H, H[O—$CH_2$—$CH_2]_2$—, H[O—$CH_2$—$CH_2]_3$—, or a five or six-membered heterocyclyl selected from piperidinyl optionally substituted with $CH_3$, pyrrolidinyl optionally substituted with one or two substituents selected independently from $CH_3$— or O=, tetrahydrofuranyl optionally substituted with $CH_3O$—, or tetrahydrothiophenyl optionally substituted with two O=, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, HO—$CH_2$—$CH_2$=, or O=, and $R^{4.1.2}$ is branched or unbranched $C_{1-4}$-alkyl optionally substituted with one or two substituents independently selected from O=, NC—, HO—, $CH_3O$—, $(CH_3)_2N$—, $Cl(CH_3)_3N$—, HO(O)C—, $CH_3O(O)C$—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl being optionally substituted with one or two substituents selected independently from $CH_3$— or O=.

14. The compound according to claim 1 wherein $R^5$ is H.

15. The compound according to claim 1 wherein $X^-$ is selected from chloride and trifluoroacetate.

16. The compound according to claim 1 wherein $R^6$ is selected from H or $CH_3$;

$R^2$ is $CH_3$;

$R^3$ is selected from $C_{1-4}$-alkyl optionally substituted with cyclohexyl, indolyl, HO(O)C—$CH_2$—, $CH_3O(O)C$—$CH_2$—, $C_2H_5$—O(O)C—$CH_2$— cyclohexyl-O(O)C—$CH_2$—, phenyl-O— optionally substituted with $CH_3O$—, phenyl substituted with two F, or phenyl optionally substituted with one $R^{3.1}$, $R^{3.1}$—O—, $R^{3.1}$—$CH_2$—, $R^{3.1}$—$CH_2$—O—, Cl or NC—, wherein $R^{3.1}$ is selected independently from H, $CH_3$—, $C_2H_5$—, benzyl, HO(O)C—, $CH_3O(O)C$—, HO—$CH_2$—, $CH_3O$—$CH_2$—, $(CH_3)_2N$—$CH_2$—, H—[O—$CH_2$—$CH_2]_n$—, $R^{3.1.1}$HN(O)C—, $(R^{3.1.1})_2$N(O)C—, $R^{3.1.2}$HN(O)C— or $(R^{3.1.2})_2$N(O)C—, wherein n is 3, 4 or 5, $R^{3.1.1}$ is selected from H, H—[O—$CH_2$—$CH_2]_2$—, H—[O—$CH_2$—$CH_2]_3$—, or a five or six-membered heterocycly selected from piperidinyl optionally substituted with $CH_3$, pyrrolidinyl optionally substituted with one or two substituents selected independently from $CH_3$— or O=, tetrahydrofuranyl optionally substituted with $CH_3O$—, or tetrahydrothiophenyl optionally substituted with two O=, or two substituents $R^{3.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, $HOCH_2$—$CH_2$—, or O=, and $R^{3.1.2}$ is branched or unbranched $C_{1-4}$-alkyl optionally substituted with one or two substituents selected independently from O=, NC—, HO—, $CH_3O$—, $(CH_3)_2N$—, $Cl(CH_3)_3N$—, $HO(O)C$—, $CH_3O(O)C$—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O=;

$R^4$ is selected from $C_{1-4}$-alkyl optionally substituted with one or two groups selected from cyclohexyl, indolyl, $HO(O)C$—$CH_2$—, $CH_3O(O)C$—$CH_2$—, $C_2H_5$—$O(O)C$—$CH_2$—, cyclohexyl-$O(O)C$—$CH_2$—, phenyl-O— optionally substituted with $CH_3O$—, phenyl substituted with two F, or phenyl optionally substituted with one $R^{4.1}$—, $R^{4.1}$—O—, $R^{4.1}$—$CH_2$—, $R^{4.1}$—$CH_2$—O—, Cl or NC—, wherein $R^{4.1}$ is selected independently from H, $CH_3$—, $C_2H_5$—, benzyl, $HO(O)C$—, $CH_3O(O)C$—, HO—$CH_2$—, $CH_3O$—$CH_2$—, $(CH_3)_2N$—$CH_2$—, H—[O—$CH_2$—$CH_2$]$_n$—, $R^{4.1.1}HN(O)C$—, $(R^{4.1.1})_2N(O)C$—, $R^{4.1.2}HN(O)C$— or $(R^{4.1.2})_2N(O)C$—, wherein n is 3, 4 or 5, $R^{4.1.1}$ is selected from H, H—[O—$CH_2$—$CH_2$]$_2$—, H—[O—$CH_2$—$CH_2$]$_3$—, or a five- or six-membered heterocyclyl selected from piperidinyl optionally substituted with $CH_3$, pyrrolidinyl optionally substituted with one or two substituents selected independently from $CH_3$— or O=, tetrahydrofuranyl optionally substituted with $CH_3O$—, or tetrahydrothiophenyl optionally substituted with two O=, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, HO—$CH_2$—$CH_2$—, or O=, and $R^{4.1.2}$ is branched or unbranched $C_{1-4}$-alkyl optionally substituted with one or two substituents independently from O=, NC—, HO—, $CH_3O$—, $(CH_3)_2N$—, $Cl(CH_3)_3N$—, $HO(O)C$—, $CH_3O(O)C$—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O=;

$R^5$ is H;

or $R^1$ and $R^2$ are together $R^{12}$, wherein $R^{12}$ is selected from —$CH_2$—$CH_2$—, —$CH_2$—$CH_2$—$CH_2$—, —$CH_2$—$CH_2$—$CH_2$—$CH_2$— each optionally substituted with $R^{12.1}$, wherein $R^{12.1}$ is selected from phenyl, optionally substituted with $CH_3$—;

or $R^1$, $R^2$ and $R^4$ together with the atoms connecting them form an aza-bicyclo [2.2.2] octane;

or $R^1$ and $R^5$ are together —$CH_2$—; and $X^-$ is selected from chloride or trifluoroacetate.

17. The compound according to claim 16 wherein
$R^1$ and $R^2$ are together $R^{12}$, wherein $R^{12}$ is —$CH_2$—$CH_2$—$CH_2$—;

$R^6$ is H;

$R^3$ is selected from $C_{1-4}$-alkyl substituted with phenyl optionally substituted with one $R^{3.1}$—, $R^{3.1}$—O—, $R^{3.1}$—$CH_2$— or $R^{3.1}$—$CH_2$—O—, wherein $R^{3.1}$ is selected independently from H, $CH_3$—, $C_2H_5$—, benzyl, $HO(O)C$—, $CH_3O(O)C$—, HO—$CH_2$—, $CH_3O$—$CH_2$—, $(CH_3)_2N$—$CH_2$—, H[O—$CH_2$—$CH_2$]$_n$—, $R^{3.1.1}HN(O)C$—, $(R^{3.1.1})_2N(O)C$—, $R^{3.1.2}HN(O)C$— or $(R^{3.1.2})_2N(O)C$—, wherein n is 3, 4 or 5, $R^{3.1.1}$ is selected from H, H—[$OCH_2$—$CH_2$]$_2$—, H—[$OCH_2$.—$CH_2$]$_3$—, or a five or six-membered heterocycly selected from piperidinyl optionally substituted with $CH_3$, pyrrolidinyl optionally substituted with one or two substituents selected independently from $CH_3$— or O=, tetrahydrofuranyl optionally substituted with $CH_3O$—, or tetrahydrothiophenyl optionally substituted with two O=, or two substituents $R^{3.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, $HOCH_2$—$CH_2$—, or O=, and $R^{3.1.2}$ is branched or unbranched $C_{1-4}$-alkyl optionally substituted with one or two substituents selected independently from O=, NC—, HO—, $CH_3O$—, $(CH_3)_2N$—, $Cl(CH_3)_3N$—, $HO(O)C$—, $CH_3O(O)C$—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O=; and $R^4$ is selected from $C_{1-4}$-alkyl substituted with phenyl optionally substituted with one $R^{4.1}$—, $R^{4.1}$—O—, $R^{4.1}$—$CH_2$— or $R^{4.1}$—$CH_2$—O—, wherein $R^{3.1}$ is selected independently from H, $CH_3$—, $C_2H_5$—, benzyl, $HO(O)C$—, $CH_3O(O)C$—, HO—$CH_2$—, $CH_3O$—$CH_2$—, $(CH_3)_2N$—$CH_2$—, H—[O—$CH_2$—$CH_2$]$_n$—, $R^{4.1.1}HN(O)C$—, $(R^{4.1.1})_2N(O)C$—, $R^{4.1.2}HN(O)C$— or $(R^{4.1.2})_2N(O)C$—, wherein n is 3, 4 or 5, $R^4$ is selected from H, H—[$OCH_2$—$CH_2$]$_2$—, H—[$OCH_2$.—$CH_2$]$_3$—, or a five or six-membered heterocycly selected from piperidinyl optionally substituted with $CH_3$, pyrrolidinyl optionally substituted with one or two substituents selected independently from $CH_3$— or O=, tetrahydrofuranyl optionally substituted with $CH_3O$—, or tetrahydrothiophenyl optionally substituted with two O=, or two substituents $R^{4.1.1}$ together with the nitrogen atom they are bound to form a five-, six- or nine-membered heterocyclyl selected from piperidinyl, piperazinyl, morpholinyl, thiomorpholinyl, tetrahydro-imidazo[1,2-a]pyrazine; each five-, six- or nine-membered heterocyclyl being optionally substituted with one or two substituents selected independently from $CH_3$, HO—, $HOCH_2$—, $HOCH_2$—$CH_2$—, or O=, and $R^{4.1.2}$ is branched or unbranched $C_{1-4}$-alkyl optionally substituted with one or two substituents selected independently from O=, NC—, HO—, $CH_3O$—, $(CH_3)_2N$—, $Cl(CH_3)_3N$—, HO(O)C—, $CH_3O(O)C$—, $HO(O)_2S$—, $CH_3(O)_2S$—, $CH_3(O)_2S$—, $(CH_3)_2OP$— or a five or six-membered heterocyclyl or heteroaryl selected from pyrrolidinyl, pyridyl, imidazolyl, piperidinyl, piperazinyl, morpholinyl; each five or six-membered heterocyclyl or heteroaryl optionally being substituted with one or two substituents selected independently from $CH_3$— or O=.

18. A pharmaceutical composition comprising at least one compound according to claim 1 or a pharmaceutically acceptable salt thereof and a pharmaceutically acceptable carrier.

19. A pharmaceutical composition according to claim 18 further comprising, as further active substances, one or more compounds selected from among the categories of further ENaC inhibitors, betamimetics, anticho-linergics, corticosteroids, PDE4-inhibitors, LTD4-antagonists, EGFR-inhibitors, dopamine ago-nists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

\* \* \* \* \*